US006630615B1

(12) United States Patent
Bidney et al.

(10) Patent No.: US 6,630,615 B1
(45) Date of Patent: Oct. 7, 2003

(54) DEFENSE-RELATED SIGNALING GENES AND METHODS OF USE

(75) Inventors: Dennis L. Bidney, Urbandale, IA (US); Oswald R. Crasta, Branford, CT (US); Xu Hu, Urbandale, IA (US); Guihua Lu, Urbandale, IA (US)

(73) Assignees: Pioneer Hi-Bred International, Inc., Des Moines, IA (US); Curagen Corporation, New Haven, CT (US)

( * ) Notice: Subject to any disclaimer, the term of this patent is extended or adjusted under 35 U.S.C. 154(b) by 136 days.

(21) Appl. No.: 09/640,419

(22) Filed: Aug. 17, 2000

Related U.S. Application Data
(60) Provisional application No. 60/206,405, filed on May 23, 2000, and provisional application No. 60/149,656, filed on Aug. 18, 1999.

(51) Int. Cl.[7] .................. C12N 15/09; C12N 15/29; C12N 15/82; A01H 5/00
(52) U.S. Cl. .................. 800/279; 800/278; 800/298; 800/286; 800/320; 800/320.1; 800/320.2; 800/312; 800/322; 800/306; 800/314; 435/320.1; 435/419; 435/468; 536/23.2; 536/23.6; 536/24.1; 536/24.5
(58) Field of Search .................. 800/278, 279, 800/298, 286, 320, 320.1, 320.2, 312, 322, 306, 314; 435/320.1, 419, 468; 536/23.2, 23.6, 24.1, 24.5

(56) References Cited

U.S. PATENT DOCUMENTS

| | | | |
|---|---|---|---|
| 5,530,187 A | | 6/1996 | Lamb et al. |
| 5,614,395 A | * | 3/1997 | Ryals et al. .............. 435/172.3 |
| 5,719,043 A | | 2/1998 | Frommer |
| 5,767,369 A | | 6/1998 | Ryals et al. |

FOREIGN PATENT DOCUMENTS

| | | |
|---|---|---|
| EP | 0392 225 A2 | 3/1990 |
| EP | 0926 241 A2 | 11/1998 |
| WO | WO 89/12059 A1 | 12/1989 |
| WO | WO 93/07279 A1 | 4/1993 |
| WO | WO 99/04013 A2 | 1/1999 |

OTHER PUBLICATIONS

Broun et al, "Catalytic Plasticity of Fatty Acid Modification Enzymes Underlying Chemical Diversity of Plant Lipids", 1998, Science vol. 281, pp. 1315–1317.*
Bevan M. et al., Neoxanthin Cleavage Enzyme–like Protein, Database EMBL (online) 049675, Jun. 1, 1998, XP002156633.
Iuchi, Satoshi et al., A Gene for a Key Enzyme in ABA Biosynthesis is Induced by Drought Stress in Cowpea, *Plant Cell Physiol.* 1998, pp. s105, vol. 39, Supplement.
Martini, Norbert et al., Promoter Sequences of a Potato Pathogenesis–Related Gene Mediatee Transcriptional Activation Selectively Upon Fungal Infection, *Mol. Gen. Genet*, 1993, pp. 179–186, vol. 236.

Thompson, A.J. et al., Regulation and Expression of Abscisic Acid Biosynthesis Genes in Tomato, *Journal of Experimental Botany*, May 1998, pp. 16, vol. 49 suppl., The Society for Experimental Biology Annual Meeting; London, England, UK.
Trezzini, Giampiero F. et al., Isolation of Putative Defense–Related Genes from *Arabidopsis Thaliana* and Expression in Fungal Elicitor–Treated Cells, *Plant Molecular Biology*, 1993, pp. 385–389, vol. 21, Kluwer Academic Pulbishers, Belgium.
Watillon, B. et al., M. Domestica mRNA for Lignostilbene Dioxygenase–like Protein, Database EMBL (online) MDZ93765, Mar. 2, 1998, XP002156633.
Chen, L. et al., LHT1, A Lysine– and Histidine–Specific Amino Acid Transporter in Arabidopsis, *Plant Physiol.*, 1997, pp. 1127–1134, vol. 115.
Fischer, W. et al., Substrate Specificity and Expression Profile of Amino Acid Transporters (AAPs) in Arabidopsis, *J Biol Chem*, Jul. 1995, pp. 16315–16320, vol. 270(27).
Hirner, B. et al., Developmental Control of $H^+$/amino Acid Permease Gene Expression During Seed Development of Arabidopsis, *The Plant Journal*, 1998, pp. 535–544, vol. 14(5).
Lalanne, E. et al., Isolation of a Nicotiana Sylvestris cDNA (Accession No.: U31932) Encoding an Amino Acid Transporter Homologous to *Arabidopsis thaliana* Amino Acid Permeases, *Plant Physiol.*, 1995, p. 722, vol. 109.
Lalanne, E. et al., Structure and Specific Expression of a *Nicotana Sylvestris* Putative Amino–Acid Transporter Gene in Mature and In Vitro Germinating Pollen, *Plant Molecular Biology*, 1997, pp. 855–864, vol. 35.
Rentsch, D. et al., NTR1 Encodes A High Affinity Oligopeptide Transporter in Arabidopsis, *FEBS Lett*, Aug. 21, 1995, pp. 264–268, vol. 370(3).
Schwartz, S. et al., Specific Oxidative Cleavage of Carotenoids by VP14 of Maize, *Science*, Jun. 20, 1997, pp. 1872–1874.
Song, W. et al., Cloning of a Second Arabidopsis Peptide Transport Gene, *Plant Physiol*, Jan. 1996, pp. 171–178, vol. 110(1).
Steiner, H.Y. et al., An Arabidopsis Peptide Transporter is a Member of a New Cass of Membrane Transport Proteins, *Plant Cell*, Sep. 1994, pp. 1289–1299, vol. 6(9).

* cited by examiner

Primary Examiner—Elizabeth F. McElwain
Assistant Examiner—Medina A. Ibrahim
(74) *Attorney, Agent, or Firm*—Alston & Bird LLP

(57) ABSTRACT

The invention relates to the genetic manipulation of plants, particularly to the expression of nucleotide sequences from defense-related signaling genes. Isolated nucleotide sequences encoding a neoxanthin cleavage enzyme, an amino acid permease, and a novel protein are provided. Also provided are isolated nucleotide sequences comprising promoters that drive expression in a plant in an inducible or tissue-preferred manner. The nucleotide sequences find use in increasing the resistance of plants to pathogens and other stresses, modifying ABA metabolism in plants, modifying amino acid transport and content in plants, and regulating gene expression in plants. Additionally provided are isolated proteins, and transformed plants and seeds thereof.

22 Claims, 7 Drawing Sheets

FIGURE 1

```
NCE       ------------------MDSLSSS-FIS-IFSQSNSTVSHPPPSSSSPPSALRVFSVRT
O49675    ------------------MDSVSSSSFLSSTFSLHHSLLRR---RSSSP-TLLRINSAVV
O49895    ------------------------------------------------------------
O24592    ---MQGLAPPTSVSIHRHLP-ARSRARASNSVRFSPRAVS-----SVPPAECLQAP--FH
O24023    MATTTSHATNTWIKTKLSMPSSKEFGFASNSISLLKNQHNR---QSLNINSSLQAPPILH

NCE       EEK-PETVTSTATTKRPSGPKKQPTLNIRKRE---SS---VVVDQSLPATIFNAFDSIIN
O49675    EERSPITNPSDNNDRR-NKPK---TLHNRTNHTLVSSPPKLRPEMTLATALFTTVEDVIN
O49895    ---------------------------------------------------MAPTRN
O24592    KPVADLPAPSRKPA-AIAVPGH--AAAPRKAEGG--KKQLNLFQRAAAAALDAFEEGFVA
O24023    FPKQSSNYQTPKNN-TISHPKQ--ENNNSSSSS---TSKWNLVQKAAAMALDAVESALTK

NCE       NFIDPP--ARVSVDPKHVLSDNFSPV-DELPPTDCEVIEGTLPSCLDGAYFRNGPNPQFL
O49675    TFIDPP--SRPSVDPKHVLSDNFAPVLDELPPTDCEIIHGTLPLSLNGAYIRNGPNPQFL
O49895    TFRVGP--TTCSTG-----TACFTPL-GSPEAARCSAADMSRPTSTPLSVT---PATLYF
O24592    NVLERPHGLPSTADPAVQIAGNFAPV-GERPPVHELPVSGRIPPFIDGVYARNGANPCFD
O24023    HELEHP--LPKTADPRVQISGNFAPV-PENPVCQSLPVTGKIPKCVQGVYVRNGANPLFE
                   *        :..    :   *:*:    .       *        . . :

NCE       PRGPYHLFDGDGMLHAIRISNG-KASLCSRYIKTYKYSIEKEAGFPIIPNVFSGFNGVTA
O49675    PRGPYHLFDGDGMLHAIKIHNG-KATLCSRYVKTYKYNVEKQTGAPVMPNVFSGFNGVTA
O49895    P-----------------T---SSLAS-------------TASPLPPHV---------
O24592    PVAGHHLFDGDGMVHALRIRNGAAESYACRFTETARLRQERAIGRPVFPKAIGELHG-HS
O24023    PTAGHHFFDGDGMVHAVQFKNGSAS-YACRFTETERLVQEKALGRPVFPKAIGELHG-HS
          *                         ..                  .  *: *:.

NCE       SAARMAVTAGRFLAGQFDPTKGIGLANTSLAFFGNRLFALGESDLPYAVKLAPDGDIVTV
O49675    SVARGALTAARVLTGQYNPVNGIGLANTSLAFFSNRLFALGESDLPYAVRLTESGDIETI
O49895    -----ALSAARVLTGQYNPANGIGLANTSLAFFGDRLYALGESDLPYSLRLTSNGDIETL
O24592    GIARLALFYARAACGLVDPSAGTGVANAGLVYFNGRLLAMSEDDLPYHVRVADDGDLETV
O24023    GIARLMLFYARGLFGLVDHSKGTGVANAGLVYFNNRLLAMSEDDLPYHVKVTPTGDLKTE
              : .*  *   :   * *:**:.*.:*..** *:.*.****  ::::  **: *

NCE       GREDFDGKLFMSMTAHPKIDPVTKEAFAFRYGPVP-PFLTFFRFNENGEKQADVPIFSMT
O49675    GRYDFDGKLAMSMTAHPKTDPITGETFAFRYGPVP-PFLTYFRFDSAGKKQRDVPIFSMT
O49895    GRHDFDGKLSMNMTAHPKIDPDTGEAFAFRYGFIR-PFLTYFRFDSNGVKQPDVPIFSMV
O24592    GRYDFDGQLGCAMIAHPKLDPATGELHALSYDVIKRPYLKYFYRPDGTKSDDVEIP-LE
O24023    GRFDFDGQLKSTMIAHPKLDPVSGELFALSYDVIQKPYLKYFRFSKNGEKSNDVEIP-VE
          ** ****:*   *  **** **  :   *. *: *.  :   *:*..:* *   *. ** * :

NCE       SPSFLHDFAITKNYAIFPEIQIGMSPMEMLG----GGSPVSADAGKVPRLGLIPRYAKDE
O49675    SPSFLHDFAITKRHAIFAEIQLGMR-MNMLDLVLEGGSPVGTDNGKTPRLGVIPKYAGDE
O49895    TPTFLHDFAITKKHAIFADIQIGLNLIDMIT---KRATPFGLDPSKVPRIGVIPLYAKDE
O24592    QPTMIHDFAITENFVVVPDHQVVFKLQEMLR----GGSPVVLDKEKTSRFGVLPKHAADA
O24023    DPTMMHDFAITENFVVIPDQQVVFKMSEMIR----GGSPVVYDKNKVSRFGILDKYAKDG
          *::::******:...:.: *: :   :*:         .:*.  *  *..*:*::  :* *

NCE       SEMKWFEVPGFNVIHCINAWEEDGGDTVVMVAPNILSVEHTLERMD-LIHASVEKVKINL
O49675    SEMKWFEVPGFNIIHAINAWDEDDGNSVVLIAPNIMSIEHTLERMD-LVHALVEKVKIDL
O49895    SEMRWFEVPGFNGVHATNAWDED--DAIVMVAPNVLSAEHVLERVD-LVHCLVEKVRIDL
```

FIGURE 1 (cont.)

```
024592      SEMAWVDVPDCFCFHLWNAWEDEATGEVVVIGSCMTPADSIFNESDERLESVLTEIRLDA
024023      SDLKWVEVPDCFCFHLWNAWEEAETDEIVVIGSCMTPPDSIFNECDEGLKSVLSEIRLNL
            *::  *.:**.     .*  ***::     .:*::..  :  .  :    ::. *  :..  : :::::

NCE         KTGMVSRHPLST-----RNLDFAVLNPAFVAVKNRYMYCGVGDPMPKISGVVKLDVSLSE
049675      VTGIVRRHPISA-----RNLDFAVINPAFLGRCSRYVYAAIGDPMPKISGVVKLDVSKGD
049895      KTGIVTRQPIST-----RNLDFAVINPAYLGRKNKYVYAAEGDPMPKISGVVKLDVSNVE
024592      RTGRSTRRAVLP-PSQQENLEVGMVNRNLLGRESRYAYLAVAEPWPKESGFAKEDLSTGE
024023      KTGKSTRKSIIENPDEQVNLEAGMVNRNKLGRKTEYAYLAIAEPWPKVSGFAKVNLFTGE
            **      *:.:          **:  ..:*     :.   ..*  *  .  .:* ** **..* ::      :

NCE         ADRRECIVASRMFGPGCYGGEPFFVAREPDNPDAD-EDDGYVVSYVHNENTGESRFVVMD
049675      RD--DCTVARRMYGSGCYGGEPFFVARDPGNPEAE-EDDGYVVTYVHDEVTGESKFLVMD
049895      HK--ECIVASRMFGPGCYGGEPFFVAREPENPEAD-EDNGFLVSYVHDEKAGESRFLVMD
024592      LT-------KFEYGEGRFGGEPCFVPMDPAAAHPRGEDDGYVLTFVHDERAGTSELLVVN
024023      VE-------KFIYGDNKYGGEPLFLPRDPNSKE---EDDGYILAFVHDEKEWKSELQIVN
                  :*  .  :****  *:.  :*         .       **:*::::**:*       *.:  :::

NCE         AKSPTLEIVDAVKLPHRVPYGFHGLFVRESDVNKL--
049675      AKSPELEIVAAVRLPRRVPYGFHGLFVKESDLNKL--
049895      AKSPQLDIVAAVRMPRRVPYGFHGLFVRESDLNNL--
024592      AAD--IRLEATVQLPSRVPFGFHGTFITGQELEAQAA
024023      AMS--LKLEATVKLPSRVPYGFHGTFINANDLANQA-
            *  .    :  :     :*::*  ***:****  *:      .::
```

Figure 2

```
004459     -------MGNSEM-SASEVAAAKQKN--VDDWLPITSSRN-AKWWYSAFHNVTAMVGAGV
Sun-AAP    MVSDGTQSQNQQY-GVDKVDNRSEKEKAIDAWLPITSSRN-AKWWYAAFHNVTAMVGAGV
Q40414     ------MVASPDN-NAADGRTVKNKRP-IDEWLPITSSRNGQNGGYSAFHNVTAMVGAGV
O24405     ---MVAQAPHDDHQDDEKLAAARQKE--IEDWLPITSSRN-AKWWYSAFHNVTAMVGAGV
O22719     --------------MKTLRDLQDQSFELEDWLPITASRN-ANWYYSAFHNVTAIVGAGV
                           ::       ::   ****:***   : *:********:****

004459     LSLPYAMSNLGWGPGVTIMVMSWIITLYTLWQMVEMHE---IVPGKRLDRYHELGQHAFG
Sun-AAP    LSLPYAMSELGWGPGVAVMVISWIVTVYTLWQMVEMHE---MVPGKRFDRYHELGQHAFG
Q40414     LGLPYAMSELGWGPGVTVMVVSWVITLYTLWQMVECKKCPGMLAGTCIDDHKLAVSNVFG
O24405     LGLPYAMSQLGWGPGIAVLVLSWVITLYTLWQMVEMHE---MVPGKRFDRYHELGQHAFG
O22719     LGLPYAMSELGWGPGVVVLILSWVITLYTFWQMIEMHE---MFEGKRFDRYHELGQAAFG
           *.******:*****::.::::**:*:**:***:*  ::    :. *. :* ::   . .**

004459     EKLGLWIVVPQQLIVEVGVDIVYMVTGGASLKKVHQLVCP--DCKEIRTTFWIMIFASVH
Sun-AAP    EKLGLYIVVPQQLVVEVSLCIIYMVTGGKSLQKFHDLLVRQDEQKDIRLTFFIMIYGSVH
Q40414     NKLGLWIVVPQQLVVEVGIDIVYMVTGGKSFQKSIVLVCK-DNCKDIKLTYYIMIFASVH
O24405     EKLGLYIVVPQQLIVEIGVCIVYMVTGGKSLKKFHELVCD--DCKPIKLTYFIMIFASVH
O22719     KKLGLYIVVPLQLLVETSACIVYMVTGGESLKKIHQLSVGDYECRKLKVRHFILIFASSQ
           :****:**** **:**  .  *:****** *::*    *     :   ::  ::*:*:.* :

004459     FVISHLPNFNSISIIISLAAAVMSLTYSTIAWAASVHKGVHPDVDYSPRASTDVGKVFNFL
Sun-AAP    FVLSHLPNFNSLSGISLAAAIMSLSYSTIAWGASLDKGVQPNVEYGYKAKSTTGTVFNFL
Q40414     FVLSHLPNFNAISGVSLVAAIMSLSYCTIAWGASIVLGVQPDVEYEYRAENTGEGIFNFF
O24405     FVLSHLPNFNSISGSFSCCCRYVSQLLNNRMGIISKQRCSRRRSIRLQSENNSRYVFNFF
O22719     FVLSLLKNFNSISGVSLVAAVMSMSYSTIAWVASLTKGVANNVEYGYKRRNNTSVPLAFL
           **:* *  ***::*          ..                .     : .      : *:

004459     NALGDVAFAYAGHNVVLEIQATIPSTPEMPSKVPMWRGVIVAYIVVAICYFPVAFLGYYI
Sun-AAP    SALGDMAFAYAGHNVVLEIQATIPSTPEKPSKGPMWKGVVVAYIVIALCYFPVAFIGYWV
Q40414     SGLGEVAFAYAGHNVVLEIQATIPSTPEKPSKGPMWKGVLVAYIIVALCYFPVAIIGYWI
O24405     SGLGDVAFAYAGHNVVLEIQATIPSTPEKPSKGPMWRGVIVAYIVVALCYFPVALVGYYI
O22719     GALGEMAFAYAGHNVVLEIQATIPSTPENPSKRPMWKGAIVAYIIVAFCYFPVALVGFWT
           ..**::******************* *** ***:*.:****::*:******::*:::

004459     FGNSVDDNILITLEKPIWLIAMANMFVVIHVIGSYQVFFHILIFAMPVFDMLETVLKKM
Sun-AAP    FGNGVDDNILITLEKPTWLIAMANMFVVVHVIGSYQ------LYAMPVFDMMETLLVKKL
Q40414     FGNSVSNNILISLEKPTWLIVLANAFVVITLLGAYQ------LYAIPVFDMLETYLVRKL
O24405     FGNGVEDNILMSLKKPAWLIATANIFVVIHVIGSYQ------IYAMPVFDMMETLLVKKL
O22719     FGNNVEENILKTLRGPKGLIIVANIFVIIHLMGSYQ------VYAMPVFDMIESVMIKKW
           ***.*.:***  :.** .*  .** **   :**:**        ::*:*****:*:  ::::*

004459     NFPSFKLRFITRSLYVAFTMIVAICVPFFGGLLGFFGGFAFAPTTYYLPCIMWLVLKKP
Sun-AAP    NFAPSFMLRFITRNVYVAFTMFVGICFPFFGGLLGFFGGLAFAPTTYFLPCIMWLCICKP
Q40414     KFKPTWYLRFMTRNLYVAFTMFVGIIFPFLWGLLGFLGGFAFAPTTYFLPCIMWLSIYKP
O24405     NFRPTTTLRFFVRNFYVAATMFVGMTFPFFGGLLAFFGGFAFAPTTYFLPCVIWLAIYKP
O22719     HFSPTRVLRFTIRWTFVAATMGIAVALPHFSALLSFFGGFIFAPTTYFIPCIIWLILKKP
           :* *:   ***   *    :**  **   . *  .**.*:**  :**.*:**: ****::*:*** :  **

004459     KRFGLSWTANWVCSLVINGVLLTILAPIGGLRTIIINAKTYKFFS--------------
Sun-AAP    RRWSLSWFTNWIC--IVLGVVLMVVAPIGGLRSIIVQAKTYKFFS--------------
Q40414     KRWGLSWTSNWIC--IIVGVMLTVLAPIGGLRTIIIQAKDYNFFYWDSLSGSLAFGKKG
O24405     KKYSLSWWANWVC--IVFGLFLMVLSPIGGLRTIVIQAKGYKFYS--------------
O22719     KRFSLSWCINWAS----------GTPPFG----LFVN----------------------
           ::::.***  **  .                .*:*      :.::
```

DEFENSE-RELATED SIGNALING GENES AND METHODS OF USE

CROSS-REFERENCE TO RELATED APPLICATIONS

This application claims the benefit of U.S. Provisional Application Nos. 60/149,656 and 60/206,405 filed on Aug. 18, 1999 and May 23, 2000, respectively.

FIELD OF THE INVENTION

The invention relates to the genetic manipulation of plants, particularly to transforming plants with genes that enhance disease resistance.

BACKGROUND OF THE INVENTION

Throughout their lives, plants are routinely subjected to a variety of stresses, which act to impede or alter growth and development processes. Stresses to plants may be caused by both biotic and abiotic agents. For example, biotic causes of stress include infection with a pathogen, insect feeding, and parasitism by another plant such as mistletoe, and even grazing by ruminant animals. Abiotic stresses include osmotic stress, excessive light intensity or insufficient light intensity, cold temperatures, warm temperatures, synthetic chemicals such as those used in agriculture, and excessive wind.

Because a stress negatively impacts plant growth and development processes, stress to agricultural plants has a negative economic impact expressed in the form of reduced yields, increased expenditures for pesticides, or both. Developing crop plants that are better able to tolerate or even avoid stresses is desirable and will most certainly improve agricultural productivity. Given the world's both increasing human population and diminishing land area available for agriculture, improving agricultural productivity is a paramount challenge. A thorough understanding of the mechanisms used by plants to avoid or tolerate stresses may help in the development of new strategies of improving the stress tolerance of agricultural plants.

In spite of the great frequency of stresses, plants survive, and often flourish. Plants are able to do this because of the evolution of a variety of internal and external mechanisms for avoiding or tolerating stress. For example, higher plants possess leaves with waxy, water-impermeable surfaces and pores known as stomata, which serve to allow the escape of water vapor during the process of transpiration. The periphery of the stomatal pores is lined with a pair of cells known as guard cells, which control the aperture of the pore. By modifying their size and shape through a turgor-pressure-mediated process, the guard cells can completely block the pore when conditions are unfavorable for transpiration during, for example, periods of low soil-water availability. Such a stress-avoidance system allows a plant to survive conditions of water stress by reducing transpiration to nearly zero and preventing dehydration.

Plants also possess defense systems which prevent or help limit the stresses resulting from attacks by pathogens and insects. One well-known defense system against plant pathogens is known as systemic acquired resistance. Another defense system is the systemic induction of proteinase inhibitors following insect damage, which is usually referred to as the systemic wound response. In both of these defense systems, the initial impact of the pathogen or insect is transmitted via a signal or signals to other parts of the plant, resulting in the increased expression of genes encoding proteins that are directly or indirectly inhibitory to the invading organism. The associated, systemic increase in defense gene products is known to increase the resistance of the plant to both current and future stresses from pathogens and insects.

While certain components of the systems that plants use to respond to abiotic and biotic stresses are known, most components have yet to be elucidated. Uncovering the genetic components of such systems will provide plant breeders with new targets for crop improvement strategies.

SUMMARY OF THE INVENTION

Methods and compositions for expressing defense-related, signaling genes are provided. The compositions comprise nucleotide sequences from defense-related, signaling genes isolated from sunflower. The nucleotide sequences of the invention relate to sunflower genes encoding a neoxanthin cleavage enzyme (NCE), an amino acid permease (AAP) and a novel glutamic acid-rich protein designated GRP (previously designated GPR). The compositions of the invention find use in agriculture, particularly in methods for increasing the resistance of plants to pathogens, methods for modifying abscisic acid metabolism in a plant, methods for modifying amino acid transport in a plant, and methods for modifying the amino acid content of a plant. The methods comprise stably transforming the genome of a plant with nucleotide sequences of the invention operably linked to a promoter that drives expression in a plant cell.

Methods for regulating gene expression in plants are provided. The methods comprise stably transforming a plant with a DNA construct comprising a promoter from either a sunflower NCE gene or a sunflower GRP gene operably linked to a second nucleotide sequence. Methods involving a promoter from the NCE gene find use in modulating the expression of a gene in a plant in response to pathogens, oxidative stress, oxidants, and defense-related signaling molecules such as, for example, jasmonic acid and salicylic acid. Methods involving a promoter from the GRP gene find use in preferentially expressing a gene in a plant stems.

Expression cassettes comprising sequences of the invention are provided. Additionally provided are transformed plants, plant tissues, plant cells, and seeds thereof. Isolated proteins encoded by the sequences of the invention are also provided.

BRIEF DESCRIPTION OF THE DRAWINGS

FIG. 1 provides an alignment of the amino acid sequence of the sunflower neoxanthin cleavage enzyme with neoxanthin cleavage enzyme-like proteins from other plants. The proteins include GenBank Accession Numbers O49675 from *Arabidopsis thaliana* (SEQ ID NO: 20), O49895 from *Malus domestica* (SEQ ID NO: 21), O24023 from *Lycopersicon esculentum* (SEQ ID NO: 22), and O24592 from *Zea mays* (SEQ ID NO: 23). A star below the aligned sequences indicates that the amino acid at that position is conserved across all five sequences. A dash within a sequence denotes a gap introduced into the sequence to achieve optimal alignment with the other sequences.

FIG. 2 provides an alignment of the amino acid sequence of the sunflower AAP with AAP-like proteins from other plants. The proteins include GenBank Accession Numbers O04459, O22719, and O24405 from *Arabidopsis thaliana* (SEQ ID NOs: 24–26, respectively), and Q40414 from *Nicotiana sylvestris* (SEQ ID NO: 27).

DETAILED DESCRIPTION OF THE INVENTION

Figure 3:
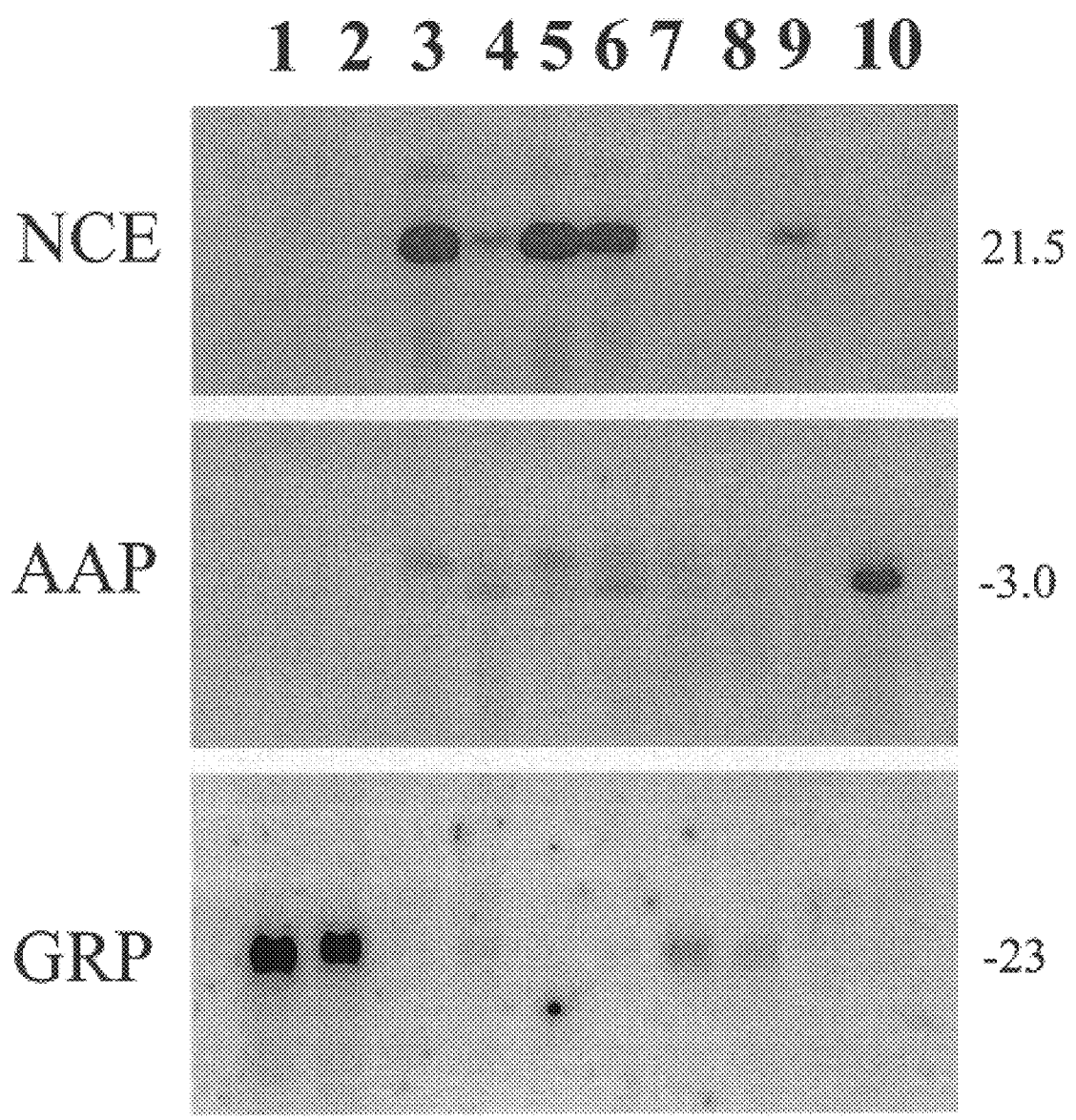
FIG. 3 depicts the results of a Northern blot analysis to determine the effects of Sclerotinia infection on transcript levels of defense-signaling genes in SMF3 sunflower tissues. The transcript levels of genes encoding sunflower NCE (upper panel), AAP (middle panel), and GRP (lower panel) were assessed. Lanes 1, 3, 5, and 7 contain RNA samples from control (uninoculated) sunflower plants or cultures. Lanes 2, 4, 6, and 8 represent RNA samples from sunflower plants or cultures inoculated with Sclerotinia. Lanes 1 and 2 contain RNA samples isolated from stems harvested on day 3. Lanes 3 and 4 contain RNA samples isolated from leaf tissues harvested on day 3. Lanes 5 and 6 contain RNA samples isolated from leaves harvested on day 5. Lanes 7 and 8 contain RNA samples isolated from non-infected and infected sunflower callus 12 hours after inoculation, respectively. For comparison, lanes 9 and 10 contain RNA samples isolated from leaves harvested from six-week-old SMF3 (lane 9) and oxox transgenic sunflower plants (lane 10). The numbers to the right of the panel indicate the CuraGen quantitative expression assay (RNA profiling) results. NCE was repressed in oxox plants by 21.5-fold, whereas AAP and GRP were induced 3- and 23-fold, respectively.

The invention relates to the isolation of defense-related signaling genes from sunflower. Sclerotinia is an economically important fungal pathogen of crops such as sunflower, canola (Brassica sp.), and soybean. Thus, resistance to this pathogen is a highly desirably trait to incorporate into susceptible crop plants. Transgenic sunflower plants that constitutively express a gene encoding oxalate oxidase (oxox) display enhanced resistance to Sclerotinia. See copending U.S. Application Serial No. 60/053,123 filed Jul. 18, 1997, herein incorporated by reference. Although the nature of this resistance phenomenon is unclear, it is known that the constitutive expression of a gene encoding oxox in sunflower causes the expression of other genes to be altered. The isolation, identification, and methods of use for three of these defense-related genes from sunflower is disclosed herein.

Methods and compositions for expressing defense-related, signaling genes are provided. The methods and compositions find use in agriculture, particularly in the breeding of crop plants with improved agronomic traits. The compositions comprise nucleotide sequences, and the proteins encoded thereof, from defense-related, signaling genes isolated from sunflower. The nucleotide sequences of the invention relate to sunflower genes encoding a neoxanthin cleavage enzyme (NCE) (SEQ ID NO: 1), an amino acid permease (AAP) (SEQ ID NO: 4), and a novel protein which has been designated GRP (SEQ ID NO: 6). Coding sequences are provided for each of the three sunflower genes set forth in SEQ ID NOs: 1, 4, and 6. The amino acid sequences set forth in SEQ ID NOs: 2, 5, and 7 disclose the sequences of the proteins encoded by the nucleotide sequences set forth in SEQ ID NOs: 1, 4, and 6, respectively. Additionally provided are nucleotide sequences comprising the promoters of an NCE gene (SEQ ID NO: 3) and a GRP gene (SEQ ID NO: 8).

Methods are provided for increasing the resistance of a plant to a pathogen. The methods comprise incorporating into the genome of a plant a DNA construct comprising a nucleotide sequence of the invention operably linked to a promoter that drives expression in a plant cell. The nucleotide sequences of the invention are selected from plant defense-signaling nucleotide sequences. Such nucleotide sequences include those encoding an NCE, AAP, or a GRP. Depending on the desired outcome, the nucleotide sequence of the invention may be operably linked to a promoter for the transcription of either sense or antisense transcripts. Furthermore, it is recognized that fragments of the nucleotide sequences of the invention may used in methods for increasing disease resistance in a plant. Such a fragment may encode a domain or portion of a protein that when expressed in a plant increases the disease resistance of the plant. Alternatively, such a fragment may be operably linked to a promoter for the transcription of antisense transcripts. While the choice of promoter depends on the desired level, timing, and localization of expression, the preferred promoters for operably linking to the nucleotide sequences of the invention are constitutive, pathogen-inducible, and wound-inducible promoters.

While the methods of invention may be used to increase the resistance of a plant to any pathogen, the preferred pathogens are those that cause plant diseases. More preferably, the pathogens are plant-disease-causing fungi, bacteria, and viruses. Most preferably, the pathogens are Scierotinia spp. that cause plant diseases.

NCE is involved in the biosynthesis of the plant signal molecule, abscisic acid (ABA) (Giraudat et al. (1994) *Plant Mol. Biol.* 26:1557–77; Schwartz et al. (1997) *Science* 276:1872–1874). NCE catalyzes the cleavage of neoxanthin into xanthoxin in the biosynthetic pathway leading to ABA. Originally identified as positive regulator of leaf abscission, ABA is a ubiquitous plant signal molecule that is involved in a variety of physiological processes including seed development, dormancy, and germination, osmotic-stress responses and defense responses such as the induction of the wound-inducible proteinase inhibitors of tomato and potato (Zeevaart et al. (1988) *Ann Rev. Plant Physiol. Plant Mol. Biol.* 39:439). During or immediately following a stress, ABA levels generally increase in plants. Stress-induced increases in ABA levels in plants are associated with stomatal closure, changes in gene expression, and plant adaptations to stress (Giraudat et al. (1994) *Plant Mol. Biol.* 26:1557–77; Schwartz et al. (1997) *Science* 276:1872–1874; Iturriaga et al. (1994) *Plant Mol. Biol.* 24:235–40). While the physiological role of ABA in signal transduction has not been determined, a recent report revealed that ABA functions through cyclic ADP-ribose in plants (Wu et al. (1998) *Science* 278:2126–30).

A first embodiment of invention involves increasing the resistance of a plant to a pathogen by decreasing the level of an NCE in the plant by transforming the plant with a nucleotide sequence corresponding to at least a portion of an NCE transcript operably linked to a promoter that drives expression in a plant. In sunflower, one or more NCE genes are expressed in leaves, and upon infection with Sclerotinia, the steady-state level of NCE transcripts in leaves is reduced relative to the level in uninfected leaves. Transgenic sunflower plants constitutively expressing a gene encoding oxalate oxidase display increased levels of resistance to Sclerotinia relative to the level of resistance of non-transgenic plants. Such transgenic also have a reduced level of NCE transcripts in their leaves relative to non-transgenic plants. Thus, reducing the level of NCE transcripts in a plant may also increase resistance in a plant. Preferably, the NCE nucleotide sequence is selected from the sequence set forth in SEQ ID NO: 1 and a nucleotide sequence encoding the amino acid sequence set forth in SEQ ID NO: 2. While the choice of promoter depends on the desired timing, level, and localization of expression, the promoter is preferably selected from pathogen-inducible promoters and constitutive promoters. It is recognized that a native promoter from an NCE gene may also be utilized.

Long-distance transport of amino acids is mediated by several families of differentially expressed amino acid transporters. AAPs play important roles in amino acid transport (Hirner et al. (1999) *Plant J.* 14:535–44). AAPs are members of a family of integral membrane proteins that function as transporters of amino acids and peptides across membranes. There is now a great deal of physiological and biochemical evidence for specific amino acid carriers involved in the uptake and transport of different amino acids in plants (Hirner et al. (1999) *Plant J.* 14:535–44). The substrate specificity of these transporters varies. Some AAPs are specific for one or only a few amino acids. Others, however, are more promiscuous and are capable of transporting several different amino acids across membranes. The isolation of a cDNA encoding a sunflower AAP is disclosed herein. Also disclosed is that the gene encoding this AAP displays increased expression in transgenic plants constitutively expressing an oxox gene, relative to expression in similar, non-transgenic plants.

A second embodiment of invention involves increasing the resistance of a plant to a pathogen by increasing the level of an AAP in the plant by transforming the plant with a nucleotide sequence encoding an AAP operably linked to a promoter that drives expression in a plant. Transgenic sunflower plants constitutively expressing a gene encoding oxalate oxidase display increased levels of resistance to Scierotinia relative to the level of resistance of non-transgenic plants. Such transgenic plants also have an increased level of AAP transcripts in their leaves relative to non-transgenic plants. It is recognized that increasing the transport of amino acids in a plant, such as transport mediated by AAPs, may increase the resistance of the plant to a pathogen by either increasing transport of a particular amino acid or class of amino acids.

Salicylic acid, a phenolic compound, is a key defense signal molecule in the well-known defense response phenomenon, systemic acquired resistance. The amino acid phenylalanine is a precursor in plants for the biosynthesis of a variety of defense-related molecules such as, for example, lignin, alkaloids, and phenolics including salicylic acid. Increasing the level in a plant of an AAP that transports phenylalanine may increase the level of phenylalanine available for salicylic acid biosynthesis and thus lead to an increased level of salicylic acid and increased disease resistance. Preferably, the increase in such an AAP occurs in a plant prior to, or at the time of, and in the vicinity of, the initial site of pathogen attack or infection.

Thus, the resistance of a plant to a pathogen may be increased by increasing the level of an AAP in the plant comprising transforming the plant with a nucleotide sequence encoding an AAP operably linked to a promoter that drives expression in a plant. The AAP nucleotide sequence is preferably selected from the sequence set forth in SEQ ID NO: 4 and a nucleotide sequence encoding the amino acid sequence set forth in SEQ ID NO: 5. While the choice of promoter depends on the desired timing, level, and localization of expression, preferred promoters are pathogen-inducible promoters and constitutive promoters.

The isolation of a nucleotide sequence encoding a novel protein, designated GRP, is disclosed herein. Transgenic sunflower plants constitutively expressing a gene encoding oxalate oxidase display increased levels of resistance to Sclerotinia relative to the level of resistance of non-transgenic plants. Such transgenic plants also have a increased level of GRP gene transcripts in their leaves relative to non-transgenic plants. Thus, GRP may play an important role in plant defense responses.

A third embodiment of the invention involves increasing the resistance of a plant to a pathogen by increasing the level of GRP in the plant comprising transforming the plant with a nucleotide sequence encoding GRP operably linked to a promoter that drives expression in a plant. Preferably, the GRP nucleotide sequence is selected from the sequence set forth in SEQ ID NO: 6 and a nucleotide sequence encoding the amino acid sequence set forth in SEQ ID NO: 7. When expressed in a plant, such a GRP sequence increases the level of GRP in a plant. Thus, increasing the level of GRP in a plant may increase the resistance of the plant to a pathogen.

Methods for modifying ABA metabolism in a plant are provided. By "ABA metabolism" is intended metabolism that involves the metabolic pathways a plant uses to synthesize and degrade ABA, and by "ABA metabolite" is intended a metabolite of such a pathway. ABA is a plant growth regulator that is involved in a variety of physiological processes including growth inhibition and responses to biotic and abiotic stresses. By modifying ABA metabolism in a plant, the level of ABA can also be modified. Thus, the methods of the invention find use in modifying any physiological process in a plant that is affected by the endogenous level of ABA in the plant.

In addition, the methods for modifying ABA metabolism may be used to increase or decrease the level of one or more ABA metabolites. It is recognized that ABA metabolites include carotenoids, particularly xanthophylls and carotenes. Furthermore, certain carotenoids such as, for example, β-carotene and lycopene, are antioxidants that are marketed as nutraceuticals because they may help to protect the human body against certain forms of cancer. By modulating the levels of one or more enzymes in the ABA biosynthesis pathway, the levels of one or more ABA metabolites may also be modulated. Thus, the methods of the invention find use in producing intermediates associated with ABA metabolism.

By "modifying" or "modulating" is intended increasing or decreasing the level of a cellular component such as, for example, a protein, a transcript or a metabolite, or the level of a cellular activity, such as for example, an enzyme activity, an activity of a transporter or an activity of a receptor.

The methods for modifying ABA metabolism in a plant comprise stably incorporating into the genome of a plant a nucleotide sequence encoding an enzyme involved in ABA metabolism operably linked to a promoter that drives expression in a plant. Preferably, such a nucleotide sequence encodes an NCE, a key enzyme in the ABA biosynthesis pathway. More preferably, such a nucleotide sequence encodes a sunflower NCE. Most preferably, such a nucleotide sequence is the nucleotide sequence set forth in SEQ ID NO: 1 or a nucleotide sequence encoding the amino acid sequence set forth in SEQ ID NO: 2. While the choice of promoter depends on the desired timing, level and localization of expression, preferred promoters include constitutive, tissue-preferred, pathogen-inducible, wound-inducible, and chemically regulated promoters.

The methods for modifying ABA metabolism in a plant find use in increasing the tolerance of a plant to a stress. Increased levels of ABA in a plant are known to be associated with plant responses to abiotic and biotic stress. It is also known that such increased levels of ABA in a plant are involved in helping a plant to tolerate or recover from such stresses. Thus, increasing the level of ABA in a plant may increase the tolerance of a plant to a stress. Such a stress may be, for example, water stress, salt stress, heat stress, cold stress, stress caused by a pathogen, or stress caused by an insect.

A fourth embodiment of the invention involves increasing the level of ABA in a plant by increasing the level in a plant of a key enzyme in ABA biosynthesis, particularly NCE. To increase the level of ABA in a plant, the plant is transformed with a DNA construct comprising an NCE nucleotide sequence of the invention operably linked to a promoter that drives expression in a plant. As a key enzyme in the ABA biosynthesis pathway, increasing the level of NCE in a plant can increase the flux through the pathway in the direction of ABA, resulting in an increased level of ABA. The plant may be transformed with one of more additional DNA constructs comprising a nucleotide sequence encoding an enzyme in the ABA biosynthetic pathway operably linked to a promoter that drives expression in a plant. Such additional nucleotide sequences include, but are not limited to, those encoding the enzyme that catalyzes the conversion of xanthoxin to ABA-aldehyde and the enzyme that catalyzes the conversion of ABA-aldehyde to ABA.

NCE possesses a putative chloroplast-targeting, transit peptide at its N-terminus. While NCE is not known to be localized to a particular organelle, it is expected to be found in chloroplasts and/or other plastids. In plants, carotenoids are predominantly found in plastids such as, for example, chloroplasts and chromoplasts. In addition, substrates of NCE, neoxanthin and violaxanthin, occur predominantly in the chloroplast: Furthermore, in green plant tissues, most free ABA is found in chloroplasts. Thus, it may be desirable to increase the level of NCE in chloroplasts, or other plastids.

Figure 4:
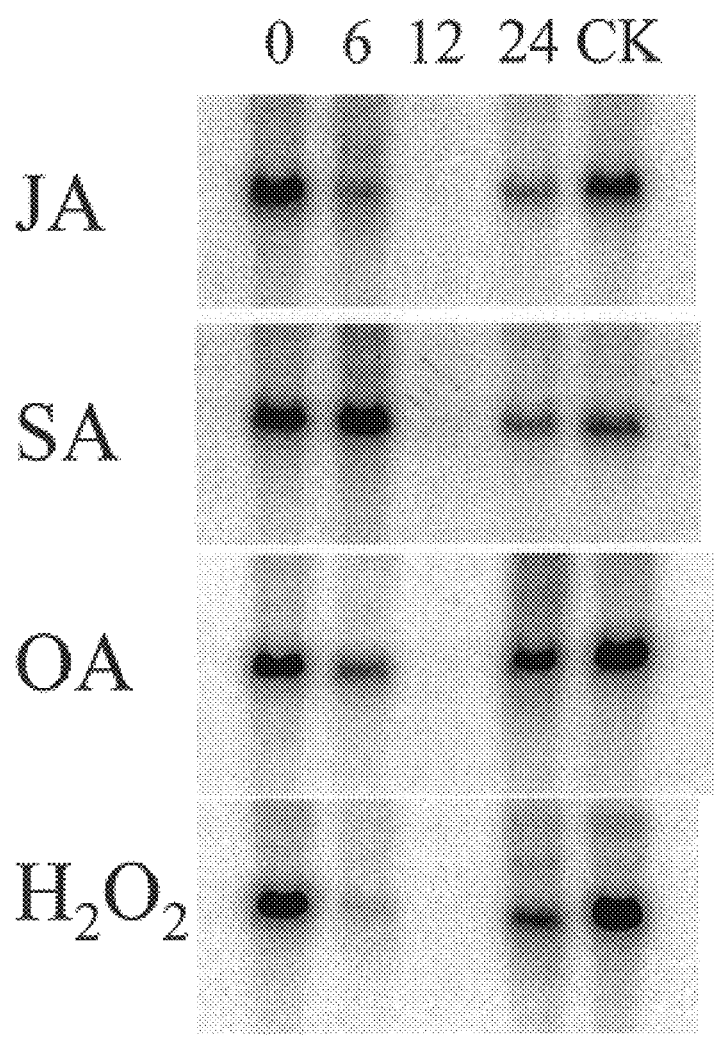
FIG. 4 depicts the results of a Northern blot analysis of NCE gene transcript levels under different chemical treatments. Six-week-old sunflower plants were sprayed with oxalic acid (OA) (5 mM), $H_2O_2$ (5 mM), salicylic acid (SA) (5 mM), and jasmonic acid (JA) (45 $\mu$M in 0.1% ethanol). The leaf samples were collected at 0, 6, 12, and 24 hours after the applications and immediately frozen in liquid nitrogen. Twenty $\mu$g of total RNA was loaded in each sample lane. (CK, control)
Figure 6:
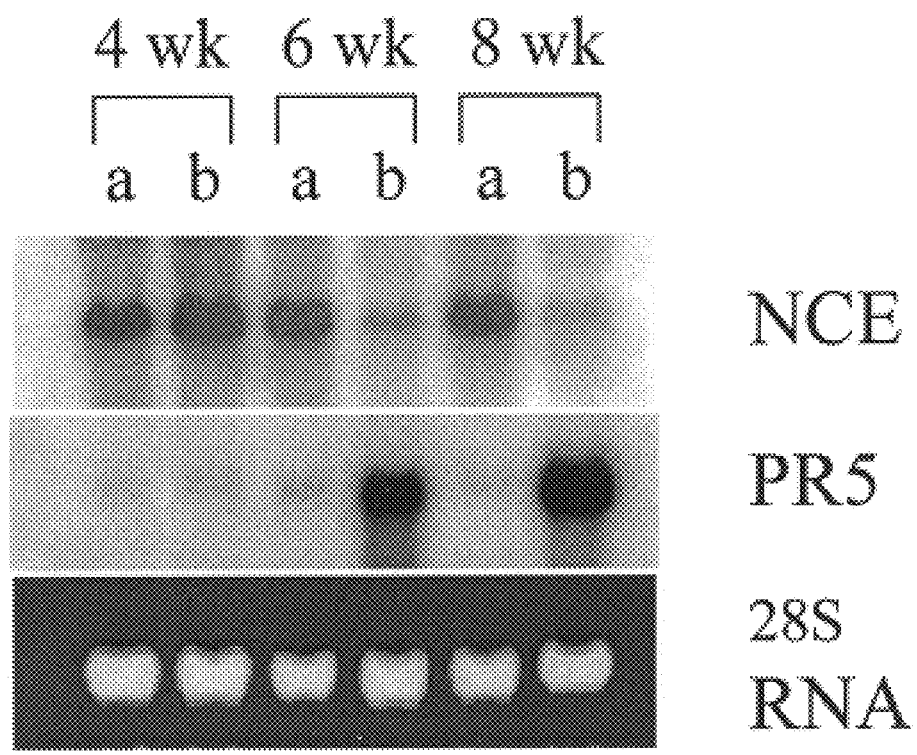
FIG. 6 depicts the results of a Northern blot analysis of NCE and PR5 gene transcript levels in SMF3 and oxox-transgenic leaf tissues at three developmental stages. Total RNA (20 $\mu$g/lane) isolated from non-transformed SMF3 leaf tissues (a) and from oxox-transgenic leaf tissues (b) harvested at four, six and eight weeks after planting was utilized. The lowest panel represents an RNA gel loading control which depicts the fluorescence of the 28S rRNA bands in the presence of ultraviolet radiation following ethidium bromide staining.

There is evidence to show that abiotic response pathways such as, for example, wound response pathways, might also play a role in defense against specific fungal pathogens. The signaling molecules jasmonic acid and ethylene both regulate the expression of wound response genes and some basic PR genes in tobacco, and the defensin (PDF1.2) and thionin genes in Arabidopsis (Maleck and Dietrich (1999) *Trends Plant Sci.* 4:215–219). Herein disclosed is the expression of a gene encoding an NCE that is down-regulated by Sclerotinia infection, jasmonic acid, salicylic acid, and $H_2O_2$ treatments (FIGS. 3 and 4). Notably, the time course of down regulation in NCE gene expression closely coincided with the time course of up-regulation in PR5 gene expression (FIG. 6). Thus, the Sclerotinia defense pathways may cross talk with the ABA biosynthesis pathway in a negative parallel manner in sunflower. Therefore, decreasing the level of ABA may increase the resistance to Sclerotinia in sunflower.

A fifth embodiment of the invention involves decreasing the level of ABA in a plant by eliminating, or reducing the level of, NCE in the plant. NCE is a key enzyme in ABA biosynthesis in plants. To lower the level of NCE in a plant, the plant is transformed with a DNA construct comprising a nucleotide sequence encoding at least a portion of an NCE transcript operably linked to a promoter in an orientation for the production of antisense NCE transcripts. Alternatively, a cosuppression approach may be employed to decrease production of NCE in the plant. By decreasing or eliminating NCE in a plant, the level of any one or more of ABA, ABA-aldehyde, xanthoxin, and ABA conjugates may be reduced in the plant. In addition, the levels of 9-cis-violaxanthin and 9'-cis-neoxanthin, substrates of NCE, may be increased. Furthermore, blocking or inhibiting the flux of ABA metabolites in a plant toward the synthesis of ABA may lead to a buildup of one or more desirable carotenoids, including, but not limited to, xanthophylls, β-carotene and lycopene.

It is recognized that by reducing the level of NCE in a plant, the level of ABA, or any ABA metabolite between neoxanthin and ABA, may be reduced in the plant. It is further recognized that by lowering the level of an NCE in a plant, the level of neoxanthin, or any other ABA metabolite that occurs in the ABA biosynthesis pathway prior to NCE, may be increased in the plant.

Methods for modulating amino acid transport in a plant are provided. The methods find use in modulating the level and/or content of one or more amino acids in a plant, or in any cell, tissue, or organ thereof. By modulating in a plant the level of one or more amino acids necessary for the biosynthesis of a protein, the level of one or more proteins in the plant may be altered. The methods comprise transforming a plant with a nucleotide sequence encoding a protein that mediates the transport of amino acids across membranes, particularly biological membranes, operably linked to a promoter that drives expression in a plant. Preferably, such a nucleotide sequence encodes an AAP. More preferably, such a nucleotide sequence encodes a sunflower AAP. Most preferably, such a nucleotide sequence is the nucleotide sequence set forth in SEQ ID NO: 4 or a nucleotide sequence encoding the amino acid sequence set forth in SEQ ID NO: 5. While the choice of promoter depends on the desired timing, level, and localization of expression, the promoter is preferably selected from constitutive, tissue-preferred, and seed-preferred promoters.

Methods are provided for modifying the amino acid content of a plant. The methods involve modifying a plant to produce an increased level of a protein which contains high percentages of the amino acids, glutamic acid and proline. The methods find use in agriculture for increasing the glutamic acid and/or proline content of a plant, particularly, a part of a plant that is harvested for human or animal consumption, more particularly a seed. The amino acid content of the GRP (SEQ ID NO: 7) disclosed herein comprises approximately 26.6% glutamic acid residues and 12.7% proline residues. The methods comprise stably incorporating in the genome of a plant a GRP nucleotide sequence of the invention operably linked to a promoter capable of driving gene expression in a plant. Preferred GRP nucleotide sequences include the sunflower GRP nucleotide sequence set forth in SEQ ID NO: 6 and a nucleotide sequence encoding the amino acid sequence of a sunflower GRP set forth in SEQ ID NO: 7.

While a nucleotide sequence which encodes a native GRP may be used in the methods of the invention, it may be desirable to alter, preferably reduce, more preferably eliminate, the native GRP activity of the encoded GRP. Thus, a nucleotide sequence may be the modified to alter one or more amino acids in the encoded protein. The nucleotide sequences of the invention may be modified to increase the content of glutamic acid, proline, or both, in the encoded protein to levels higher than in found in the proteins encoded by the native sequences. Furthermore, fragments of the nucleotide sequences of the invention that encode protein domains with a particularly high level of glutamic acid or proline can be combined with other nucleotide sequences to increase the level of glutamic acid or proline in the encoded fusion protein. Alternatively, a nucleotide sequence fragment that encodes a protein domain having, for example, a particularly high level of glutamic acid can be used to synthesize a nucleotide sequence comprising multiple repeats of such a fragment. A protein encoded by repeats of such a nucleotide sequence encodes a glutamic acid-rich protein comprised of repeated, glutamic acid-rich domains. For example, a 27-amino-acid domain of GRP (amino acids 79–105 of SEQ ID NO: 7) possesses approximately 44% (12/27) glutamic acid residues.

Generally, it is desirable to direct the production of the GRP to a part of the plant that is harvested and/or is used for food or animal feed. While the choice of promoter depends on the desired timing, level, and localization of expression, the promoter is preferably selected from constitutive, tissue-preferred, and seed-preferred promoters. A GRP may be targeted to a specific cellular organelle, such as, for example, a protein body, by operably linking an appropriate targeting sequence to the nucleotide sequence encoding the GRP.

Methods for regulating gene expression in a plant in response to a stimulus are provided. The methods comprise transforming a plant with an inducible promoter operably linked to direct the expression of a nucleotide sequence of interest in response to a stimulus. The promoter is selected from a nucleotide sequence of a promoter of a defense-signaling gene, particularly a promoter from an NCE gene. Preferably, such a promoter is from a sunflower NCE gene. More preferably, such a promoter is from a sunflower NCE gene that displays reduced gene expression in response to one or more stimuli including infection with a pathogen, damage from a pathogen, hydrogen peroxide, jasmonic acid, methyl jasmonate, salicylic acid, oxalic acid, and the expression of a gene encoding oxalic acid oxidase. Most preferably, such a promoter comprises the nucleotide sequence set forth in SEQ ID NO: 3.

While the methods of regulating gene expression may be used to regulate the expression of any nucleotide sequence of interest, the nucleotide sequence of interest is selected on the basis of the desired outcome. Generally, the nucleotide sequences of interest encode proteins or are antisense nucleotide sequences that correspond to transcripts from genes which encode proteins. Preferred nucleotide sequences of interest include defense activator nucleotide sequences. See copending U.S. application Ser. Nos. 09/256,158 and 09/257,541 both filed Feb. 24, 1999; herein incorporated by reference.

In a sixth embodiment of the invention, methods are provided for regulating the expression of a defense activator nucleotide sequence involving operably linking a promoter of the invention to a defense activator nucleotide sequence. The methods of the invention find use in determining the role of defense activators in activating plant defense responses. The expression of such a defense activator nucleotide sequence in a plant may be used to induce the disease resistance pathway resulting in levels of immunity in the plant that impart resistance to the pathogen or induce cell death. However, it is unknown if such induced disease resistance requires the expression of a defense activator nucleotide sequence following the infection of a plant with a pathogen. The methods of the present invention involve the use of a promoter that down-regulates gene expression in a plant following infection of the plant with a pathogen. Thus, the expression of a defense activator that is operably linked to a promoter of the invention is down-regulated. Alternatively, if the defense activator nucleotide sequence is, for example, native to the genome of a plant, the methods of the invention may be used to suppress the expression of a native defense activator through antisense suppression. Such methods involve operably linking the promoter of the invention to a defense activator nucleotide sequence in the antisense orientation for the production of antisense transcripts.

Methods are provided for stem-preferred regulation of gene expression in a plant. The methods involve transforming a plant with a DNA construct comprising a GRP promoter of the invention (SEQ ID NO: 8) operably linked to a nucleotide sequence. In both SMF3 and oxox transgenic sunflower plants, GRP transcript levels are significantly elevated in stems compared to the levels present in young seeds, corolla tubes, leaves, and roots, indicating that the GRP promoter preferentially drives expression in stems relative to the other tissues. Thus, the methods find use in directing stem-preferred expression of a desired nucleotide sequence in a plant.

While the methods of the invention can be used to drive the expression of any nucleotide sequence operably linked to a GRP promoter of the invention, preferred nucleotide sequences are those that improve at least one agronomically important trait of a crop plant including, but not limited to, nucleotide sequences that improve disease and/or insect resistance, increase stem strength, decrease stem height, and improve the nutritional value of stems for livestock feed. Of particular interest are nucleotide sequences which confer resistance to stem diseases including, but not limited to, Sclerotinia stem rot, Phoma black stem, and Phomopsis stem canker. For example, the GRP promoter can be operably linked to a nucleotide sequence encoding oxalate oxidase to improve the resistance of sunflower plants to Sclerotinia. Additionally, the GRP promoter can be used to drive the stem-preferred expression of nucleotide sequences encoding proteins with insecticidal activity against stem-damaging insects such as, for example, the European corn borer. Nucleotide sequences of interest that can be operably linked to the GRP promoter of the invention include, but are limited to, disease resistance genes, sequences encoding insecticidal proteins such as, for example, the well-known *Bacillus thuringiensis* (Bt) insecticidal proteins and sequences encoding enzymes or other proteins involved in gibberellin biosynthesis, degradation or action.

Compositions of the invention include isolated nucleotide sequences, isolated proteins, and expression cassettes that are related to defense-signaling genes. In particular, the present invention provides for isolated nucleic acid molecules comprising nucleotide sequences encoding the amino acid sequences shown in SEQ ID NOs: 2, 5, and 7 or the DNA sequences deposited in a bacterial host as Patent Deposit Nos. PTA-78, PTA-79, and PTA-68 in the ATCC Patent Depository. Further provided are polypeptides having an amino acid sequence encoded by a nucleic acid molecule described herein, for example those set forth in SEQ ID NOs: 1, 4, and 6, those deposited with the ATCC in a bacterial host as Patent Deposit Nos. PTA-78, PTA-79, and PTA-68, and fragments and variants thereof. Also provided are isolated nucleotide molecules comprising the promoter nucleotide sequences set forth in SEQ ID NOs: 3 and 8 which were deposited with the ATCC in a bacterial host as Patent Deposit Nos. Patent Deposit Nos. PTA-77 and PTA-1722, and fragments and variants thereof.

Plasmids containing the nucleotide sequences of the invention were deposited with the Patent Depository of the American Type Culture Collection (ATCC), Manassas, Va., and assigned Patent Deposit Nos. PTA-68, PTA-77, PTA-78, PTA-79 and PTA-1722. PTA-77, PTA-78, and PTA-79 were deposited with the ATCC on May 13, 1999. PTA-68 was deposited with the ATCC on May 14, 1999. PTA-1722 was deposited with the ATCC on Apr. 18, 2000. These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. §112.

The invention encompasses isolated or substantially purified nucleic acid or protein compositions. An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, (by dry weight) of contaminating protein. When the protein of the invention or biologically active portion thereof is recombinantly produced, preferably culture medium represents less than about 30%, 20%, 10%, or 5% (by dry weight) of chemical precursors or non-protein-of-interest chemicals.

Fragments and variants of the disclosed nucleotide sequences and proteins encoded thereby are also encompassed by the present invention. By "fragment" is intended a portion of the nucleotide sequence or a portion of the amino acid sequence and hence protein encoded thereby. Fragments of a nucleotide sequence may encode protein fragments that retain the biological activity of the native protein. For nucleotide sequences encoding an NCE, a fragment may encode a protein retaining NCE activity. For nucleotide sequences encoding an AAP, a fragment may encode a protein retaining AAP activity. For nucleotide sequences encoding a GRP, a fragment may encode a protein retaining the function of the native GRP protein. Fragments of a nucleotide sequence that are useful as hybridization probes may or may not encode fragment proteins retaining biological activity. Such fragments of a nucleotide sequence may range from at least about 20 nucleotides, about 50 nucleotides, about 100 nucleotides, and up to the full-length promoter sequence or full-length nucleotide sequence encoding the protein of the invention.

A fragment of an NCE nucleotide sequence that encodes a biologically active portion of a protein of the invention will encode at least 15, 25, 30, 50, 100, 150, 200, 250, 300, 350, 400, 450, or 500 contiguous amino acids, or up to the total number of amino acids present in a full-length NCE protein of the invention (for example, 592 amino acids for SEQ ID NO: 2). Fragments of an NCE nucleotide sequence that are useful as hybridization probes for PCR primers generally need not encode a biologically active portion of an NCE protein.

Thus, a fragment of an NCE nucleotide sequence may encode a biologically active portion of an NCE. Such a fragment may also be used as a hybridization probe or PCR primer using methods disclosed below. A biologically active portion of an NCE protein can be prepared by isolating a portion of an NCE coding sequence of the invention, expressing the encoded portion of the NCE protein (e.g., by recombinant expression in vitro), and assessing the activity of the portion of the NCE protein. Nucleic acid molecules that are fragments of an NCE coding sequence comprise at least 15, 20, 50, 75, 100, 150, 200, 250, 300, 350, 400, 450, 500, 550, 600, 650, 700, 800, 900, 1,000, 1,100, 1,200, 1,300, 1,400, 1,500, 1,600, 1,700, 1,800, or 1,900 nucleotides, or up to the number of nucleotides present in a full-length NCE nucleotide sequence disclosed herein (for example, 1,950 nucleotides for SEQ ID NO: 1).

A fragment of an AAP nucleotide sequence that encodes a biologically active portion of a protein of the invention will encode at least 15, 25, 30, 50, 100, 150, 200, 250, 300, 350, 400, or 450 contiguous amino acids, or up to the total number of amino acids present in a full-length AAP protein of the invention (for example, 452 amino acids for SEQ ID NO: 5). Fragments of a AAP nucleotide sequence that are useful as hybridization probes for PCR primers generally need not encode a biologically active portion of a AAP protein.

Thus, a fragment of a AAP nucleotide sequence may encode a biologically active portion of an AAP protein. Such a fragment may also be used as a hybridization probe or PCR primer using methods disclosed below. A biologically active portion of a AAP protein can be prepared by isolating a portion of one of the AAP coding sequences of the invention, expressing the encoded portion of the AAP protein (e.g., by recombinant expression in vitro), and assessing the activity of the portion of the AAP protein. Nucleic acid molecules that are fragments of a AAP coding sequence comprise at least 15, 20, 50, 75, 100, 150, 200, 250, 300, 350, 400, 450, 500, 550, 600, 650, 700, 800, 900, 1,000, 1,100, 1,200, 1,300, 1,400, 1,500, or 1,600, nucleotides, or up to the number of nucleotides present in a full-length AAP nucleotide sequence disclosed herein (for example, 1,656 nucleotides for SEQ ID NO: 4).

A fragment of a GRP nucleotide sequence that encodes a biologically active portion of a protein of the invention will encode at least 15, 25, 30, 50, 100, or 150 contiguous amino acids, or up to the total number of amino acids present in a full-length GRP protein of the invention (for example, 173 amino acids for SEQ ID NO: 7). Fragments of a GRP nucleotide sequence that are useful as hybridization probes for PCR primers generally need not encode a biologically active portion of a GRP protein.

Thus, a fragment of a GRP nucleotide sequence may encode a biologically active portion of an GRP protein. Such a fragment may also be used as a hybridization probe or PCR primer using methods disclosed below. A biologically active portion of a GRP protein can be prepared by isolating a portion of one of the GRP coding sequences of the invention, expressing the encoded portion of the GRP protein (e.g., by recombinant expression in vitro), and assessing the activity of the portion of the GRP protein. Nucleic acid molecules that are fragments of a GRP coding sequence comprise at least 15, 20, 50, 75, 100, 150, 200, 250, 300, 350, 400, 450, 500, 550, 600, 650, 700, 750, 800, or 850 nucleotides, or up to the number of nucleotides present in a full-length GRP nucleotide sequence disclosed herein (for example, 865 nucleotides for SEQ ID NO: 6).

Fragments and variants of the disclosed promoter sequences are also encompassed by the present invention. A fragment of an NCE promoter nucleotide sequence may retain the same promoter activity as the native promoter or may possess a promoter activity that is distinguishable from the native promoter. Fragments of a nucleotide sequence that are useful as hybridization probes may or may not retain promoter activity. Such fragments of a nucleotide sequence may range from at least about 20 nucleotides, about 50 nucleotides, about 100 nucleotides, and up to the full-length promoter sequence of the invention.

A biologically active portion of an NCE or GRP promoter can be prepared by isolating a portion of an NCE or GRP promoter sequence of the invention, making a DNA construct by operably linking the portion of the NCE or GRP promoter to a plant reporter gene, transforming a plant or plant cell with the DNA construct and assessing promoter activity by monitoring expression of the reporter gene. Nucleic acid molecules that are fragments of an NCE promoter sequence comprise at least 15, 20, 50, 75, 100, 150, 200, 250, 300, 350, 400, 450, 500, 550, 600, 650, 700, 800, 900, or 1,000 nucleotides; or up to the number of nucleotides present in NCE promoter nucleotide sequence disclosed herein (for example, 1,048 nucleotides for SEQ ID NO: 3). Nucleic acid molecules that are fragments of an GRP promoter sequence comprise at least 15, 20, 50, 75, 100, 150, 200, 250, 300, 350, 400, 450, 500, 550, 600, 650, 700, 800, 900, 1,000 1,100, or 1,200 nucleotides, or up to the number of nucleotides present in NCE promoter nucleotide sequence disclosed herein (for example, 1,267 nucleotides for SEQ ID NO: 8).

By "variants" is intended substantially similar sequences. For nucleotide sequences, conservative variants include those sequences that, because of the degeneracy of the genetic code, encode the amino acid sequence of one of the NCE, AAP, or GRP polypeptides of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but which still encode a NCE or AAP protein of the invention. Generally, variants of a particular nucleotide sequence of the invention will have at least about 40%, 50%, 60%, 65%, 70%, generally at least about 75%, 80%, 85%, preferably at least about 90%, 91%, 92%, 93%, 94%, 95%, 96%, 97%, and more preferably at least about 98%, 99%, or more sequence identity to that particular nucleotide sequence as determined by sequence alignment programs described elsewhere herein using default parameters.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present invention are biologically active, that is they continue to possess the desired biological activity of the native protein, that is, for example, NCE activity or AAP activity as described herein. Such variants may result from, for example, genetic polymorphism or from human manipulation. Biologically active variants of a native NCE, AAP or GRP protein of the invention will have about 90%, 91%, 92%, 93%, 94%, 95%, 96%, 97%, and more preferably at least about 98%, 99%, or more sequence identity to the amino acid sequence for the native protein as determined by sequence alignment programs described elsewhere herein using default parameters. A biologically active variant of a protein of the invention may differ from that protein by as few as 1–15 amino acid residues, as few as 1–10, such as 6–10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants of the NCE, AAP, or GRP proteins can be prepared by mutations in the DNA. Methods for mutagenesis and nucleotide sequence alterations are well known in the art. See, for example, Kunkel (1985) *Proc. Natl. Acad. Sci. USA* 82:488–492; Kunkel et al. (1987) *Methods in Enzymol.* 154:367–382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred.

Thus, the genes and nucleotide sequences of the invention include both the naturally occurring sequences as well as mutant forms. Likewise, the proteins of the invention encompass both naturally occurring proteins as well as variations and modified forms thereof. Such variants will continue to possess the desired NCE, AAP, or GRP activity. Obviously, the mutations that will be made in the DNA encoding the variant must not place the sequence out of reading frame and preferably will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity of NCE can be evaluated by ABA biosynthesis assays (see Tan et al. (1997) *Proc. Natl. Acad. Sci. USA* 94:12235–12240 and Schwartz et al. (1998) *Science* 276:1872; herein incorporated by reference) and the function of AAP can be evaluated by a yeast complementation assay (see, Chen and Bush (1997) *Plant Physiol.* 115:1127–1134 and Rentsch et al. (1996) *Plant Cell* 8:1437–1446; herein incorporated by reference).

Variant proteins also encompass proteins derived from a mutagenic and recombinogenic procedure such as DNA shuffling (see U.S. Pat. Nos. 5,605,793 and 5,837,458). With such a procedure, one or more different NCE, AAP, or GRP coding sequences can be manipulated to create a new NCE, AAP, or GRP possessing the desired properties. Having identified the disclosed NCE, AAP, or GRP genes and the NCE, AAP, or GRP proteins encoded thereby, creation of new NCE, AAP, or GRP genes may be achieved with in vitro recombination of conserved motifs between NCE, AAP, or GRP genes. In this manner, sequence motifs encoding a domain of interest may be shuffled between an NCE, AAP, or GRP gene of the invention and other known NCE, AAP, or GRP genes. Strategies for such DNA shuffling to achieve domain swapping are known in the art. See, for example, Stemmer (1994) *Proc. Natl. Acad. Sci. USA* 91:10747–10751; Stemmer (1994) *Nature* 370:389–391; Moore et al. (1997)*J. Mol. Biol.* 272:336–347; Crameri et al. (1997) *Nature Biotech.* 15:436–438; Crameri et al. (1998) *Nature* 391:288–291.

The nucleotide sequences of the invention can be used to isolate corresponding sequences from other organisms, particularly other plants. In this manner, methods such as PCR, hybridization, and the like can be used to identify such sequences based on their sequence homology to the sequences set forth herein. Sequences isolated based on their sequence identity to the entire NCE, AAP, or GRP sequences set forth herein, or to fragments thereof, are encompassed by the present invention. Such sequences include sequences that are orthologs of the disclosed sequences. By "orthologs" is intended genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species.

In a PCR approach, oligonucleotide primers can be designed for use in PCR reactions to amplify corresponding DNA sequences from cDNA or genomic DNA extracted from any plant organism of interest. Methods for designing PCR primers and PCR cloning are generally known in the art and are disclosed in Sambrook et al. (1989) *Molecular Cloning: A Laboratory Manual* (2nd ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the NCE, AAP, or GRP sequences of the invention. Methods for preparation of probes for hybridization and for construction of cDNA and genomic libraries are generally known in the art and are disclosed in Sambrook et al. (1989) *Molecular Cloning: A Laboratory Manual* (2nd ed., Cold Spring Harbor Laboratory Press, Plainview, N.Y.).

For example, an entire NCE, AAP, or GRP nucleotide disclosed herein, or one or more portions thereof, may be used as a probe capable of specifically hybridizing to corresponding NCE, AAP, or GRP sequences and mRNAs. To achieve specific hybridization under a variety of conditions, such probes include sequences that are unique among NCE, AAP, or GRP sequences and are preferably at least about 10 nucleotides in length, and most preferably at least about 20 nucleotides in length. Such probes may be used to amplify corresponding NCE, AAP, or GRP sequences from a chosen organism by PCR. This technique may be used to isolate additional coding sequences from a desired plant organism or as a diagnostic assay to determine the presence of coding sequences in a plant an organism. Hybridization techniques include hybridization screening of plated DNA libraries (either plaques or colonies; see, for example, Sambrook et al. (1989) *Molecular Cloning: A Laboratory Manual* (2nd ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth et al. (1984) *Anal. Biochem.* 138:267–284: $T_m=81.5°$ C.+16.6 (log M)+0.41 (%GC)−0.61 (% form)−500/L; where M is the molarity of monovalent cations, %GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes,* Part I, Chapter 2 (Elsevier, N.Y.); and Ausubel et al., eds. (1995) *Current Protocols in Molecular Biology,* Chapter 2 (Greene Publishing and Wiley-Interscience, New York). See Sambrook et al. (1989) *Molecular Cloning: A Laboratory Manual (*2nd ed., Cold Spring Harbor Laboratory Press, Plainview, N.Y.).

In general, isolated sequences that have promoter activity and which hybridize under stringent conditions to the NCE promoter sequences disclosed herein, or to fragments thereof, are encompassed by the present invention. Such sequences will be at least about 65% to 70% homologous, about 75% or 80% homologous, and even at least about 85%, 90%, 91%, 92%, 93%, 94%, 95%, 96%, 97%, 98%, 99%, or more homologous with the disclosed sequences. That is, the sequence identity of sequences may range, sharing at least about 40% to 50%, about 60%, 65%, or 70%, and even at least about 75%, 80%, 85%, 90%, 91%, 92%, 93%, 94%, 95%, 96%, 97%, 98%, 99%, or more sequence identity.

In general, isolated sequences that encode an NCE protein and which hybridize under stringent conditions to the NCE coding sequences disclosed herein, or to fragments thereof, are encompassed by the present invention. Such sequences will be at least about 65% to 70% homologous, about 75% or 80% homologous, and even at least about 85%, 90%, 91%, 92%, 93%, 94%, 95%, 96%, 97%, 98%, 99%, or more homologous with the disclosed sequences. That is, the sequence identity of sequences may range, sharing at least about 40% to 50%, about 60%, 65%, or 70%, and even at least about 75%, 80%, 85%, 90%, 91%, 92%, 93%, 94%, 95%, 96%, 97%, 98%, 99%, or more sequence identity.

In general, isolated sequences that encode for an AAP protein and which hybridize under stringent conditions to the AAP sequences disclosed herein, or to fragments thereof, are encompassed by the present invention. Such sequences will be at least about 70% to 75% homologous, about 80% or 85% homologous, and even at least about 90%, 91%, 92%, 93%, 94%, 95%, 96%, 97%, 98%, 99%, or more homologous with the disclosed sequences. That is, the sequence identity of sequences may range, sharing at least about 40% to 50%, about 60%, 65%, or 70%, and even at least about 75%, 80%, 85%, 90%, 91%, 92%, 93%, 94%, 95%, 96%, 97%, 98%, 99%, or more sequence identity.

In general, isolated sequences that have promoter activity and which hybridize under stringent conditions to the GRP promoter sequences disclosed herein, or to fragments thereof, are encompassed by the present invention. Such sequences will be at least about 60% to 65% homologous, about 70%, 75%, or 80% homologous, and even at least about 85%, 90%, 91%, 92%, 93%, 94%, 95%, 96%, 97%, 98%, 99%, or more homologous with the disclosed sequences. That is, the sequence identity of sequences may range, sharing at least about 40% to 50%, about 60%, 65%, or 70%, and even at least about 75%, 80%, 85%, 90%, 91%, 92%, 93%, 94%, 95%, 96%, 97%, 98%, 99%, or more sequence identity.

In general, isolated sequences that encode for a GRP protein and which hybridize under stringent conditions to the GRP sequences disclosed herein, or to fragments thereof, are encompassed by the present invention. Such sequences will be at least about 60% to 65% homologous, about 70%, 75%, or 80% homologous, and even at least about 85%, 90%, 91%, 92%, 93%, 94%, 95%, 96%, 97%, 98%, 99%, or more homologous with the disclosed sequences. That is, the sequence identity of sequences may range, sharing at least about 40% to 50%, about 60%, 65%, or 70%, and even at least about 75%, 80%, 85%, 90%, 91%, 92%, 93%, 94%, 95%, 96%, 97%, 98%, 99%, or more sequence identity.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988) *CABIOS* 4:11–17; the local homology algorithm of Smith et al. (1981) *Adv. Appl. Math.* 2:482; the homology alignment algorithm of Needleman and Wunsch (1970) *J. Mol. Biol.* 48:443–453; the search-for-similarity-method of Pearson and Lipman (1988) *Proc. Natl. Acad. Sci.* 85:2444–2448; the algorithm of Karlin and Altschul (1990) *Proc. Natl. Acad. Sci. USA* 872264, modified as in Karlin and Altschul (1993) *Proc. Natl. Acad. Sci. USA* 90:5873–5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) *Gene* 73:237–244 (1988); Higgins et al. (1989) *CABIOS* 5:151–153; Corpet et al. (1988) *Nucleic Acids Res.* 16:10881–90; Huang et al. (1992) *CABIOS* 8:155–65; and Pearson et al. (1994) *Meth. Mol. Biol.* 24:307–331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215;403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. Alignment may also be performed manually by inspection.

Unless otherwise stated, sequence identity/similarity values provided herein refer to the value obtained using GAP Version 10 using the following parameters: % identity using GAP Weight of 50 and Length Weight of 3; % similarity using Gap Weight of 12 and Length Weight of 4, or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

GAP uses the algorithm of Needleman and Wunsch (1970) *J. Mol. Biol.* 48: 443–453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65, or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of I and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman et al. (1970) *J. Mol. Biol.* 48:443. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The use of the term "DNA constructs" herein is not intended to limit the present invention to nucleotide constructs comprising DNA. Those of ordinary skill in the art will recognize that nucleotide constructs, particularly polynucleotides and oligonucleotides, comprised of ribonucleotides and combinations of ribonucleotides and deoxyribonucleotides may also be employed in the methods disclosed herein. Thus, the DNA constructs of the present invention encompass all nucleotide constructs which can be employed in the methods of the present invention for transforming plants including, but not limited to, those comprised of deoxyribonucleotides, ribonucleotides and combinations thereof. Such deoxyribonucleotides and ribonucleotides include both naturally occurring molecules and synthetic analogues. The DNA constructs of the invention also encompass all forms of nucleotide constructs including, but not limited to, single-stranded forms, double-stranded forms, hairpins, stem-and-loop structures and the like.

Furthermore, it is recognized that the methods of the invention may employ a DNA construct that is capable of directing, in a transformed plant, the expression of at least one protein, or at least one RNA, such as, for example, an rRNA, a tRNA and an antisense RNA that is complementary to at least a portion of an mRNA. Typically such a DNA construct is comprised of a coding sequence for a protein or an RNA operably linked to 5' and 3' transcriptional regulatory regions. Alternatively, it is also recognized that the methods of the invention may employ a DNA construct that is not capable of directing, in a transformed plant, the expression of a protein or RNA.

The DNA constructs of the invention also encompass nucleotide constructs, that may be employed in methods for altering or mutating a genomic nucleotide sequence in an organism, including, but not limited to, chimeric vectors, chimeric mutational vectors, chimeric repair vectors, mixed-duplex oligonucleotides, self-complementary chimeric oligonucleotides and recombinogenic oligonucleobases. Such nucleotide constructs and methods of use, such as, for example, chimeraplasty, are known in the art. Chimeraplasty involves the use of such nucleotide constructs to introduce site-specific changes into the sequence of genomic DNA within an organism. See, U.S. Pat. Nos. 5,565,350; 5,731,181; 5,756,325; 5,760,012; 5,795,972; and 5,871,984; all of which are herein incorporated by reference. See also, WO 98/49350, WO 99/07865, WO 99/25821 and Beetham et al. (1999) *Proc. Natl. Acad. Sci. USA* 96:8774–8778; herein incorporated by reference.

The NCE, AAP, or GRP nucleotide sequences of the invention are provided in expression cassettes for expression in the plant of interest. The cassette will include 5' and 3'-regulatory sequences operably linked to an NCE, AAP, or GRP coding sequence of the invention. Alternatively or additionally, the cassette will include an NCE or GPR promoter sequence of the invention and a 3'-regulatory sequence operably linked to a coding sequence. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the coding sequence to be under the transcriptional regulation of the regulatory regions. The expression cassette may additionally contain selectable marker genes.

The expression cassette will include in the 5'-3' direction of transcription, a transcriptional and translational initiation region, an NCE, AAP, or GRP coding sequence of the invention, and a transcriptional and translational termination region functional in plants. The transcriptional initiation region, the promoter, may be native or analogous or foreign or heterologous to the plant host. Additionally, the promoter may be the natural sequence or alternatively a synthetic sequence. By "foreign" is intended that the transcriptional initiation region is not found in the native plant into which the transcriptional initiation region is introduced. As used herein, a chimeric gene comprises a coding sequence operably linked to a transcription initiation region that is heterologous to the coding sequence, or any combination of a promoter with a coding sequence that is not identical to the structure of a native, unmodified gene.

While it may be preferable to express the sequences using heterologous promoters, the native promoter sequences may be used such as, for example, the NCE and GRP promoters of the invention. Such constructs would change expression levels of NCE, AAP, or GRP in the plant or plant cell. Thus, the phenotype of the plant or plant cell is altered.

The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. (1989) *Nuc. Acids Res.* 17:7891–7903; and Joshi et al. (1987) *Nuc. Acid Res.* 15:9627–9639.

Where appropriate, the gene(s) may be optimized for increased expression in the transformed plant. That is, the genes can be synthesized using plant-preferred codons for improved expression. See, for example, Campbell and Gowri (1990) *Plant Physiol.* 92:1–11 for a discussion of host-preferred codon usage. Methods are available in the art for synthesizing plant-preferred genes. See, for example, U.S. Pat. Nos. 5,380,831, 5,436,391, and Murray et al. (1989) *Nucleic Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *PNAS USA* 86:6126–6130); potyvirus leaders, for example, TEV leader (Tobacco Etch Virus) (Allison et al. (1986); MDMV leader (Maize Dwarf Mosaic Virus); *Virology* 154:9–20), and human immunoglobulin heavy-chain binding protein (BiP), (Macejak et al. (1991) *Nature* 353:90–94); untranslated leader from the coat protein mRNA of alfalfa mosaic virus (AMV RNA 4) (Jobling et al. (1987) *Nature* 325:622–625); tobacco mosaic virus leader (TMV) (Gallie et al. (1989) in *Molecular Biology of RNA*, ed. Cech (Liss, N.Y.), pp. 237–256); and maize chlorotic mottle virus leader (MCMV) (Lommel et al. (1991) *Virology* 81:382–385). See also, Della-Cioppa et al. (1987) *Plant Physiol.* 84:965–968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the desired outcome. The nucleic acids can be combined with constitutive, tissue-preferred, or other promoters for expression in plants.

Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810–812); rice actin (McElroy et al. (1990) *Plant Cell* 2:163–171); ubiquitin (Christensen et al. (1989) *Plant Mol. Biol.* 12:619–632 and Christensen et al. (1992) *Plant Mol. Biol.* 18:675–689); pEMU (Last et al. (1991) *Theor. Appl. Genet.* 81:581–588); MAS (Velten et al. (1984) *EMBO J.* 3:2723–2730); ALS promoter (U.S. application Ser. No. 08/409,297), and the like. Other constitutive promoters include, for example, U.S. Pat. Nos. 5,608,149; 5,608,144; 5,604,121; 5,569,597; 5,466,785; 5,399,680; 5,268,463; and 5,608,142.

Generally, it will be beneficial to express the gene from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245–254; Uknes et al. (1992) *Plant Cell* 4:645–656; and Van Loon (1985) *Plant Mol. Virol.* 4:111–116. See also the copending applications entitled "Inducible Maize Promoters", U.S. Application Serial No. 60/076,100, filed Feb. 26, 1998, and U.S. Application Serial No. 60/079,648, filed Mar. 27, 1998, both of which are herein incorporated by reference.

Of interest are promoters that are expressed locally at or near the site of pathogen infection. See, for example, Marineau et al. (1987) *Plant Mol. Biol.* 9:335–342; Matton et al. (1989) *Molecular Plant-Microbe Interactions* 2:325–331; Somsisch et al. (1986) *Proc. Natl. Acad. Sci. USA* 83:2427–2430; Somsisch et al. (1988) *Mol. Gen. Genet.* 2:93–98; and Yang (1996) *Proc. Natl. Acad. Sci. USA* 93:14972–14977. See also, Chen et al. (1996) *Plant J.* 10:955–966; Zhang et al. (1994) *Proc. Natl. Acad. Sci. USA* 91:2507–2511; Warner et al. (1993) *Plant J.* 3:191–201; Siebertz et al. (1989) *Plant Cell* 1:961–968; U.S. Pat. No. 5,750,386 (nematode-inducible); and the references cited therein. Of particular interest is the inducible promoter for the maize PRms gene, whose expression is induced by the pathogen Fusarium moniliforme (see, for example, Cordero et al. (1992) *Physiol. Mol. Plant Path.* 41:189–200).

Additionally, as pathogens find entry into plants through wounds or insect damage, a wound-inducible promoter may be used in the constructions of the invention. Such wound-inducible promoters include potato proteinase inhibitor (pin II) gene (Ryan (1990) *Ann. Rev. Phytopath.* 28:425–449; Duan et al. (1996) *Nature Biotechnology* 14:494–498); wun1 and wun2, U.S. Pat. No. 5,428,148; win1 and win2 (Stanford et al. (1989) *Mol. Gen. Genet.* 215:200–208); systemin (McGurl et al. (1992) *Science* 225:1570–1573); WIP1 (Rohmeier et al. (1993) *Plant Mol. Biol.* 22:783–792; Eckelkamp et al. (1993) *FEBS Letters* 323:73–76); MPI gene (Corderok et al. (1994) *Plant J.* 6(2):141–150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421–10425 and McNellis et al. (1998) *Plant J.* 14(2):247–257) and tetracycline-inducible and tetracycline-repressible promoters (see, for example, Gatz et al. (1991) *Mol. Gen. Genet.* 227:229–237, and U.S. Pat. Nos. 5,814,618 and 5,789,156), herein incorporated by reference.

Tissue-preferred promoters can be utilized to express the nucleotide sequences of the invention within a particular plant tissue. Leaf-preferred promoters include, Yamamoto et al. (1997) *Plant J.* 12(2):255–265; Kawamata et al. (1997) *Plant Cell Physiol.* 38(7):792–803; Hansen et al. (1997) *Mol. Gen. Genet.* 254(3):337–343; Russell et al. (1997) *Transgenic Res.* 6(2):157–168; Rinehart et al. (1996) *Plant Physiol.* 112(3):1331–1341; Van Camp et al. (1996) *Plant Physiol.* 112(2):525–535; Canevascini et al. (1996) *Plant Physiol.* 112(2):513–524; Yamamoto et al. (1994) *Plant Cell Physiol.* 35(5):773–778; Lam (1994) *Results Probl. Cell Differ.* 20:181–196; Orozco et al. (1993) *Plant Mol. Biol.* 23(6):1129–1138; Matsuoka et al. (1993) *Proc. Natl. Acad. Sci. USA* 90(20):9586–9590; and Guevara-Garcia et al. (1993) *Plant J.* 4(3):495–505.

Root-preferred promoters are known and can be selected from the many available from the literature or isolated de novo from various compatible species. See, for example, Hire et al. (1992) *Plant Mol. Biol.* 20(2): 207–218 (soybean root-preferred glutamine synthetase gene); Keller and Baumgartner (1991) *Plant Cell* 3(10):1051–1061 (root-specific control element in the GRP 1.8 gene of French bean); Sanger et al. (1990) *Plant Mol. Biol.* 14(3):433–443 (root-specific promoter of the mannopine synthase (MAS) gene of *Agrobacterium tumefaciens*); and Miao et al. (1991) *Plant Cell* 3(1):11–22 (full-length cDNA clone encoding cytosolic glutamine synthetase (GS), which is expressed in roots and root nodules of soybean). See also Bogusz et al. (1990) *Plant Cell* 2(7):633–641, where two root-preferred promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus,* and in both instances root-specific promoter activity was preserved. Leach and Aoyagi (1991) describe their analysis of the promoters of the highly expressed rolC and rolD root-inducing genes of *Agrobacterium rhizogenes* (see *Plant Science* (Limerick) 79(1):69–76). They concluded that enhancer and tissue-preferred DNA determinants are dissociated in those promoters. Teeri et al. (1989) used gene fusion to lacZ to show that the Agrobacterium T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2):343–350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4):759–772); and rolB promoter (Capana et al. (1994) *Plant Mol. Biol.* 25(4):681–691. See also U.S. Pat. Nos. 5,837,876; 5,750,386; 5,633,363; 5,459,252; 5,401, 836; 5,110,732; and 5,023,179.

"Seed-preferred" promoters include both "seed-preferred" promoters (those promoters active during seed development such as promoters of seed storage proteins) as well as "seed-germinating" promoters (those promoters active during seed germination). See Thompson et al. (1989) *BioEssays* 10:108, herein incorporated by reference. Such seed-preferred promoters include, but are not limited to, Cim1 (cytokinin-induced message); cZ19B1 (maize 19 kDa zein); and celA (cellulose synthase). Gama-zein is a preferred endosperm-specific promoter. Glob-1 is a preferred embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc.

Where low-level expression is desired, weak promoters will be used. Generally, by "weak promoter" is intended a promoter that drives expression of a coding sequence at a low level. By low level is intended at levels of about 1/1000 transcripts to about 1/100,000 transcripts to about 1/500,000 transcripts. Alternatively, it is recognized that weak promoters also encompass promoters that are expressed in only a few cells and not in others to give a total low level of expression. Where a promoter is expressed at unacceptably high levels, portions of the promoter sequence can be deleted or modified to decrease expression levels.

Such weak constitutive promoters include, for example, the core promoter of the Rsyn7 promoter (WO 99/43838 and U.S. Pat. No. 6,072,050), the core 35S CaMV promoter, and the like. Other constitutive promoters include, for example, U.S. Pat. Nos. 5,608,149; 5,608,144; 5,604,121; 5,569,597; 5,466,785; 5,399,680; 5,268,463; and 5,608,142. See also, copending application entitled "Constitutive Maize Promoters", U.S. Application Serial No. 60/076,075, filed Feb. 26, 1998, and herein incorporated by reference.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) *Curr. Opin. Biotech.* 3:506–511; Christopherson et al. (1992) *Proc. Natl. Acad. Sci. USA* 89:6314–6318; Yao et al. (1992) *Cell* 71:63–72; Reznikoff (1992) *Mol. Microbiol.* 6:2419–2422; Barkley et al. (1980) in *The Operon,* pp. 177–220; Hu et al.(1987) *Cell* 48:555–566; Brown et al. (1987) *Cell* 49:603–612; Figge et al. (1988) *Cell* 52:713–722; Deuschle et al. (1989) *Proc. Natl. Acad. Aci. USA* 86:5400–5404; Fuerst et al. (1989) *Proc. Natl. Acad. Sci. USA* 86:2549–2553; Deuschle et al. (1990) *Science* 248:480–483; Gossen (1993) Ph.D. Thesis, University of Heidelberg; Reines et al.(1993) *Proc. Natl. Acad. Sci. USA* 90:1917–1921; Labow et al. (1990) *Mol. Cell. Biol.*

;10:3343–3356; Zambretti et al. (1992) *Proc. Natl. Acad. Sci. USA* 89:3952–3956; Baim et al. (1991) *Proc. Natl. Acad. Sci. USA* 88:5072–5076; Wyborski et al. (1991) *Nuc. Acids Res.* 19:4647–4653; Hillenand-Wissman (1989) *Topics Mol. Struc. Biol.* 10:143–162; Degenkolb et al. (1991) *Antimicrob. Agents Chemother.* 35:1591–1595; Kleinschnidt et al. (1988) *Biochemistry* 27:1094–1104; Bonin (1993) Ph.D. Thesis, University of Heidelberg; Gossen et al. (1992) *Proc. Natl. Acad. Sci. USA* 89:5547–5551; Oliva et al. (1992) *Antimicrob. Agents Chemother.* 36:913–919; Hlavka et al. (1985) *Handbook of Experimental Pharmacology*, Vol. 78 (Springer-Verlag, Berlin); Gill et al. (1988) *Nature* 334:721–724. Such disclosures are herein incorporated by reference.

The above list of selectable marker genes is not meant to be limiting. Any selectable marker gene can be used in the present invention.

In some embodiments of the invention, the nucleic acids of interest are targeted to the chloroplast for expression. In this manner, where the nucleic acid of interest is not directly inserted into the chloroplast, the expression cassette will additionally contain a nucleic acid encoding a transit peptide to direct the nucleic acid of interest to the chloroplasts. Such transit peptides are known in the art. See, for example, Von Heijne et al. (1991) *Plant Mol. Biol. Rep.* 9:104–126; Clark et al. (1989) *J. Biol. Chem.* 264:17544–17550; Della-Cioppa et al. (1987) *Plant Physiol.* 84:965–968; Romer et al. (1993) *Biochem. Biophys. Res. Commun.* 196:1414–1421; and Shah et al. (1986) *Science* 233:478–481.

Chloroplast-targeting sequences are known in the art and include the chloroplast small subunit of ribulose-1,5-bisphosphate carboxylase (Rubisco) (de Castro Silva Filho et al. (1996) *Plant Mol. Biol.* 30:769–780; Schnell et al. (1991) *J. Biol. Chem.* 266(5):3335–3342); 5-(enolpyruvyl) shikimate-3-phosphate synthase (EPSPS) (Archer et al. (1990) *J. Bioenerg. Biomemb.* 22(6):789–810); tryptophan synthase (Zhao et al. (1995) *J. Biol. Chem.* 270(11): 6081–6087); plastocyanin (Lawrence et al. (1997) *J. Biol. Chem.* 272(33):20357–20363); chorismate synthase (Schmidt et al. (1993) *J. Biol. Chem.* 268(36): 27447–27457); and the light harvesting chlorophyll a/b binding protein (LHBP) (Lamppa et al. (1988) *J. Biol. Chem.* 263:14996–14999). See also Von Heijne et al. (1991) *Plant Mol. Biol. Rep.* 9:104–126; Clark et al. (1989) *J. Biol. Chem.* 264:17544–17550; Della-Cioppa et al. (1987) *Plant Physiol.* 84:965–968; Romer et al. (1993) *Biochem. Biophys. Res. Commun.* 196:1414–1421; and Shah et al. (1986) *Science* 233:478–481.

Methods for transformation of chloroplasts are known in the art. See, for example, Svab et al. (1990) *Proc. Natl. Acad. Sci. USA* 87:8526–8530; Svab and Maliga (1993) *Proc. Natl. Acad. Sci. USA* 90:913–917; Svab and Maliga (1993) *EMBO J.* 12:601–606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301–7305.

The nucleic acids of interest to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606, Agrobacterium-mediated transformation (Townsend et al., U.S. Pat. No. 5,563,055; Zhao et al., U.S. Pat. No. 5,981,840), direct gene transfer (Paszkowski et al. (1984) *EMBO J.* 3:2717–2722), and ballistic particle acceleration (see, for example, Sanford et al., U.S. Pat. No. 4,945,050; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); and McCabe et al. (1988) *Biotechnology* 6:923–926). Also see Weissinger et al. (1988) *Ann. Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) *In Vitro Cell Dev. Biol.* 27P:175–182 (soybean); Singh et al. (1998) *Theor. Appl. Genet.* 96:319–324 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440–444 (maize); Fromm et al. (1990) *Biotechnology* 8:833–839 (maize); Hooykaas-Van Slogteren et al. (1984) *Nature* (London) 311:763–764; Bytebier et al. (1987) *Proc. Natl. Acad. Sci. USA* 84:5345–5349 (Liliaceae); De Wet et al. (1985) in *The Experimental Manipulation of Ovule Tissues*, ed. Chapman et al. (Longman, N.Y.), pp. 197–209 (pollen); Kaeppler et al. (1990) *Plant Cell Reports* 9:415–418 and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (maize via *Agrobacterium tumefaciens*); all of which are herein incorporated by reference.

The cells that have been transformed may be grown into plants in accordance with conventional ways. See, for example, McCormick et al. (1986) *Plant Cell Reports* 5:81–84. These plants may then be grown, and either pollinated with the same transformed strain or different strains, and the resulting hybrid having constitutive expression of the desired phenotypic characteristic identified. Two or more generations may be grown to ensure that constitutive expression of the desired phenotypic characteristic is stably maintained and inherited and then seeds harvested to ensure constitutive expression of the desired phenotypic characteristic has been achieved.

The promoter nucleotide sequences and methods disclosed herein are useful for regulating the expression of any heterologous nucleotide sequence in a host plant in order to vary the phenotype of a plant. The NCE promoter sequences of the invention can be used to regulate the expression of any heterologous nucleotide sequence in a inducible manner. That is the NCE promoter nucleotide sequence directs increased transcription of the heterologous nucleotide sequence when the inducing agent or stimulus impacts a plant or a plant cell. Such stimuli include a pathogen, wounding, $H_2O_2$, jasmonic acid, methyl jasmonate, salicylic acid, methylsalicylic acid, oxalic acid and expression of a gene encoding oxalic acid oxidase. The GRP promoter can be used drive the stem-preferred expression of any heterologous nucleotide sequence. This the GRP promoter directs increased transcription of the heterologous nucleotide sequence preferentially in plant stems.

Various changes in phenotype are of interest including modifying the fatty acid composition in a plant, modulating the amino acid content of a plant, modulating a plant's pathogen defense mechanism, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Preferred genes of interest include those involved in insect and disease resistance.

Insect resistance genes may encode resistance to pests that have great yield drag such as rootworm, cutworm, European Corn Borer, and the like. Such genes include, for example, *Bacillus thuringiensis* toxic protein genes (U.S. Pat. Nos. 5,366,892; 5,747,450; 5,736,514; 5,723,756; 5,593,881; and Geiser et al. (1986) *Gene* 48:109); lectins (Van Damme et al. (1994) *Plant Mol. Biol.* 24:825); and the like.

Genes encoding disease resistance traits include detoxification genes, such as against fumonosin (U.S. application Ser. No. 08/484,815, filed Jun. 7, 1995); avirulence (avr) and disease resistance (R) genes (Jones et al. (1994) *Science* 266:789; Martin et al. (1993) *Science* 262:1432; and Mindrinos et al. (1994) *Cell* 78:1089); and the like.

By "antisense DNA nucleotide sequence" is intended a sequence that is in inverse orientation to the 5' to 3' normal orientation of that nucleotide sequence. When delivered into a plant cell, the antisense DNA sequence prevents normal expression of the DNA nucleotide sequence for the native gene. The antisense nucleotide sequence encodes an RNA transcript that is complementary to and capable of hybridizing to the endogenous messenger RNA (mRNA) produced by transcription of the DNA nucleotide sequence for the native gene. Expression of the antisense transcript RNA interferes with expression of the corresponding mRNA and hence disrupts production of the native protein.

It is recognized that with these nucleotide sequences, antisense constructions, complementary to at least a portion of the messenger RNA (mRNA) for the NCE, AAP, or GRP sequences can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, preferably 80%, more preferably 85% sequence identity to the corresponding antisensed sequences may be used. Furthermore, portions of the antisense nucleotides may be used to disrupt the expression of the target gene. Generally, sequences of at least 50 nucleotides, 100 nucleotides, 200 nucleotides, or greater may be used.

The nucleotide sequences of the present invention may also be used in the sense orientation to suppress the expression of endogenous genes in plants. Methods for suppressing gene expression in plants using nucleotide sequences in the sense orientation, also referred to as cosuppression methods, are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, preferably greater than about 65% sequence identity, more preferably greater than about 85% sequence identity, most preferably greater than about 95% sequence identity. See, U.S. Pat. Nos. 5,283,184 and 5,034,323; herein incorporated by reference.

The present invention may be used for transformation of any plant species, including, but not limited to, corn (*Zea mays*), Brassica sp. (e.g., *B. napus, B. rapa, B. juncea*), particularly those Brassica species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea spp.*), coconut (*Cocos nucifera*), pineapple (*Ananas comosus*), citrus trees (*Citrus spp.*), cocoa (*Theobroma cacao*), tea (*Camellia sinensis*), banana (*Musa spp.*), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum spp.*), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (Lathyrus spp.), and members of the genus Cucumis such as cucumber (*C. sativus*), cantaloupe (*C. cantalupensis*), and musk melon (*C. melo*). Ornamentals include azalea (Rhododendron spp.), hydrangea (*Macrophylla hydrangea*), hibiscus (*Hibiscus rosasanensis*), roses (Rosa spp.), tulips (Tulipa spp.), daffodils (Narcissus spp.), petunias (*Petunia hybrida*), carnation (*Dianthus caryophyllus*), poinsettia (*Euphorbia pulcherrima*), and chrysanthemum. Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Preferably, plants of the present invention are crop plants (for example, corn, alfalfa, sunflower, Brassica, soybean, cotton, safflower, peanut, sorghum, wheat, millet, tobacco, etc.), more preferably corn and soybean plants, yet more preferably corn plants.

Plants of particular interest include grain plants that provide seeds of interest, oil-seed plants, and leguminous plants. Seeds of interest include grain seeds, such as corn, wheat, barley, rice, sorghum, rye, etc. Oil seed plants include cotton, soybean, safflower, sunflower, Brassica, maize, peanut, palm, coconut, etc. Leguminous plants include beans and peas. Beans include guar, locust bean, fenugreek, soybean, garden beans, cowpea, mungbean, lima bean, fava bean, lentils, chickpea, etc.

The invention is drawn to compositions and methods for inducing resistance in a plant to plant pests. Accordingly, the compositions and methods are also useful in protecting plants against fungal pathogens, viruses, nematodes, insects and the like.

By "disease resistance" is intended that the plants avoid the disease symptoms that are the outcome of plant-pathogen interactions. That is, pathogens are prevented from causing plant diseases and the associated disease symptoms, or alternatively, the disease symptoms caused by the pathogen is minimized or lessened. The methods of the invention can be utilized to protect plants from disease, particularly those diseases that are caused by plant pathogens.

Pathogens of the invention include, but are not limited to, viruses or viroids, bacteria, insects, nematodes, fungi, parasitic plants, and the like. Viruses include any plant virus, for example, tobacco or cucumber mosaic virus, ringspot virus, necrosis virus, maize dwarf mosaic virus, etc. Specific fungal and viral pathogens for the major crops include: Soybeans: *Phytophthora megasperma* fsp. *glycinea*, *Macrophomina phaseolina*, *Rhizoctonia solani*, *Sclerotinia sclerotiorum*, *Fusarium oxysporum*, *Diaporthe phaseolorum* var. *sojae* (*Phomopsis sojae*), *Diaporthe phaseolorum* var. *caulivora*, *Sclerotium rolfsii*, *Cercospora kikuchii*, *Cercospora sojina*, *Peronospora manshurica*, *Colletotrichum dematium* (*Colletotichum truncatum*), *Corynespora cassiicola*, *Septoria glycines*, *Phyllosticta sojicola*, *Alternaria alternata*, *Pseudomonas syringae* p.v. *glycinea*, *Xanthomonas campestris* p.v. *phaseoli*, *Microsphaera diffusa*, *Fusarium semitectum*, *Phialophora gregata*, Soybean mosaic virus, *Glomerella glycines*, Tobacco Ring spot virus, Tobacco Streak virus, *Phakopsora pachyrhizi*, *Pythium aphanidermatum*, *Pythium ultimum*, *Pythium debaryanum*, Tomato spotted wilt virus, *Heterodera glycines Fusarium solani*; Canola: *Albugo candida*, *Alternaria brassicae*, *Leptosphaeria maculans*, *Rhizoctonia solani*, *Sclerotinia sclerotiorum*, *Mycosphaerella brassiccola*, *Pythium ultimum*, *Peronospora parasitica*, *Fusarium roseum*, *Alternaria alternata*; Alfalfa: *Clavibater michiganese* subsp. *insidiosum*, *Pythium ultimum*, *Pythium irregulare*, *Pythium splendens*, *Pythium debaryanum*, *Pythium aphanidermatum*, *Phytophthora megasperma*, *Peronospora trifoliorum*, *Phoma medicaginis* var. *medicaginis*, *Cercospora medicaginis*, *Pseudopeziza medicaginis*, *Leptotrochila medicaginis*, Fusarium, *Xanthomonas campestris* p.v. *alfalfae*, *Aphanomyces euteiches*, *Stemphylium herbarum*, *Stemphylium alfalfae*; Wheat: *Pseudomonas syringae* p.v. *atrofaciens*, *Urocystis agropyri*, *Xanthomonas campestris* p.v. *translucens*, *Pseudomonas syringae* p.v. *syringae*, *Alternaria alternata*, *Cladosporium herbarum*, *Fusarium graminearum*, *Fusarium avenaceum*, *Fusarium culmorum*, *Ustilago tritici*, *Ascochyta tritici*, *Cephalosporium gramineum*, *Collotetrichum graminicola*, *Erysiphe graminis* f.sp. *tritici*, *Puccinia graminis* f.sp. *tritici*, *Puccinia recondita* f.sp. *tritici*, *Puccinia striiformis*, *Pyrenophora tritici-repentis*, *Septoria nodorum*, *Septoria tritici*, *Septoria avenae*, *Pseudocercosporella herpotrichoides*, *Rhizoctonia solani*, *Rhizoctonia cerealis*, *Gaeumannomyces graminis* var. *tritici*, *Pythium aphanidermatum*, *Pythium arrhenomanes*, *Pythium ultimum*, *Bipolaris sorokiniana*, Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, *Claviceps purpurea*, *Tilletia tritici*, *Tilletia laevis*, *Ustilago tritici*, *Tilletia indica*, *Rhizoctonia solani*, *Pythium arrhenomannes*, *Pythium gramicola*, *Pythium aphanidermatum*, High Plains Virus, European wheat striate virus; Sunflower: *Plasmophora halstedii*, *Sclerotinia sclerotiorum*, Aster Yellows, *Septoria helianthi*, *Phomopsis helianthi*, *Alternaria helianthi*, *Alternaria zinniae*, *Botrytis cinerea*, *Phoma macdonaldii*, *Macrophomina phaseolina*, *Erysiphe cichoracearum*, *Rhizopus oryzae*, *Rhizopus arrhizus*, *Rhizopus stolonifer*, *Puccinia helianthi*, *Verticillium dahliae*, *Erwinia carotovorum* pv. *carotovora*, *Cephalosporium acremonium*, *Phytophthora cryptogea*, *Albugo tragopogonis*; Corn: *Fusarium moniliforme* var. *subglutinans*, *Erwinia stewartii*, *Fusarium moniliforme*, *Gibberella zeae* (*Fusarium graminearum*), *Stenocarpella maydi* (*Diplodia maydis*), *Pythium irregulare*, *Pythium debaryanum*, *Pythium graminicola*, *Pythium splendens*, *Pythium ultimum*, *Pythium aphanidermatum*, *Aspergillus flavus*, *Bipolaris maydis* O, T (*Cochliobolus heterostrophus*), *Helminthosporium carbonum* I, II & III (*Cochliobolus carbonum*), *Exserohilum turcicum* I, II & III, *Helminthosporium pedicellatum*, *Physoderma maydis*, *Phyllosticta maydis*, *Kabatiella-maydis*, *Cercospora sorghi*, *Ustilago maydis*, *Puccinia sorghi*, *Puccinia polysora*, *Macrophomina phaseolina*, *Penicillium oxalicum*, *Nigrospora oryzae*, *Cladosporium herbarum*, *Curvularia lunata*, *Curvularia inaequalis*, *Curvularia pallescens*, *Clavibacter michiganense* subsp. *nebraskense*, *Trichoderma viride*, Maize Dwarf Mosaic Virus A & B, Wheat Streak Mosaic Virus, Maize Chlorotic Dwarf Virus, *Claviceps sorghi*, *Pseudonomas avenae*, *Erwinia chrysanthemi* pv. *zea*, *Erwinia carotovora*, Corn stunt spiroplasma, *Diplodia macrospora*, *Sclerophthora macrospora*, *Peronosclerospora sorghi*, *Peronosclerospora philippinensis*, *Peronosclerospora maydis*, *Peronoscierospora sacchari*, *Sphacelotheca reiliana*, *Physopella zeae*, *Cephalosporium maydis*, *Cephalosporium acremonium*, Maize Chlorotic Mottle Virus, High Plains Virus, Maize Mosaic Virus, Maize Rayado Fino Virus, Maize Streak Virus, Maize Stripe Virus, Maize Rough Dwarf Virus; Sorghum: *Exserohilum turcicum*, *Colletotrichum graminicola* (*Glomerella graminicola*), *Cercospora sorghi*, *Gloeocercospora sorghi*, *Ascochyta sorghina*, *Pseudomonas syringae* p.v. *syringae*, *Xanthomonas campestris* p.v. *holcicola*, *Pseudomonas andropogonis*, *Puccinia purpurea*, *Macrophomina phaseolina*, *Perconia circinata*, *Fusarium moniliforme*, *Alternaria alternata*, *Bipolaris sorghicola*, *Helminthospo-*

*rium sorghicola, Curvularia lunata, Phoma insidiosa, Pseudomonas avenae (Pseudomonas alboprecipitans), Ramulispora sorghi, Ramulispora sorghicola, Phyllachara sacchari, Sporisorium reilianum (Sphacelotheca reiliana), Sphacelotheca cruenta, Sporisorium sorghi,* Sugarcane mosaic H, Maize Dwarf Mosaic Virus A & B, *Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola,* etc.

Nematodes include parasitic nematodes such as root knot, cyst, lesion, and reniform nematodes, etc.

Parasitic plants include, but are not limited to, true and dwarf mistletoes, witchweeds (*Striga* spp.), *Orobanche cumana* and other parasitic *Orobanche* spp.

Insect pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera. Insect pests of the invention for the major crops include: Maize: *Ostrinia nubilalis,* European corn borer; *Agrotis ipsilon,* black cutworm; *Helicoverpa zea,* corn earworm; *Spodoptera frugiperda,* fall armyworm; *Diatraea grandiosella,* southwestern corn borer; *Elasmopalpus lignosellus,* lesser cornstalk borer; *Diatraea saccharalis,* surgarcane borer; *Diabrotica virgifera,* western corn rootworm; *Diabrotica longicornis barberi,* northern corn rootworm; *Diabrotica undecimpunctata howardi,* southern corn rootworm; *Melanotus* spp., wireworms; *Cyclocephala borealis,* northern masked chafer (*white grub*); *Cyclocephala immaculata,* southern masked chafer (white grub); *Popillia japonica,* Japanese beetle; *Chaetocnema pulicaria,* corn flea beetle; *Sphenophorus maidis,* maize billbug; *Rhopalosiphum maidis,* corn leaf aphid; *Anuraphis maidiradicis,* corn root aphid; *Blissus leucopterus leucopterus,* chinch bug; *Melanoplus femurrubrum,* redlegged grasshopper; *Melanoplus sanguinipes,* migratory grasshopper; *Hylemya platura,* seedcorn maggot; *Agromyza parvicornis,* corn blot leafminer; *Anaphothrips obscrurus,* grass thrips; *Solenopsis milesta,* thief ant; *Tetranychus urticae,* twospotted spider mite; Sorghum: *Chilo partellus,* sorghum borer; *Spodoptera frugiperda,* fall armyworm; *Helicoverpa zea,* corn earworm; *Elasmopalpus lignosellus,* lesser cornstalk borer; *Feltia subterranea,* granulate cutworm; *Phyllophaga crinita,* white grub; *Eleodes, Conoderus,* and *Aeolus* spp., wireworms; *Oulema melanopus,* cereal leaf beetle; *Chaetocnema pulicaria,* corn flea beetle; *Sphenophorus maidis,* maize billbug; *Rhopalosiphum maidis;* corn leaf aphid; *Sipha flava,* yellow sugarcane aphid; *Blissus leucopterus leucopterus,* chinch bug; *Contarinia sorghicola,* sorghum midge; *Tetranychus cinnabarinus,* carmine spider mite; *Tetranychus urticae,* twospotted spider mite; Wheat: *Pseudaletia unipunctata,* army worm; *Spodoptera frugiperda,* fall armyworm; *Elasmopalpus lignosellus,* lesser cornstalk borer; *Agrotis orthogonia,* western cutworm; *Elasmopalpus lignosellus,* lesser cornstalk borer; *Oulema melanopus,* cereal leaf beetle; *Hypera punctata,* clover leaf weevil; *Diabrotica undecimpunctata howardi,* southern corn rootworm; Russian wheat aphid; *Schizaphis graminum,* greenbug; *Macrosiphum avenae,* English grain aphid; *Melanoplus femurrubrum,* redlegged grasshopper; *Melanoplus differentialis,* differential grasshopper; *Melanoplus sanguinipes,* migratory grasshopper; *Mayetiola destructor,* Hessian fly; *Sitodiplosis mosellana,* wheat midge; *Meromyza americana,* wheat stem maggot; *Hylemya coarctata,* wheat bulb fly; *Frankliniella fusca,* tobacco thrips; *Cephus cinctus,* wheat stem sawfly; *Aceria tulipae,* wheat curl mite; Sunflower: *Suleima helianthana,* sunflower bud moth; *Homoeosoma electellum,* sunflower moth; *zygogramma exclamationis,* sunflower beetle; *Bothyrus gibbosus,* carrot beetle; *Neolasioptera murtfeldtiana,* sunflower seed midge; Cotton: *Heliothis virescens,* cotton budworm; *Helicoverpa zea,* cotton bollworm; *Spodoptera exigua,* beet armyworm; *Pectinophora gossypiella,* pink bollworm; *Anthonomus grandis grandis,* boll weevil; *Aphis gossypii,* cotton aphid; *Pseudatomoscelis seriatus,* cotton fleahopper; *Trialeurodes abutilonea,* bandedwinged whitefly; *Lygus lineolaris,* tarnished plant bug; *Melanoplus femurrubrum,* redlegged grasshopper; *Melanoplus differentialis,* differential grasshopper; *Thrips tabaci,* onion thrips; *Franklinkiella fusca,* tobacco thrips; *Tetranychus cinnabarinus,* carmine spider mite; *Tetranychus urticae,* twospotted spider mite; Rice: *Diatraea saccharalis,* sugarcane borer; *Spodoptera frugiperda,* fall armyworm; *Helicoverpa zea,* corn earworm; *Colaspis brunnea,* grape colaspis; *Lissorhoptrus oryzophilus,* rice water weevil; *Sitophilus oryzae,* rice weevil; *Nephotettix nigropictus,* rice leafhopper; *Blissus leucopterus leucopterus,* chinch bug; *Acrosternum hilare,* green stink bug; Soybean: *Pseudoplusia includens,* soybean looper; *Anticarsia gemmatalis,* velvetbean caterpillar; *Plathypena scabra,* green cloverworm; *Ostrinia nubilalis,* European corn borer; *Agrotis ipsilon,* black cutworm; *Spodoptera exigua,* beet armyworm; *Heliothis virescens,* cotton budworm; *Helicoverpa zea,* cotton bollworm; *Epilachna varivestis,* Mexican bean beetle; *Myzus persicae,* green peach aphid; *Empoasca fabae,* potato leafhopper; *Acrosternum hilare,* green stink bug; *Melanoplus femurrubrum,* redlegged grasshopper; *Melanoplus differentialis,* differential grasshopper; *Hylemya platura,* seedcorn maggot; *Sericothrips variabilis,* soybean thrips; *Thrips tabaci,* onion thrips; *Tetranychus turkestani,* strawberry spider mite; *Tetranychus urticae,* twospotted spider mite; Barley: *Ostrinia nubilalis,* European corn borer; *Agrotis ipsilon,* black cutworm; *Schizaphis graminum,* greenbug; *Blissus leucopterus leucopterus,* chinch bug; *Acrosternum hilare,* green stink bug; *Euschistus servus,* brown stink bug; *Delia platura,* seedcorn maggot; *Mayetiola destructor,* Hessian fly; *Petrobia latens,* brown wheat mite; Oil Seed Rape: *Brevicoryne brassicae,* cabbage aphid; *Phyllotreta cruciferae,* Flea beetle; *Mamestra configurata,* Bertha armyworm; *Plutella xylostella,* Diamond-back moth; *Delia* ssp., Root maggots.

The present invention also provides isolated nucleic acids comprising polynucleotides of sufficient length and complementarity to a gene of the invention to use as probes or amplification primers in the detection, quantification, or isolation of gene transcripts. For example, isolated nucleic acids of the present invention can be used as probes in detecting deficiencies in the level of mRNA in screenings for desired transgenic plants, for detecting mutations in the gene (e.g., substitutions, deletions, or additions), for monitoring up-regulation of expression or changes in enzyme activity in screening assays of compounds, for detection of any number of allelic variants (polymorphisms) of the gene, or for use as molecular markers in plant breeding programs. The isolated nucleic acids of the present invention can also be used for recombinant expression of polypeptides, or for use as immunogens in the preparation and/or screening of antibodies. The isolated nucleic acids of the present invention can also be employed for use in sense or antisense suppression of one or more genes of the invention in a host cell, tissue, or plant. Attachment of chemical agents, which bind, intercalate, cleave and/or crosslink to the isolated nucleic acids of the present invention can also be used to modulate transcription or translation. Further, using a primer specific to an insertion sequence (e.g., transposon) and a primer which specifically hybridizes to an isolated nucleic acid of the present invention, one can use nucleic acid amplification to identify insertion sequence inactivated genes of the invention from a cDNA library prepared from insertion sequence mutagenized plants. Progeny seed from the plants comprising the desired inactivated gene can be grown to a plant to study the phenotypic changes characteristic of that inactivation. See, *Tools to Determine the Function of Genes*, 1995 Proceedings of the Fiftieth Annual Corn and Sorghum Industry Research Conference, American Seed Trade Association, Washington, D.C., 1995. Additionally, non-translated 5' or 3' regions of the polynucleotides of the present invention can be used to modulate turnover of heterologous mRNAs and/or protein synthesis. Further, the codon preference characteristic of the polynucleotides of the present invention can be employed in heterologous sequences, or altered in homologous or heterologous sequences, to modulate translational level and/or rates.

The present invention provides a method of genotyping a plant comprising a polynucleotide of the present invention. The plant may be a monocot, such as maize or sorghum, or alternatively, a dicot, such as sunflower or soybean. Genotyping provides a means of distinguishing homologues of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. See, e.g., *Plant Molecular Biology: A Laboratory Manual*, Chapter 7, Clark, Ed., Springer-Verlag, Berlin (1997). For molecular marker methods, see generally, The DNA Revolution by Andrew H. Paterson 1996 (Chapter 2) in: Genome Mapping in Plants (ed. Andrew H. Paterson) by Academic Press/R. G. Landis Company, Austin, Tex., pp. 7–21.

The particular method of genotyping in the present invention may employ any number of molecular marker analytic techniques such as, but not limited to, restriction fragment length polymorphisms (*RFLPs*). Thus, the present invention further provides a means to follow segregation of a gene or nucleic acid of the present invention as well as chromosomal sequences genetically linked to these genes or nucleic acids using such techniques as RFLP analysis. Linked chromosomal sequences are within 50 centiMorgans (cM), often within 40 or 30 cM, preferably within 20 or 10 cM, more preferably within 5, 3, 2, or 1 cM of a gene of the invention.

In the present invention, the nucleic acid probes employed for molecular marker mapping of plant nuclear genomes selectively hybridize, under selective hybridization conditions, to a gene encoding a polynucleotide of the present invention. Preferably, the probes are selected from polynucleotides of the present invention. Typically, these probes are cDNA probes or Pst I genomic clones. The length of the probes is discussed in greater detail, supra, but are typically at least 15 bases in length, more preferably at least 20, 25, 30, 35, 40, or 50 bases in length. Generally, however, the probes are less than about 1 kilobase in length. Preferably, the probes are single copy probes that hybridize to a unique locus in a haploid chromosome complement.

The present invention further provides a method of genotyping comprising the steps of contacting, under stringent hybridization conditions, a sample suspected of comprising a polynucleotide of the present invention with a nucleic acid probe. Generally, the sample is a plant sample; preferably, a sample suspected of comprising a maize polynucleotide of the present invention (e.g., gene, mRNA). The nucleic acid probe selectively hybridizes, under stringent conditions, to a subsequence of a polynucleotide of the present invention comprising a polymorphic marker. Selective hybridization of the nucleic acid probe to the polymorphic marker nucleic acid sequence yields a hybridization complex. Detection of the hybridization complex indicates the presence of that polymorphic marker in the sample. Preferably, the nucleic acid probe comprises a polynucleotide of the present invention.

The following examples are presented by way of illustration, not by way of limitation.

EXPERIMENTAL

EXAMPLE 1

Isolation of Sunflower Defense Signaling Genes

Materials and Methods

Plant Materials

Sunflower plants were grown in the greenhouse and growth chamber. The sunflower line SMF3 and oxox-transgenic sunflower (line 193870) were used for mRNA profiling. Sunflower pathogen, *Sclerotinia sclerotiorum*, was maintained on PDA plates at 20° C. in the dark.

For fungal infection and chemical treatments, SMF3 sunflower plants were planted in four-inch pots and grown in greenhouse for the first four weeks. After transfer to the growth chamber, the plants were maintained under 12-hour photoperiod at 22° C. with an 80% relative humidity. Six-week old plants were inoculated with Sclerotinid-infected carrot plugs or sprayed with an aqueous solution of either 5 mM oxalic acid, 5 mM $H_2O_2$, 5 mM salicylic acid or 45 $\mu$M jasmonic acid (with 0.1% ethanol). For each plant, three petioles were inoculated and wrapped with a 1 inch×2 inch piece of parafilm. Plant tissue samples were harvested at different time points and immediately frozen in liquid nitrogen and then stored at −80° C.

Preparation of Total RNA for RNA Profiling and Northern Analysis

Plant materials were ground in liquid nitrogen, and total RNA was extracted by the Tri-Reagent method. RNA profiling was conducted using CuraGen Corporation's proprietary method sold under the trademark GENECALLING. See U.S. Pat. No. 5,871,697, herein incorporated by reference. Profiles of RNA samples prepared from combined leaf and stem tissues of six-week-old oxox sunflower plants were compared to profiles of similar RNA samples from of six-week-old SMF3 plants.

Total RNA (20 $\mu$g) was separated in a 1% agarose gel containing formaldehyde. Ethidium bromide was included to verify equal loading of RNA. After transfer onto Hybond N+membrane, the blots were hybridized with $^{32}$P-labeled NCE, AAP, or GRP cDNA probes. As a control, a duplicate blot was hybridized with a probe complementary to 18S rRNA. Hybridization and washing conditions were performed according to Church et al. ((1984) *Proc. Natl. Acad. Sci. USA* 81:1991–1995).

Isolation of Full-length or Flanking Sequences by PCR Amplification of cDNA Ends The three defense-related cDNAs were isolated by using RNA profiling and PCR-based technologies. The sequence information generated by RNA profiling was used for designing gene-specific primers for amplifying both 3'- and/or 5'-end regions of the target genes using the rapid amplification of cDNA ends (RACE) method. Sclerotinia-infected and oxox-induced sunflower cDNA libraries were directionally constructed into pBluescript phagemid using a ZAP-cDNA synthesis kit from Stratagene. The cDNA libraries were used as a source of templates for PCR amplification.

To facilitate cloning full-length cDNAs from the initially cloned regions, a pair of 26 bp vector primers P3 (SEQ ID NO: 9) and P4 (SEQ ID NO: 10) were designed to hybridize to pBluescript vector sequences flanking both the 3'- and 5'-end regions of the cloned cDNAs. Initially, the 5'-end vector primer was paired with a gene-specific primer (P1) to directionally amplify the 5' end of the cloned cDNA. Once the anticipated 5' end of a specific cDNA with an intact ATG start codon was cloned and sequenced, the full-length cDNA was amplified using a second gene-specific primer (P5) designed to hybridize to a sequence at or upstream of ATG region sequence and a 3'-end vector primer (P4). The 3' end of a target cDNA was amplified employing a gene-specific primer P2 and the 3' end vector primer, P4. PCR products were cloned and sequenced.

For the isolation of the NCE cDNA by PCR amplification, oligonucleotide primers P1, P2, and P5 (SEQ ID NOs: 11–13, respectively) were employed. For the isolation of the AAP cDNA, oligonucleotide primers P1 and P2 (SEQ ID NOs: 14–15 respectively) were utilized. Finally, oligonucleotide primers P1, P2, and P5 (SEQ ID NOs: 16–18, respectively) were utilized to isolate the GRP cDNA.

The PCR reactions were performed in a total volume of 25 µL in 10 mM Tris-HCl, pH 8.3; 1.5 mM $MgCl_2$; 50 mM KCl; 0.1 mM dNTPs; 0.25 µM of each primer; and 0.5 units of advantage cDNA polymerase mix (Clontech) or Pwo DNA polymerase (Boehringer). Genomic DNA and/or cDNA library mixtures were used as a source of templates for PCR amplification.

Isolation of Promoters

The promoter region of an NCE gene was isolated from sunflower genomic DNA using the Universal GenomeWalker Kit (Clontech) according to the manufacturer's instruction using an oligonucleotide primer designed from the NCE cDNA (SEQ ID NO: 19). Restriction digested genomic DNAs were ligated with an adapter to construct pools of genomic DNA fragments for walking by PCR (Siebert et al. (1995) Nuc. Acids Res. 23:1087–1088). The promoter region of a GRP gene was isolated using a similar approach.

Analysis of Amplified PCR Products

Amplified PCR fragments with the expected sizes were individually sliced out of a gel for use as template DNA for a second round of PCR amplification with the same conditions as the initial PCR reaction. Each second-round PCR product showing a single band with the expected size was cloned into TA vector (Clontech) according to the supplier's instructions. Identified positive clones were selected for DNA sequencing using an Applied Biosystems 373A (ABI) automated sequencer at the Nucleic Acid Analysis Facility of Pioneer Hi-Bred International, Incorporated. DNA sequence analysis was carried out with the Sequencer (3.0). Multiple-sequence alignments of the DNA sequence were carried out using Clustal W (Version 1.7, default parameters) within the bioinformatics software package from CuraGen Corporation sold under the trademark CURATOOLS.

Construction of Sclerotinia-infected and Resistance-enhanced (Oxox-induced) Sunflower cDNA Libraries Six-week old SMF3 sunflower plants were infected with Sclerotinia sclerotiorum by petiole inoculation with Sclerotinia-infested carrot plugs. Six days after infection, leaf and stem tissues were collected from infected plants for total RNA isolation. Total RNA was also isolated from six-week-old sunflower oxox-transgenic plants (line 610255), which are known to express a wheat oxalate oxidase gene. Our previous studies indicated that elevated levels of $H_2O_2$, SA, and PR1 protein were detected in such oxox-transgenic plants at the six-week-old stage and these plants had a greater level of resistance to infection with Scierotinia (see copending U.S. Application Serial No. 60/053,123 filed Jul. 18, 1997). Messenger RNA was isolated using an mRNA purification kit (BRL) according to the manufacturer's instruction. The cDNA libraries were constructed with the ZAP-cDNA synthesis kit into pBluescript phagemid (Stratagene). A cDNA library mixture for PCR cloning was made from oxox transgenic stem and Sclerotinia-infected leaf libraries (1:2 mix).

Results

RNA Profiling Study of Oxox-transgenic Sunflower Plants

Resistance to the fungal pathogen Sclerotinia is a trait of major importance for crops such as sunflower, canola (Brassica sp.), and soybean. Expression of oxox by constitutive promoters significantly enhances resistance to Sclerotinia in sunflower. In a growth chamber experiment, the oxox-transgenic sunflower plants, upon infection with Sclerotinia mycelia, were observed to have lesions that were one-sixth the size of lesions found on similarly treated, non-transformed plants. At the six-week-old stage, the oxox-transgenic sunflower plants displayed a lesion-mimic phenotype in mature leaves, indicating that oxox expression in sunflower induces a hypersensitive response. To identify the oxidase-induced genes and elucidate their roles in the enhanced resistance, an RNA profiling study was carried out. Using this approach, at least 30 bands were found to be induced, and at least 30 bands were found to be repressed in the oxox-transgenic stem and leaf tissues as compared to non-transformed SMF3 plants. The DNA fragments corresponding to three of the bands were isolated and sequenced, and the sequence information was used to clone the full-length clones.

Isolation of Full-length, Defense-related cDNAs from Sunflower

A PCR-based clonin method was developed to efficiently isolate, from sunflower cDNA libraries, full-length cDNAs corresponding to plant defense genes. A cDNA library mixture containing both DNA from oxox-transgenic cDNA library and DNA from a Sclerotinia-infected cDNA library (1:2 mix) was used as template for PCR amplification. Using cDNA libraries as a source of template DNA in the PCR amplifications had two-fold benefits. First, the number of unexpected PCR products was reduced as compared with the use of genomic DNA as a source of templates. Second, the use of DNA templates from disease-induced cDNA libraries increased the chance of isolating defense-related genes.

NCE cDNA and Its Promoter

The NCE cDNA is 1950 bp in length (SEQ ID NO: 1) with an open reading frame of 592 amino acids (SEQ ID NO: 2). The calculated molecular mass is 59.3 kDa with pI at 5.57. The sunflower NCE shared 69% amino acid identity with an NCE-like protein from Arabidopsis thaliana (SEQ ID NO: 20) as determined by BLASTX (Version 2.0) using the default parameters (FIG. 1). NCE is a key enzyme of ABA biosynthesis, which catalyzes-the oxidative cleavage of 9-cis-epoxy carotenoids to xanthoxin. Results from Northern blotting experiments indicated that the transcription of this gene was repressed in both oxox-transgenic and Sclerotinia-infected, sunflower leaf tissues (FIG. 3). In addition, sunflower NCE gene expression was negatively regulated when sunflower plants were treated with chemicals involving disease signal transduction, such as $H_2O_2$ (5 mM), salicylic acid (SA) (5 mM), and jasmonic acid (JA) (45 μM in 0.1% ethanol), and with a pathogenic factor, oxalic acid (OA) (5 mM) (FIG. 4).

Between the four-week-old and six-week-old stages, PR5 gene expression was significantly induced whereas NCE gene expression was dramatically repressed (FIG. 6). These results indicate that there is a potential alteration in one or more pathways in the oxox-transgenic leaves between the four-week-old and six-week-old stages. While the exact role of the ABA pathway in pathogen defense responses has not yet been defined, the results with oxox sunflower reveal that down regulation of ABA biosynthesis pathway may promote the activation of the pathogen defense pathways in sunflower.

The promoter of the NCE gene was also isolated. Sequence analysis indicated that NCE promoter contains the pathogen-responsive elements, MRE and W-box (SEQ ID NO: 3). However, the W-box sequence (GGTCAA) in the sunflower NCE promoter was in a reverse orientation when compared to the orientation of W-boxes in other disease resistance genes. This reverse orientation may cause down-regulation effects.

AAP cDNA

The AAP cDNA is 1656 bp in length (*SEQ ID NO:* 4) with an open reading frame that encodes a protein of 452 amino acids (SEQ ID NO: 5). A calculated molecular mass of the deduced protein is 50.6 kDa with a pI at 8.5. The sunflower AAP shared 75% amino acid identity with an Arabidopsis AAP (SEQ ID NO: 24) as determined by BLASTX (Version 2.0) using the default parameters (FIG. 2). Hydropathy analysis indicated that AAP is an integral membrane protein having eight, or possibly nine, putative, membrane-spanning domains. Northern blot analysis demonstrated that AAP was induced in oxox-transgenic sunflower plants. Two different sizes of AAP mRNA were detected in the control and Sclerotinia infected leaf tissues, indicating that there may be more than one AAP gene expressed in leaf tissues (FIG. 3).

A cDNA Encoding Novel Protein Designated GRP

Figure 5:
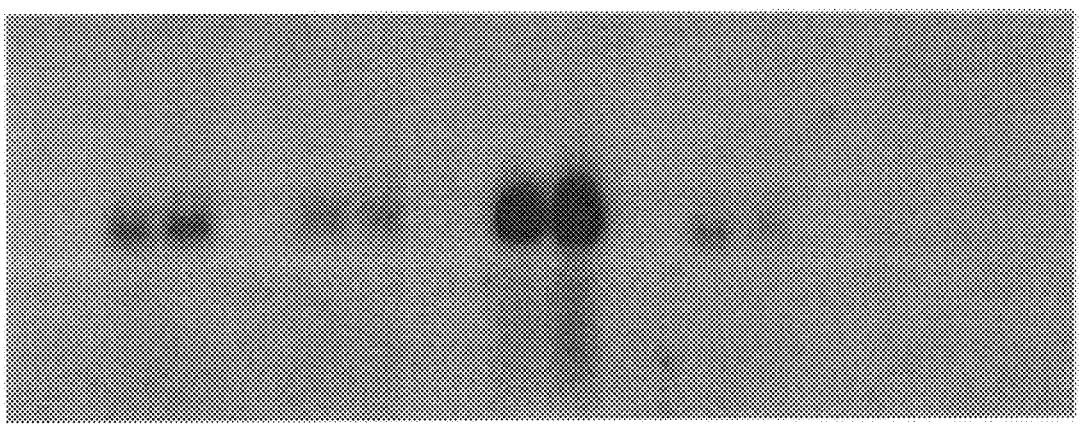
FIG. 5 depicts the results of a Northern blot analysis of GRP gene transcript levels in different tissues: Total RNA was isolated from five different plant tissues: young seed (Se), corolla tubes (C), stem (S), leaf (L), and root (R) tissues. RNA samples (20 $\mu$g) from control SMF3 plants (right) and oxox transgenic plants (left) were loaded in adjacent lanes for comparison.

The GRP cDNA is 865 nucleotides in length (SEQ ID NO: 6) with an open reading frame that encodes a polypeptide of 173 amino acids (SEQ ID NO: 7). The polypeptide has a calculated molecular mass of 18.8 kDa and is very acidic with pI of 3.92. The polypeptide encoded by the GRP cDNA has high percentage of both glutamic acid (46/173, 26.59%) and proline (22/173, 12.72%). Nucleotide sequence and amino acid sequence database searches did not reveal significant homology with any reported sequences. The GRP polypeptide shared 37% amino acid identity with a 144 amino acid region of a hypothetical 185.1 kDa protein from a Synechocystis sp. (SP-TrEMBL Accession No. P73032, SEQ ID NO: 28) as determined by BLASTX (Version 2.0) using the default parameters. Northern blot experiments (FIGS. 3 and 5) indicated that the gene corresponding to the GRP cDNA was highly expressed in stem tissue.

The promoter of the GRP gene was also isolated. Sequence analysis indicated that GRP promoter contains the pathogen-responsive element, W-box, and a bZIP protein-binding motif (SEQ ID NO: 8). Given the strong expression of GRP in stems relative to other tissues (FIG. 5), the GRP promoter can be used to drive the expression of an operably linked nucleotide sequence in plant stems. Additionally, RNA profiling indicated that the GRP expression was increased 23-fold in oxox sunflower leaf tissues when compared to similar SMF3 plants. Thus, the GRP promoter can be used to drive the expression of an operably linked nucleotide sequence in plant tissues having increased oxalate oxidase expression.

EXAMPLE 2

Transformation and Regeneration of Sunflower Plants

Sunflower meristem tissues are transformed with an expression cassette containing the NCE, AAP, or GRP nucleotide sequence of the invention (see also European Patent Number EP 0 486233, herein incorporated by reference, and Malone-Schoneberg et al.(1994) *Plant Science* 103:199–207). Mature sunflower seed (*Helianthus annuus L.*) are dehulled using a single wheat-head thresher. Seeds are surface sterilized for 30 minutes in a 20% Clorox bleach solution with the addition of two drops of Tween 20 per 50 mL of solution. The seeds are rinsed twice with sterile distilled water.

Split embryonic axis explants are prepared by a modification of procedures described by Schrammeijer et al. (*Schrammeijer et al.* (1990) *Plant Cell Rep.* 9: 55–60). Seeds are imbibed in distilled water for 60 minutes following the surface sterilization procedure. The cotyledons of each seed are then broken off, producing a clean fracture at the plane of the embryonic axis. Following excision of the root tip, the explants are bisected longitudinally between the primordial leaves. The two halves are placed, cut surface up, on GBA medium consisting of Murashige and Skoog mineral elements (Murashige et al. (1962) *Physiol. Plant.,* 15: 473–497), Shepard's vitamin additions (Shepard (1980) in *Emergent Techniques for the Genetic Improvement of Crops* (University of Minnesota Press, St. Paul, Minn.), 40 mg/L adenine sulfate, 30 g/L sucrose, 0.5 mg/L 6-benzyl-aminopurine (BAP), 0.25 mg/L indole-3-acetic acid (IAA), 0.1 mg/L gibberellic acid ($GA_3$), pH 5.6, and 8 g/L Phytagar.

The explants are subjected to microprojectile bombardment prior to Agrobacterium treatment (Bidney et al. (1992) *Plant Mol. Biol.* 18: 301–313). Thirty to forty explants are placed in a circle at the center of a 60×20 mm plate for this treatment. Approximately 4.7 mg of 1.8 mm tungsten microprojectiles are resuspended in 25 mL of sterile TE buffer (10 mM Tris HCl, 1 mM EDTA, pH 8.0) and 1.5 mL aliquots are used per bombardment. Each plate is bombarded twice through a 150 mm nytex screen placed 2 cm above the samples in a PDS 1000® particle acceleration device.

Disarmed *Agrobacterium tumefaciens* strain EHA105 is used in all transformation experiments. A binary plasmid vector comprising the expression cassette that contains the NCE, AAP, or GRP nucleotide sequence is introduced into Agrobacterium strain EHA105 via freeze-thawing as described by Holsters et al. (1978) *Mol. Gen. Genet.* 163:181–187. This plasmid further comprises a kanamycin selectable marker gene (i.e, nptII). Bacteria for plant transformation experiments are grown overnight (28° C. and 100 RPM continuous agitation) in liquid YEP medium (10 g/L yeast extract, 10 g/L Bactopeptone, and 5 g/L NaCl, pH 7.0) with the appropriate antibiotics required for bacterial strain and binary plasmid maintenance. The suspension is used when it reaches an $OD_{600}$ of about 0.4 to 0.8. The Agrobacterium cells are pelleted and resuspended at a final $OD_{600}$ of 0.5 in an inoculation medium comprised of 12.5 mM MES pH 5.7, 1 g/L $NH_4Cl$, and 0.3 g/L $MgSO_4$.

Freshly bombarded explants are placed in an Agrobacterium suspension, mixed, and left undisturbed for 30 minutes. The explants are then transferred to GBA medium and co-cultivated, cut surface down, at 26° C. and 18-hour days. After three days of co-cultivation, the explants are transferred to 374B (*GBA medium lacking growth regulators and a reduced sucrose level of 1%*) supplemented with 250 mg/L cefotaxime and 50 mg/L kanamycin sulfate. The explants are cultured for two to five weeks on selection and then transferred to fresh 374B medium lacking kanamycin for one to two weeks of continued development. Explants with differentiating, antibiotic-resistant areas of growth that have not produced shoots suitable for excision are transferred to GBA medium containing 250 mg/L cefotaxime for a second 3-day phytohormone treatment. Leaf samples from green, kanamycin-resistant shoots are assayed for the presence of NPTII by ELISA. If, for example, the sunflower plants are transformed with an NCE, AAP, or GRP coding sequence, the presence of transgene expression may be determined by assaying for the level of the protein or a biological activity thereof.

NPTII-positive shoots are grafted to Pioneer® hybrid 6440 in vitro-grown sunflower seedling rootstock. Surface sterilized seeds are germinated in 48-0 medium (half-strength Murashige and Skoog salts, 0.5% sucrose, 0.3% gelrite, pH 5.6) and grown under conditions described for explant culture. The upper portion of the seedling is removed, a 1 cm vertical slice is made in the hypocotyl, and the transformed shoot inserted into the cut. The entire area is wrapped with parafilm to secure the shoot. Grafted plants can be transferred to soil following one week of in vitro culture. Grafts in soil are maintained under high humidity conditions followed by a slow acclimatization to the greenhouse environment. Transformed sectors of $T_0$ plants (parental generation) maturing in the greenhouse are identified by NPTII ELISA and/or by analysis of NCE, AAP, or GRP protein levels or biological activities in leaf extracts while transgenic seeds harvested from NPTII-positive $T_0$ plants are identified by analysis of NCE, AAP, or GRP protein levels or biological activities of small portions of dry seed cotyledon.

An alternative sunflower transformation protocol allows the recovery of transgenic progeny without the use of chemical selection pressure. Seeds are dehulled and surface-sterilized for 20 minutes in a 20% Clorox bleach solution with the addition of two to three drops of Tween 20 per 100 mL of solution, then rinsed three times with distilled water. Sterilized seeds are imbibed in the dark at 26° C. for 20 hours on filter paper moistened with water. The cotyledons and root radical are removed, and the meristem explants are cultured on 374E (GBA medium consisting of MS salts, Shepard vitamins, 40 mg/L adenine sulfate, 3% sucrose, 0.5 mg/L 6-BAP, 0.25 mg/L IAA, 0.1 mg/L GA, and 0.8% Phytagar at pH 5.6) for 24 hours under the dark. The primary leaves are removed to expose the apical meristem, around 40 explants are placed with the apical dome facing upward in a 2 cm circle in the center of 374M (GBA medium with 1.2% Phytagar), and then cultured on the medium for 24 hours in the dark.

Approximately 18.8 mg of 1.8 μm tungsten particles are resuspended in 150 μL absolute ethanol. After sonication, 8 μL of it is dropped on the center of the surface of macrocarrier. Each plate is bombarded twice with 650 psi rupture discs in the first shelf at 26 mm of Hg helium gun vacuum.

The plasmid of interest is introduced into *Agrobacterium tumefaciens* strain EHA105 via freeze thawing as described previously. The pellet of overnight-grown bacteria at 28° C. in a liquid YEP medium (10 g/L yeast extract, 10 g/L Bactopeptone, and 5 g/L NaCl, pH 7.0) in the presence of 50 μg/L kanamycin is resuspended in an inoculation medium (12.5 mM 2-mM 2-(N-morpholino) ethanesulfonic acid, MES, 1 g/L $NH_4Cl$, and 0.3 g/L $MgSO_4$ at pH 5.7) to reach a final concentration of 4.0 at OD 600. Particle-bombarded explants are transferred to GBA medium (374E), and a droplet of bacteria suspension is placed directly onto the top of the meristem. The explants are co-cultivated on the medium for 4 days, after which the explants are transferred to 374C medium (*GBA with 1% sucrose and no BAP, IAA, GA3 and supplemented with 250 μg/mL cefotaxime*). The plantlets are cultured on the medium for about two weeks under 16-hour day and 26° C. incubation conditions.

Explants (around 2 cm long) from two weeks of culture in 374C medium are screened for NCE, AAP, or GRP protein levels or biological activities using assays known in the art. After positive (i.e., for expression of the desired transgene) explants are identified, those shoots that fail to exhibit the desired protein level or activity are discarded, and every positive explant is subdivided into nodal explants. One nodal explant contains at least one potential node. The nodal segments are cultured on GBA medium for three to four days to promote the formation of auxiliary buds from each node. Then they are transferred to 374C medium and allowed to develop for an additional four weeks. Developing buds are separated and cultured for an additional four weeks on 374C medium. Pooled leaf samples from each newly recovered shoot are screened again by the appropriate protein activity assay. At this time, the positive shoots recovered from a single node will generally have been enriched in the transgenic sector detected in the initial assay prior to nodal culture.

Recovered shoots positive for expression of the transgene of interest are grafted to Pioneer hybrid 6440 in vitro-grown sunflower seedling rootstock. The rootstocks are prepared in the following manner. Seeds are dehulled and surface-sterilized for 20 minutes in a 20% Clorox bleach solution with the addition of two to three drops of Tween 20 per 100 mL of solution, and are rinsed three times with distilled water. The sterilized seeds are germinated on the filter moistened with water for three days, then they are transferred into 48 medium (half-strength MS salt, 0.5% sucrose, 0.3% gelrite pH 5.0) and grown at 26° C. under the dark for three days, then incubated at 16-hour-day culture conditions. The upper portion of selected seedling is removed, a vertical slice is made in each hypocotyl, and a transformed shoot is inserted into a V-cut. The cut area is wrapped with parafilm. After one week of culture on the medium, grafted plants are transferred to soil. In the first two weeks, they are maintained under high humidity conditions to acclimatize to a greenhouse environment.

EXAMPLE 3

Soybean Embryo Transformation

Soybean embryos are bombarded with a plasmid containing the NCE, AAP, or GRP nucleotide sequence of the invention as follows. To induce somatic embryos, cotyledons, 3–5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70–73, U.S. Pat. No. 4,945,050). A Du Pont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell et al. (1985) *Nature* 313:810–812), the hygromycin phosphotransferase gene from plasmid pJR225 (from *E. coli*; Gritz et al. (1983) *Gene* 25:179–188), and the 3' region of the nopaline synthase gene from the T-DNA of the Ti plasmid of *Agrobacterium tumefaciens*. The expression cassette comprising the NCE, AAP, or GRP nucleotide sequence of the invention can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µl), 20 µL spermidine (0.1 M), and 50 µL CaCl$_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five microliters of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/mL hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

EXAMPLE 4

Transformation and Regeneration of Maize Plants

Immature maize embryos from greenhouse donor plants are bombarded with a plasmid containing the NCE, AAP, or GRP nucleotide sequence of the invention and the selectable marker gene PAT (Wohlleben et al. (1988) *Gene* 70:25–37), which confers resistance to the herbicide Bialaphos. Alternatively, the selectable marker gene is provided on a separate plasmid. Transformation is performed as follows. Media recipes follow below.

Preparation of Target Tissue

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising NCE, AAP, or GRP nucleotide sequence of the invention is constructed. This plasmid DNA plus plasmid DNA containing a PAT selectable marker is precipitated onto 1.1 µm (average diameter) tungsten pellets using a CaCl$_2$ precipitation procedure as follows:

100 µL prepared tungsten particles in water
10 µL (1 µg) DNA in Tris EDTA buffer (1 µg total DNA)
100 µL 2.5 M CaCl$_2$
10 µL 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 mL 100% ethanol, and centrifuged for 30 seconds. Again the liquid is removed, and 105 µL 100% ethanol is added to the.final tungsten particle pellet. For particle gun bombardment, the tungsten/DNA particles are briefly sonicated and 10 µL spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2–4 weeks), well-developed somatic embryos are transferred to medium for germination and transferred to the lighted culture room. Approximately 7–10 days later, developing plantlets are transferred to 272V hormone-free medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity. Plants are monitored and scored for the desired phenotypic trait associated with the NCE, AAP, or GRP nucleotide sequence of the invention.

Bombardment and Culture Media

Bombardment medium (560Y) comprises 4.0 g/L N6 basal salts (SIGMA C-1416), 1.0 mL/L Eriksson's Vitamin Mix (1000X SIGMA-1511), 0.5 mg/L thiamine HCl, 120.0 g/L sucrose, 1.0 mg/L 2,4-D, and 2.88 g/L L-proline (brought to volume with D-I H$_2$0 following adjustment to pH 5.8 with KOH); 2.0 g/L Gelrite (added after bringing to volume with D-I H$_2$0); and 8.5 mg/L silver nitrate (added after sterilizing the medium and cooling to room temperature). Selection medium (560R) comprises 4.0 g/L N6 basal salts (SIGMA C-1416), 1.0 mL/L Eriksson's Vitamin Mix (1000X SIGMA-1511), 0.5 mg/L thiamine HCl, 30.0 g/L sucrose, and 2.0 mg/L 2,4-D (brought to volume with D-I H$_2$0 following adjustment to pH 5.8 with KOH); 3.0 g/L Gelrite (added after bringing to volume with D-I H$_2$0); and 0.85 mg/L silver nitrate and 3.0 mg/L bialaphos(both added after sterilizing the medium and cooling to room temperature).

Plant regeneration medium (288J) comprises 4.3 g/L MS salts (GIBCO 11117-074), 5.0 mL/L MS vitamins stock solution (0.100 g nicotinic acid, 0.02 g/L thiamine HCL, 0.10 g/L pyridoxine HCL, and 0.40 g/L glycine brought to volume with polished D-I H$_2$0) (Murashige and Skoog (1962) *Physiol. Plant.* 15:473), 100 mg/L myo-inositol, 0.5 mg/L zeatin, 60 g/L sucrose, and 1.0 mL/L of 0.1 mM abscisic acid (brought to volume with polished D-I H$_2$0 after adjusting to pH 5.6); 3.0 g/L Gelrite (added after bringing to volume with D-I H$_2$0); and 1.0 mg/L indoleacetic acid and 3.0 mg/L bialaphos (added after sterilizing the medium and cooling to 60° C.). Hormone-free medium (272V) comprises 4.3 g/L MS salts (GIBCO 11117-074), 5.0 mL/L MS vitamins stock solution (0.100 g/L nicotinic acid, 0.02 g/L thiamine HCL, 0.10 g/L pyridoxine HCL, and 0.40 g/L glycine brought to volume with polished D-I H$_2$0), 0.1 g/L myo-inositol, and 40.0 g/L sucrose (brought to volume with polished D-I H$_2$0 after adjusting pH to 5.6); and 6 g/L bacto-agar (added after bringing to volume with polished D-I H$_2$0), sterilized and cooled to 60° C.

EXAMPLE 5

Agrobacterium-mediated Transformation of Maize

For Agrobacterium-mediated transformation of maize with an NCE, AAP, or GRP nucleotide sequence of the invention preferably the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of Agrobacterium, where the bacteria are capable of transferring the NCE, AAP, or GRP nucleotide sequence of the invention to at least one cell of at least one of the immature embryos (step 1: the infection step). In this step the immature embryos are preferably immersed in an Agrobacterium suspension for the initiation of inoculation. The embryos are co-cultured for a time with the Agrobacterium (step 2: the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of Agrobacterium without the addition of a selective agent for plant transformants (step 3: resting step). Preferably the immature embryos are cultured on solid medium with antibiotic, but without a selecting agent, for elimination of Agrobacterium and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step), and preferably calli grown on selective medium are cultured on solid medium to regenerate the plants.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated nucleotide sequence selected from the group consisting of:
   (a) a nucleotide sequence comprising at least 95% sequence identity to the sequence of SEQ ID NO: 1, wherein said nucleotide sequence encodes a polypeptide having neoxanthin cleavage enzyme activity; and
   (b) a nucleotide sequence that is the full complement of the nucleotide sequence.

2. An expression cassette comprising the nucleotide sequence of claim 1, said nucleotide sequence operably linked to a promoter that drives expression in a plant cell.

3. A transformed plant comprising in its genome at least one stably incorporated DNA construct comprising a nucleotide sequence operably linked to a promoter that drives expression in a plant, wherein said nucleotide sequence is selected from the group consisting of:
   (a) a nucleotide sequence comprising the sequence set forth in SEQ ID NO: 1;
   (b) a nucleotide sequence encoding a polypeptide comprising the amino acid sequence set forth in SEQ ID NO: 2; and
   (c) a nucleotide sequence that is the full complement of the nucleotide sequence of any one of (a)–(b).

4. The plant of claim 3, wherein said promoter is selected from the group consisting of pathogen-inducible, wound-inducible, constitutive, tissue-preferred, and chemically regulatable promoters.

5. The plant of claim 3, wherein said nucleotide sequence is operably linked to said promoter for the production of antisense transcripts.

6. The plant of claim 3, wherein said plant is a monocot.

7. The plant of claim 6, wherein said monocot is selected from the group consisting of maize, wheat, rice, barley, sorghum, millet, and rye.

8. The plant of claim 3, wherein said plant is a dicot.

9. The plant of claim 8, wherein said dicot is selected from the group consisting of soybean, Brassica sp., sunflower, safflower, alfalfa, and cotton.

10. Transformed seed of the plant of claim 3.

11. A transformed plant cell comprising in its genome at least one stably incorporated DNA construct comprising a nucleotide sequence operably linked to a promoter that drives expression in a plant cell, wherein said nucleotide sequence is selected from the group consisting of:
   (a) a nucleotide sequence comprising the sequence set forth in SEQ ID NO: 1;

(b) a nucleotide sequence encoding a polypeptide comprising the amino acid sequence set forth in SEQ ID NO: 2; and (c) a nucleotide sequence that is the full complement of the nucleotide sequence of any one of (a)–(b).

12. A method for increasing the resistance of a plant to a pathogen comprising stably incorporating in the genome of said plant a DNA construct comprising a nucleotide sequence operably linked to a promoter that drives expression in a plant, wherein said nucleotide sequence is selected from the group consisting of:

(a) a nucleotide sequence comprising the sequence set forth in SEQ ID NO: 1;

(b) a nucleotide sequence encoding a polypeptide comprising the amino acid sequence set forth in SEQ ID NO: 2; and (c) a nucleotide sequence that is the full complement of the nucleotide sequence of any one of (a)–(b);

wherein the resistance of said plant to said pathogen is increased.

13. The method of claim 12, wherein said promoter is selected from the group consisting of pathogen-inducible, wound-inducible, constitutive, tissue-preferred, and chemically regulatable promoters.

14. The method of claim 12, wherein said nucleotide sequence is operably linked to said promoter for the production of antisense transcripts.

15. The method of claim 12, wherein said pathogen is selected from the group consisting of a fungus, a virus, and a bacterium.

16. An isolated nucleotide sequence selected from the group consisting of:

(a) the nucleotide sequence comprising the sequence set forth in SEQ ID NO: 1; and (b) a nucleotide sequence encoding a polypeptide comprising the amino acid sequence set forth in SEQ ID NO: 2.

17. An isolated nucleotide sequence comprising the full complement of the nucleotide sequence of claim 16.

18. An expression cassette comprising the nucleotide sequence of claim 16, said nucleotide sequence operably linked to a promoter that drives expression in a plant cell.

19. An expression cassette comprising the nucleotide sequence of claim 17, said nucleotide sequence operably linked to a promoter that drives expression in a plant cell.

20. A transformed plant comprising in its genome at least one stably incorporated DNA construct comprising a nucleotide sequence operably linked to a promoter that drives expression in a plant, wherein said nucleotide sequence is selected from the group consisting of:

(a) a nucleotide sequence comprising at least 95% sequence identity to the sequence of SEQ ID NO: 1, wherein said nucleotide sequence encodes a polypeptide having neoxanthin cleavage enzyme activity; and (b) a nucleotide sequence that is the full complement of the nucleotide sequence.

21. A transformed plant cell comprising in its genome at least one stably incorporated DNA construct comprising a nucleotide sequence operably linked to a promoter that drives expression in a plant cell, wherein said nucleotide sequence is selected from the group consisting of:

(a) a nucleotide sequence comprising at least 95% sequence identity to the sequence of SEQ ID NO: 1, wherein said nucleotide sequence encodes a polypeptide having neoxanthin cleavage enzyme activity; and (b) a nucleotide sequence that is the full complement of the nucleotide sequence.

22. A method for increasing the resistance of a plant to a pathogen comprising stably incorporating in the genome of said plant a DNA construct comprising a nucleotide sequence operably linked to a promoter that drives expression in a plant, wherein said nucleotide sequence is selected from the group consisting of:

(a) a nucleotide sequence comprising at least 95% sequence identity to the sequence of SEQ ID NO: 1, wherein said nucleotide sequence encodes a polypeptide having neoxanthin cleavage enzyme activity; and (b) a nucleotide sequence that is the full complement of the nucleotide sequence;

wherein the resistance of said plant to said pathogen is increased.

* * * * *

SEQUENCE LISTING

```
<160> NUMBER OF SEQ ID NOS: 28

<210> SEQ ID NO 1
<211> LENGTH: 1950
<212> TYPE: DNA
<213> ORGANISM: Helianthus annuus
<220> FEATURE:
<221> NAME/KEY: CDS
<222> LOCATION: (1)..(1776)

<400> SEQUENCE: 1 atg gac tct ctc tcc tca tct ttc att tcc att ttt tcc caa tca aac        48
Met Asp Ser Leu Ser Ser Ser Phe Ile Ser Ile Phe Ser Gln Ser Asn
 1               5                   10                  15 tca act gtt tcc cac cca cca cca tca tcg tct tca ccg cca tct gcg        96
Ser Thr Val Ser His Pro Pro Pro Ser Ser Ser Ser Pro Pro Ser Ala
             20                  25                  30 cta aga gtc ttt tca gtc agg act gaa gaa aaa cca gaa acc gtc acc       144
Leu Arg Val Phe Ser Val Arg Thr Glu Glu Lys Pro Glu Thr Val Thr
         35                  40                  45 agt acc gcc acc acc aaa aga cct agt gga ccg aaa aag caa cca acc       192
Ser Thr Ala Thr Thr Lys Arg Pro Ser Gly Pro Lys Lys Gln Pro Thr
```

| | | |
|---|---|---|
| ctg aat att aga aaa cgt gaa agt tca gtg gtg gtg gat cag tct tta<br>Leu Asn Ile Arg Lys Arg Glu Ser Ser Val Val Val Asp Gln Ser Leu<br>65                        70                           75                       80 | | 240 |
| ccc gcc acc atc ttt aat gct ttt gat agc atc att aat aac ttt att<br>Pro Ala Thr Ile Phe Asn Ala Phe Asp Ser Ile Ile Asn Asn Phe Ile<br>                         85                         90                       95 | | 288 |
| gat cca ccg gcg agg gtc tca gtt gat cca aaa cac gtt ttg tct gat<br>Asp Pro Pro Ala Arg Val Ser Val Asp Pro Lys His Val Leu Ser Asp<br>                100                      105                    110 | | 336 |
| aac ttt tca ccg gtg gac gaa ctc cct ccg act gac tgt gaa gtc atc<br>Asn Phe Ser Pro Val Asp Glu Leu Pro Pro Thr Asp Cys Glu Val Ile<br>            115                      120                    125 | | 384 |
| gag ggc aca ctg cca agt tgc ctt gac ggt gct tac ttc cgt aat ggt<br>Glu Gly Thr Leu Pro Ser Cys Leu Asp Gly Ala Tyr Phe Arg Asn Gly<br>130                       135                    140 | | 432 |
| ccg aac ccg caa ttc ctt ccg cga gga ccc tac cac ctc ttc gat ggc<br>Pro Asn Pro Gln Phe Leu Pro Arg Gly Pro Tyr His Leu Phe Asp Gly<br>145                       150                    155                    160 | | 480 |
| gat ggc atg ctc cat gct att cgt atc tcc aat gga aaa gct tcg tta<br>Asp Gly Met Leu His Ala Ile Arg Ile Ser Asn Gly Lys Ala Ser Leu<br>                165                      170                    175 | | 528 |
| tgt agc cga tac atc aaa aca tac aaa tat tca ata gag aaa gaa gcg<br>Cys Ser Arg Tyr Ile Lys Thr Tyr Lys Tyr Ser Ile Glu Lys Glu Ala<br>                  180                      185                    190 | | 576 |
| gga ttc ccc att att cca aac gtg ttt tca ggg ttt aat ggt gtg act<br>Gly Phe Pro Ile Ile Pro Asn Val Phe Ser Gly Phe Asn Gly Val Thr<br>            195                      200                    205 | | 624 |
| gcc tct gca gct cgc atg gca gtc act gcc ggc cga ttt ttg gct gga<br>Ala Ser Ala Ala Arg Met Ala Val Thr Ala Gly Arg Phe Leu Ala Gly<br>210                       215                    220 | | 672 |
| caa ttt gac ccc aca aaa ggt att ggt cta gcc aat acc agt ctg gcc<br>Gln Phe Asp Pro Thr Lys Gly Ile Gly Leu Ala Asn Thr Ser Leu Ala<br>225                       230                    235                    240 | | 720 |
| ttt ttt ggc aac aga ctt ttt gct ctg gga gag tcg gat ctc cca tat<br>Phe Phe Gly Asn Arg Leu Phe Ala Leu Gly Glu Ser Asp Leu Pro Tyr<br>                245                      250                    255 | | 768 |
| gcc gtc aaa cta gcg ccc gac ggt gac ata gtc acc gtc gga cgt gag<br>Ala Val Lys Leu Ala Pro Asp Gly Asp Ile Val Thr Val Gly Arg Glu<br>            260                      265                    270 | | 816 |
| gac ttc gac ggc aaa cta ttc atg agc atg acc gct cac cca aaa atc<br>Asp Phe Asp Gly Lys Leu Phe Met Ser Met Thr Ala His Pro Lys Ile<br>            275                      280                    285 | | 864 |
| gat cca gta acg aaa gaa gct ttt gcc ttt cgt tac ggt cca gtc ccc<br>Asp Pro Val Thr Lys Glu Ala Phe Ala Phe Arg Tyr Gly Pro Val Pro<br>290                       295                    300 | | 912 |
| cct ttc cta acc ttt ttc cgt ttc aac gaa aac gga gaa aaa caa gcc<br>Pro Phe Leu Thr Phe Phe Arg Phe Asn Glu Asn Gly Glu Lys Gln Ala<br>305                       310                    315                    320 | | 960 |
| gat gtc ccg atc ttc tca atg aca agc ccg tcg ttt ctc cac gac ttc<br>Asp Val Pro Ile Phe Ser Met Thr Ser Pro Ser Phe Leu His Asp Phe<br>                325                      330                    335 | | 1008 |
| gcc atc acc aaa aac tac gcg att ttt ccc gag atc caa atc ggg atg<br>Ala Ile Thr Lys Asn Tyr Ala Ile Phe Pro Glu Ile Gln Ile Gly Met<br>            340                      345                    350 | | 1056 |
| agc cca atg gag atg ctg ggt ggg gga tcc ccg gtt agc gcg gac gct<br>Ser Pro Met Glu Met Leu Gly Gly Gly Ser Pro Val Ser Ala Asp Ala<br>            355                      360                    365 | | 1104 |
| gga aag gtg cct cgg ctc ggg ttg atc cct cgg tac gcg aaa gac gag | | 1152 |

```
Gly Lys Val Pro Arg Leu Gly Leu Ile Pro Arg Tyr Ala Lys Asp Glu
        370                 375                 380 tcc gag atg aag tgg ttt gag gtt ccg ggt ttt aat gtg ata cat tgc      1200
Ser Glu Met Lys Trp Phe Glu Val Pro Gly Phe Asn Val Ile His Cys
385                 390                 395                 400 atc aat gca tgg gag gag gat ggc gga gat acg gtg gtg atg gtg gct      1248
Ile Asn Ala Trp Glu Glu Asp Gly Gly Asp Thr Val Val Met Val Ala
                405                 410                 415 ccg aac ata tta tcg gtt gaa cat acg ttg gaa aga atg gat ttg att      1296
Pro Asn Ile Leu Ser Val Glu His Thr Leu Glu Arg Met Asp Leu Ile
            420                 425                 430 cat gca tcg gtt gag aaa gtg aag att aat ctg aaa aca gga atg gta      1344
His Ala Ser Val Glu Lys Val Lys Ile Asn Leu Lys Thr Gly Met Val
        435                 440                 445 tcc cgg cac ccg ctt tca acc cgg aat ctt gac ttt gcg gtt tta aat      1392
Ser Arg His Pro Leu Ser Thr Arg Asn Leu Asp Phe Ala Val Leu Asn
    450                 455                 460 ccg gcc ttt gtt gcc gtt aaa aac agg tat atg tat tgt gga gtt ggt      1440
Pro Ala Phe Val Ala Val Lys Asn Arg Tyr Met Tyr Cys Gly Val Gly
465                 470                 475                 480 gat ccg atg cca aag atc tct ggt gtg gtc aag cta gat gtg tca cta      1488
Asp Pro Met Pro Lys Ile Ser Gly Val Val Lys Leu Asp Val Ser Leu
                485                 490                 495 tcc gaa gca gac cgt cgc gaa tgc ata gtt gct agc cgg atg ttc ggg      1536
Ser Glu Ala Asp Arg Arg Glu Cys Ile Val Ala Ser Arg Met Phe Gly
            500                 505                 510 cct ggt tgt tac ggt ggt gaa cca ttc ttt gta gct agg gag cca gac      1584
Pro Gly Cys Tyr Gly Gly Glu Pro Phe Phe Val Ala Arg Glu Pro Asp
        515                 520                 525 aac ccc gat gcg gat gag gat gat ggg tat gtg gtt tct tat gtg cat      1632
Asn Pro Asp Ala Asp Glu Asp Asp Gly Tyr Val Val Ser Tyr Val His
    530                 535                 540 aac gag aac acc ggt gag tca aga ttc gtg gtg atg gac gct aag tca      1680
Asn Glu Asn Thr Gly Glu Ser Arg Phe Val Val Met Asp Ala Lys Ser
545                 550                 555                 560 ccg acg ctt gag atc gtc gat gcc gtg aag ctg ccc cac cgg gta cca      1728
Pro Thr Leu Glu Ile Val Asp Ala Val Lys Leu Pro His Arg Val Pro
                565                 570                 575 tat ggt ttt cat ggg ctc ttt gtt aga gaa agt gac gtt aac aag ttg      1776
Tyr Gly Phe His Gly Leu Phe Val Arg Glu Ser Asp Val Asn Lys Leu
            580                 585                 590 tgaaaattga atggtccaag attattgtaa aaagtagatg ctatagatat ttttccactc    1836
acgggcacat gatatatgtg tgtataatat atgtaaaatg tgatcgaaca taaataaagt    1896
aaaacacacc tatttccatg taaaaaaaaa aaaaaaaaaa aaaaaaaaaa aaaa          1950

<210> SEQ ID NO 2
<211> LENGTH: 592
<212> TYPE: PRT
<213> ORGANISM: Helianthus annuus

<400> SEQUENCE: 2

Met Asp Ser Leu Ser Ser Ser Phe Ile Ser Ile Phe Ser Gln Ser Asn
 1               5                  10                  15

Ser Thr Val Ser His Pro Pro Ser Ser Ser Pro Pro Ser Ala
            20                  25                  30

Leu Arg Val Phe Ser Val Arg Thr Glu Glu Lys Pro Glu Thr Val Thr
        35                  40                  45

Ser Thr Ala Thr Thr Lys Arg Pro Ser Gly Pro Lys Lys Gln Pro Thr
```

-continued

```
            50                  55                  60
Leu Asn Ile Arg Lys Arg Glu Ser Ser Val Val Asp Gln Ser Leu
 65                  70                  75                  80

Pro Ala Thr Ile Phe Asn Ala Phe Asp Ser Ile Ile Asn Asn Phe Ile
                     85                  90                  95

Asp Pro Pro Ala Arg Val Ser Val Asp Pro Lys His Val Leu Ser Asp
                100                 105                 110

Asn Phe Ser Pro Val Asp Glu Leu Pro Pro Thr Asp Cys Glu Val Ile
                115                 120                 125

Glu Gly Thr Leu Pro Ser Cys Leu Asp Gly Ala Tyr Phe Arg Asn Gly
                130                 135                 140

Pro Asn Pro Gln Phe Leu Pro Arg Gly Pro Tyr His Leu Phe Asp Gly
145                 150                 155                 160

Asp Gly Met Leu His Ala Ile Arg Ile Ser Asn Gly Lys Ala Ser Leu
                165                 170                 175

Cys Ser Arg Tyr Ile Lys Thr Tyr Lys Tyr Ser Ile Glu Lys Glu Ala
                180                 185                 190

Gly Phe Pro Ile Ile Pro Asn Val Phe Ser Gly Phe Asn Gly Val Thr
                195                 200                 205

Ala Ser Ala Ala Arg Met Ala Val Thr Ala Gly Arg Phe Leu Ala Gly
210                 215                 220

Gln Phe Asp Pro Thr Lys Gly Ile Gly Leu Ala Asn Thr Ser Leu Ala
225                 230                 235                 240

Phe Phe Gly Asn Arg Leu Phe Ala Leu Gly Glu Ser Asp Leu Pro Tyr
                245                 250                 255

Ala Val Lys Leu Ala Pro Asp Gly Asp Ile Val Thr Val Gly Arg Glu
                260                 265                 270

Asp Phe Asp Gly Lys Leu Phe Met Ser Met Thr Ala His Pro Lys Ile
                275                 280                 285

Asp Pro Val Thr Lys Glu Ala Phe Ala Phe Arg Tyr Gly Pro Val Pro
                290                 295                 300

Pro Phe Leu Thr Phe Phe Arg Phe Asn Glu Asn Gly Glu Lys Gln Ala
305                 310                 315                 320

Asp Val Pro Ile Phe Ser Met Thr Ser Pro Ser Phe Leu His Asp Phe
                325                 330                 335

Ala Ile Thr Lys Asn Tyr Ala Ile Phe Pro Glu Ile Gln Ile Gly Met
                340                 345                 350

Ser Pro Met Glu Met Leu Gly Gly Ser Pro Val Ser Ala Asp Ala
                355                 360                 365

Gly Lys Val Pro Arg Leu Gly Leu Ile Pro Arg Tyr Ala Lys Asp Glu
                370                 375                 380

Ser Glu Met Lys Trp Phe Glu Val Pro Gly Phe Asn Val Ile His Cys
385                 390                 395                 400

Ile Asn Ala Trp Glu Glu Asp Gly Gly Asp Thr Val Val Met Val Ala
                405                 410                 415

Pro Asn Ile Leu Ser Val Glu His Thr Leu Glu Arg Met Asp Leu Ile
                420                 425                 430

His Ala Ser Val Glu Lys Val Lys Ile Asn Leu Lys Thr Gly Met Val
                435                 440                 445

Ser Arg His Pro Leu Ser Thr Arg Asn Leu Asp Phe Ala Val Leu Asn
                450                 455                 460

Pro Ala Phe Val Ala Val Lys Asn Arg Tyr Met Tyr Cys Gly Val Gly
465                 470                 475                 480
```

```
Asp Pro Met Pro Lys Ile Ser Gly Val Val Lys Leu Asp Val Ser Leu
            485                 490                 495

Ser Glu Ala Asp Arg Arg Glu Cys Ile Val Ala Ser Arg Met Phe Gly
        500                 505                 510

Pro Gly Cys Tyr Gly Gly Glu Pro Phe Phe Val Ala Arg Glu Pro Asp
            515                 520                 525

Asn Pro Asp Ala Asp Glu Asp Asp Gly Tyr Val Val Ser Tyr Val His
        530                 535                 540

Asn Glu Asn Thr Gly Glu Ser Arg Phe Val Val Met Asp Ala Lys Ser
545                 550                 555                 560

Pro Thr Leu Glu Ile Val Asp Ala Val Lys Leu Pro His Arg Val Pro
                565                 570                 575

Tyr Gly Phe His Gly Leu Phe Val Arg Glu Ser Asp Val Asn Lys Leu
            580                 585                 590

<210> SEQ ID NO 3
<211> LENGTH: 1048
<212> TYPE: DNA
<213> ORGANISM: Helianthus annuus
<220> FEATURE:
<221> NAME/KEY: misc_feature
<222> LOCATION: (205)..(211)
<223> OTHER INFORMATION: MRE
<220> FEATURE:
<221> NAME/KEY: misc_feature
<222> LOCATION: (440)..(445)
<223> OTHER INFORMATION: W-box
<220> FEATURE:
<221> NAME/KEY: TATA_signal
<222> LOCATION: (1002)..(1007)

<400> SEQUENCE: 3
ctatagggca cgcgactata gggcacgcga ctatagggca cgcgactata gggcacgcga      60
ctatagggca cgcgactata gggcacgcga ctatagggca cgcgactata gggcacgcga     120
ctatagggca cgcgactata gggcacgcga ctatagggca cgcgactata gggcacgcgt     180
gcctggtggg tgggaaacag ttgagtttgg tgttgagatg ttaaggtgtg attaagtgtg     240
atgagtgatg accattgcaa gtgtaatagg gtaaatgtg atggatgtga tggagtaagg      300
tttgtcaaat ggtgatttgg tgtgacgtgt gatggagtga gggtatatag ggtgatcatc     360
actcatcaca ctccatcaca tcatcacacc cacatttgac acctcattcc atcacattt      420 actctatcac atttgcaatg gtcaacgtca aagttaaccc acacacacaa cacaaaccat     480
cacatcgcga tacttaccac aatttccatc ccatcaccaa gtgatacacc tcttaaggcg     540
gtgtagtacg gaacatcact catcacttgc acccatcacg tacccaaccc gataacctaa     600
taatgtgacg atatagtttt aatcggcaag aatgatacga taaaattaat taaatagaga     660
aacacaaaat cacaaatgca caactcttaa aattgaaaat aaaaaatatc gtgttgtttg     720
taaaactgaa gtatactaag ctacactaaa attcattaaa taaaaaaaat tgtattatta     780 actaataccct aaccccctcat aaccacaatt aatatatgtg gtaaagtaac aatttgacaa    840
aattcagatg aaaatatcag tcggatcata aatattttca tcagtttatt atggatatta     900
ttatggatat tataaattat tgaaaggaat aattacaaat atgaatatcg gatgtatttc     960
gtatggttaa cgtgactgat gggtcgtttt cgatgtttca ctataaaaac atgtcattgc    1020
tctgtggtaa agcatccggt accacact                                       1048

<210> SEQ ID NO 4
```

```
<211> LENGTH: 1656
<212> TYPE: DNA
<213> ORGANISM: Helianthus annuus
<220> FEATURE:
<221> NAME/KEY: CDS
<222> LOCATION: (56)..(1411)

<400> SEQUENCE: 4
ctccattcga tcccttttc gtttgctagt tcattataca ggtgttcgtg tcata atg         58
                                                            Met
                                                             1 gtt agc gat ggc aca caa agc caa aat caa caa tat ggc gtc gac aag        106
Val Ser Asp Gly Thr Gln Ser Gln Asn Gln Gln Tyr Gly Val Asp Lys
          5                  10                  15 gtt gac aac cga agt gaa aag gag aaa gcc atc gac gca tgg ctg ccg        154
Val Asp Asn Arg Ser Glu Lys Glu Lys Ala Ile Asp Ala Trp Leu Pro
     20                  25                  30 atc acc tca tca aga aac gca aaa tgg tgg tac gcc gcc ttc cac aac        202
Ile Thr Ser Ser Arg Asn Ala Lys Trp Trp Tyr Ala Ala Phe His Asn
 35                  40                  45 gtt acc gcc atg gtg gga gcg ggt gtt ctc agc ctc cct tac gca atg        250
Val Thr Ala Met Val Gly Ala Gly Val Leu Ser Leu Pro Tyr Ala Met
 50                  55                  60                  65 tcc gaa ctc gga tgg ggt cct ggt gtt gca gtt atg gtg ata tca tgg        298
Ser Glu Leu Gly Trp Gly Pro Gly Val Ala Val Met Val Ile Ser Trp
                 70                  75                  80 atc gta act gtc tac acg cta tgg caa atg gtc gaa atg cac gaa atg        346
Ile Val Thr Val Tyr Thr Leu Trp Gln Met Val Glu Met His Glu Met
             85                  90                  95 gtg cct gga aaa cga ttc gac aga tac cac gag ctc ggg cag cat gct        394
Val Pro Gly Lys Arg Phe Asp Arg Tyr His Glu Leu Gly Gln His Ala
        100                 105                 110 ttt ggt gaa aag cta ggt ctg tac att gtg gtt cca cag cag ttg gtt        442
Phe Gly Glu Lys Leu Gly Leu Tyr Ile Val Val Pro Gln Gln Leu Val
    115                 120                 125 gta gaa gtg agt cta tgc att att tat atg gtg act gga gga aaa tct        490
Val Glu Val Ser Leu Cys Ile Ile Tyr Met Val Thr Gly Gly Lys Ser
130                 135                 140                 145 tta cag aag ttt cat gat tta cta gtt cga caa gat gaa caa aaa gac        538
Leu Gln Lys Phe His Asp Leu Leu Val Arg Gln Asp Glu Gln Lys Asp
                150                 155                 160 att aga ctt acc ttt ttc atc atg ata tat ggg tct gtt cat ttt gtt        586
Ile Arg Leu Thr Phe Phe Ile Met Ile Tyr Gly Ser Val His Phe Val
            165                 170                 175 ctt tcg cat ctt ccc aac ttt aat tcg cta tct gga atc tcc ttg gct        634
Leu Ser His Leu Pro Asn Phe Asn Ser Leu Ser Gly Ile Ser Leu Ala
        180                 185                 190 gca gcc atc atg tct ctc agt tac tct act att gct tgg gga gcc tcc        682
Ala Ala Ile Met Ser Leu Ser Tyr Ser Thr Ile Ala Trp Gly Ala Ser
    195                 200                 205 ctg gat aag ggt gtg caa cca aac gtg gaa tac ggc tac aaa gct aag        730
Leu Asp Lys Gly Val Gln Pro Asn Val Glu Tyr Gly Tyr Lys Ala Lys
210                 215                 220                 225 agc acg act ggg acc gtg ttc aat ttc cta agt gca tta ggt gac atg        778
Ser Thr Thr Gly Thr Val Phe Asn Phe Leu Ser Ala Leu Gly Asp Met
                230                 235                 240 gca ttt gca tac gca ggc cac aat gtg gtg ttg gaa att caa gcc acc        826
Ala Phe Ala Tyr Ala Gly His Asn Val Val Leu Glu Ile Gln Ala Thr
            245                 250                 255 att cca tca act ccg gag aag cct tca aaa ggt cct atg tgg aag gga        874
Ile Pro Ser Thr Pro Glu Lys Pro Ser Lys Gly Pro Met Trp Lys Gly
```

```
                260                 265                 270
gtg gtt gtt gcc tat ata gtt att gcc tta tgc tat ttc cca gtt gct     922
Val Val Val Ala Tyr Ile Val Ile Ala Leu Cys Tyr Phe Pro Val Ala
    275                 280                 285 ttt att gga tac tgg gtg ttt gga aat ggg gtt gat gat aat atc ctt     970
Phe Ile Gly Tyr Trp Val Phe Gly Asn Gly Val Asp Asp Asn Ile Leu
290                 295                 300                 305 att act tta gaa aag ccc aca tgg cta att gcc atg gct aat atg ttc    1018
Ile Thr Leu Glu Lys Pro Thr Trp Leu Ile Ala Met Ala Asn Met Phe
                310                 315                 320 gtt gta gtt cac gtt atc ggt agt tac cag ctc tat gca atg ccg gta    1066
Val Val Val His Val Ile Gly Ser Tyr Gln Leu Tyr Ala Met Pro Val
    325                 330                 335 ttt gat atg atg gaa acc ttg ttg gta aag aag ttg aac ttt gcc cct    1114
Phe Asp Met Met Glu Thr Leu Leu Val Lys Lys Leu Asn Phe Ala Pro
        340                 345                 350 agc ttt atg ctt cgg ttt atc aca agg aat gtg tat gtt gca ttc aca    1162
Ser Phe Met Leu Arg Phe Ile Thr Arg Asn Val Tyr Val Ala Phe Thr
            355                 360                 365 atg ttc gta gga att tgc ttc cct ttc ttt ggc gga cta ctt gga ttc    1210
Met Phe Val Gly Ile Cys Phe Pro Phe Phe Gly Gly Leu Leu Gly Phe
370                 375                 380                 385 ttt gga gga ctt gca ttt gcc cca aca aca tac ttt ttg cct tgc atc    1258
Phe Gly Gly Leu Ala Phe Ala Pro Thr Thr Tyr Phe Leu Pro Cys Ile
                390                 395                 400 atg tgg ctt tgc ata tgt aaa cct aga aga tgg agc tta tct tgg ttt    1306
Met Trp Leu Cys Ile Cys Lys Pro Arg Arg Trp Ser Leu Ser Trp Phe
    405                 410                 415 acc aat tgg atc tgt att gta ctt gga gtt gtt ttg atg gtg gta gca    1354
Thr Asn Trp Ile Cys Ile Val Leu Gly Val Val Leu Met Val Val Ala
        420                 425                 430 cct att ggg ggg tta aga tcg atc atc gtt caa gcc aaa acc tat aag    1402
Pro Ile Gly Gly Leu Arg Ser Ile Ile Val Gln Ala Lys Thr Tyr Lys
            435                 440                 445 ttt ttc tca taagcatcaa gttacgtctg ggatttagcc tgtgatgata            1451
Phe Phe Ser
450 ataaacgctg ctcaggaaat gttatagtta aaagagtgcg cgtgtttagt tctaccaaag  1511 agttacctgc acaaagttca gctataatct tctacttaac aagttattgt atctgttcca  1571 gctttgcttg taatatatgg gaagatttta tcaaatacag agggatgata tttacatgtt  1631 tacacttata aaaaaaaaaa aaaaa                                        1656

<210> SEQ ID NO 5
<211> LENGTH: 452
<212> TYPE: PRT
<213> ORGANISM: Helianthus annuus

<400> SEQUENCE: 5

Met Val Ser Asp Gly Thr Gln Ser Gln Asn Gln Gln Tyr Gly Val Asp
 1               5                  10                  15

Lys Val Asp Asn Arg Ser Glu Lys Glu Lys Ala Ile Asp Ala Trp Leu
                20                  25                  30

Pro Ile Thr Ser Ser Arg Asn Ala Lys Trp Trp Tyr Ala Ala Phe His
            35                  40                  45

Asn Val Thr Ala Met Val Gly Ala Gly Val Leu Ser Leu Pro Tyr Ala
        50                  55                  60

Met Ser Glu Leu Gly Trp Gly Pro Gly Val Ala Val Met Val Ile Ser
```

```
             65                  70                  75                  80
Trp Ile Val Thr Val Tyr Thr Leu Trp Gln Met Val Glu Met His Glu
                     85                  90                  95
Met Val Pro Gly Lys Arg Phe Asp Arg Tyr His Glu Leu Gly Gln His
                100                 105                 110
Ala Phe Gly Glu Lys Leu Gly Leu Tyr Ile Val Pro Gln Gln Leu
            115                 120                 125
Val Val Glu Val Ser Leu Cys Ile Ile Tyr Met Val Thr Gly Gly Lys
130                 135                 140
Ser Leu Gln Lys Phe His Asp Leu Leu Val Arg Gln Asp Glu Gln Lys
145                 150                 155                 160
Asp Ile Arg Leu Thr Phe Phe Ile Met Ile Tyr Gly Ser Val His Phe
                165                 170                 175
Val Leu Ser His Leu Pro Asn Phe Asn Ser Leu Ser Gly Ile Ser Leu
                180                 185                 190
Ala Ala Ala Ile Met Ser Leu Ser Tyr Ser Thr Ile Ala Trp Gly Ala
                195                 200                 205
Ser Leu Asp Lys Gly Val Gln Pro Asn Val Glu Tyr Gly Tyr Lys Ala
210                 215                 220
Lys Ser Thr Thr Gly Thr Val Phe Asn Phe Leu Ser Ala Leu Gly Asp
225                 230                 235                 240
Met Ala Phe Ala Tyr Ala Gly His Asn Val Val Leu Glu Ile Gln Ala
                245                 250                 255
Thr Ile Pro Ser Thr Pro Glu Lys Pro Ser Lys Gly Pro Met Trp Lys
                260                 265                 270
Gly Val Val Ala Tyr Ile Val Ile Ala Leu Cys Tyr Phe Pro Val
            275                 280                 285
Ala Phe Ile Gly Tyr Trp Val Phe Gly Asn Gly Val Asp Asp Asn Ile
            290                 295                 300
Leu Ile Thr Leu Glu Lys Pro Thr Trp Leu Ile Ala Met Ala Asn Met
305                 310                 315                 320
Phe Val Val His Val Ile Gly Ser Tyr Gln Leu Tyr Ala Met Pro
                325                 330                 335
Val Phe Asp Met Met Glu Thr Leu Leu Val Lys Lys Leu Asn Phe Ala
                340                 345                 350
Pro Ser Phe Met Leu Arg Phe Ile Thr Arg Asn Val Tyr Val Ala Phe
            355                 360                 365
Thr Met Phe Val Gly Ile Cys Phe Pro Phe Phe Gly Leu Leu Gly
            370                 375                 380
Phe Phe Gly Gly Leu Ala Phe Ala Pro Thr Thr Tyr Phe Leu Pro Cys
385                 390                 395                 400
Ile Met Trp Leu Cys Ile Cys Lys Pro Arg Arg Trp Ser Leu Ser Trp
                405                 410                 415
Phe Thr Asn Trp Ile Cys Ile Val Leu Gly Val Val Leu Met Val Val
                420                 425                 430
Ala Pro Ile Gly Gly Leu Arg Ser Ile Ile Val Gln Ala Lys Thr Tyr
            435                 440                 445
Lys Phe Phe Ser
    450

<210> SEQ ID NO 6
<211> LENGTH: 865
<212> TYPE: DNA
<213> ORGANISM: Helianthus annuus
```

```
<220> FEATURE:
<221> NAME/KEY: CDS
<222> LOCATION: (1)..(519)

<400> SEQUENCE: 6 atg cag gtt gta tca gca aca aca gca ttg cat gat gag aaa att gag        48
Met Gln Val Val Ser Ala Thr Thr Ala Leu His Asp Glu Lys Ile Glu
 1               5                  10                  15 gag aaa tcg aat gtc gaa atc gga gag gac ata aag agc aca aat gat        96
Glu Lys Ser Asn Val Glu Ile Gly Glu Asp Ile Lys Ser Thr Asn Asp
             20                  25                  30 caa gaa aca aca cca caa cca caa gaa gac cag ccc cct aaa gaa aaa       144
Gln Glu Thr Thr Pro Gln Pro Gln Glu Asp Gln Pro Pro Lys Glu Lys
         35                  40                  45 cct ctt gat gac ata act gtt gca cct gaa cct gat gta gct gct cct       192
Pro Leu Asp Asp Ile Thr Val Ala Pro Glu Pro Asp Val Ala Ala Pro
 50                  55                  60 gaa gtc cta gaa gcc aaa cca gaa cca aaa gcc gaa cca gaa cca gaa       240
Glu Val Leu Glu Ala Lys Pro Glu Pro Lys Ala Glu Pro Glu Pro Glu
 65                  70                  75                  80 gcc gaa ccg gaa gcc ctt gca gct gag gtt gaa acc aaa gtg gtt cta       288
Ala Glu Pro Glu Ala Leu Ala Ala Glu Val Glu Thr Lys Val Val Leu
                 85                  90                  95 aaa gaa gaa gaa gaa gaa ggt aag gat att cct gtg gat cag cct gca       336
Lys Glu Glu Glu Glu Glu Gly Lys Asp Ile Pro Val Asp Gln Pro Ala
            100                 105                 110 aag gtg gca ccc gag cca tgt gtg gag gaa gag gct aaa gaa acc aaa       384
Lys Val Ala Pro Glu Pro Cys Val Glu Glu Ala Lys Glu Thr Lys
        115                 120                 125 gaa cca gaa ggt gaa ccg gtg gaa acc aaa acc gaa acc gaa gcg gaa       432
Glu Pro Glu Gly Glu Pro Val Glu Thr Lys Thr Glu Thr Glu Ala Glu
    130                 135                 140 gcg gta ccc gag ccg acc gag gtg gca aag agt gaa ggt gaa ccg aag       480
Ala Val Pro Glu Pro Thr Glu Val Ala Lys Ser Glu Gly Glu Pro Lys
145                 150                 155                 160 gag gag tct gag aag aaa gaa gaa ggt gca gca gct gag tagatcattt        529
Glu Glu Ser Glu Lys Lys Glu Glu Gly Ala Ala Ala Glu
                165                 170 gaagtgtgca tgcttcttgt ggatctattt ggttattatc tttagtttga ttttgattaa     589
aagtttgtga aattccagct gggataggtt attgtgtaat caaaggcagg cttggccacg     649
tggcaagcat gggttgggta gaaactaggg tttatttaa gggaacatgc aggtcagggt      709
ttgctggtaa taaactccca ggctggattt gtttaatttt catgaataaa gtgtgtatgt     769
ttttatgtta ttctaaggtg gcttacctgt aatgctttgt ccttgcagtt atatatgagt     829
tactttttag tgatcaatta aaaaaaaaaa aaaaaa                               865

<210> SEQ ID NO 7
<211> LENGTH: 173
<212> TYPE: PRT
<213> ORGANISM: Helianthus annuus

<400> SEQUENCE: 7

Met Gln Val Val Ser Ala Thr Thr Ala Leu His Asp Glu Lys Ile Glu
 1               5                  10                  15

Glu Lys Ser Asn Val Glu Ile Gly Glu Asp Ile Lys Ser Thr Asn Asp
             20                  25                  30

Gln Glu Thr Thr Pro Gln Pro Gln Glu Asp Gln Pro Pro Lys Glu Lys
         35                  40                  45
```

```
Pro Leu Asp Asp Ile Thr Val Ala Pro Glu Pro Asp Val Ala Ala Pro
    50                  55                  60

Glu Val Leu Glu Ala Lys Pro Glu Pro Lys Ala Glu Pro Glu Pro Glu
 65                  70                  75                  80

Ala Glu Pro Glu Ala Leu Ala Ala Glu Val Glu Thr Lys Val Val Leu
                 85                  90                  95

Lys Glu Glu Glu Glu Gly Lys Asp Ile Pro Val Asp Gln Pro Ala
                100                 105                 110

Lys Val Ala Pro Glu Pro Cys Val Glu Glu Ala Lys Glu Thr Lys
            115                 120                 125

Glu Pro Glu Gly Glu Pro Val Glu Thr Lys Thr Glu Thr Glu Ala Glu
    130                 135                 140

Ala Val Pro Glu Pro Thr Glu Val Ala Lys Ser Glu Gly Glu Pro Lys
145                 150                 155                 160

Glu Glu Ser Glu Lys Lys Glu Glu Gly Ala Ala Ala Glu
                165                 170
```

<210> SEQ ID NO 8
<211> LENGTH: 1267
<212> TYPE: DNA
<213> ORGANISM: Helianthus annuus
<220> FEATURE:
<221> NAME/KEY: misc_binding
<222> LOCATION: (846)..(850)
<223> OTHER INFORMATION: bZIP protein-binding motif
<220> FEATURE:
<221> NAME/KEY: misc_feature
<222> LOCATION: (537)..(540)
<223> OTHER INFORMATION: W-box

<400> SEQUENCE: 8

```
aattaacaat ggttcagatc tgttcttacg gttcttataa ttagcactgt ttgtacagga      60
tctcaaccca ataatatat  aatggattat aaaatataat acaatgccgg acaaatatt     120
acacattgtc gaaagaaga  cataatagta aaaaatgtc  aagaaaaaa  agacataat     180
agtaaaaaaa cacacaaaga gacaaaaaac cgaattcaag ctcgagcttt aatctctaaa    240
attaaaatta gccgagctct tattgtgttt acacccctaa atagggctat aaacgaaccg    300
aacgaacaga aacaagacct tgttcatgtt cgtttgttaa atatgtgtgt tcatgaacat    360
ttaacaaaca cgattttatg ttcatgttcg tttgtcaagg atgtgtactt gtttgtgttt    420
gtttgttaac tttaggcaat attgataaac accaatgagc acaaactaat gttcatgaac    480
acaaatggaa acaaatgaac acaataagc  attcaagaac aaaatattta atacactgac    540
acttattaaa tattttattt gtcgaagttt tgaagtattt atataaaata taaaaactac    600
aaacactaac gcgctatcga acacaaatga acacgttacc gaacgttcac gaacataaat    660
gaacgaacac gacctctgct catgtttgtt catttaacta acgaacgga  attttttgtt    720
cgtgttcgtt tgtttaataa acgaacgaaa acaaacaaac ttcccatcga ataatttacg    780
aactgttcgc caaacatttg atttgtttgc agcctaaccc taaactcatc caactaatgt    840
aatcatgacg gattaaaaag taaaaagaa  aatgtaaaag cagtattaaa gtattcatta    900
aaaattcaga atcaagata  tcaatcacat gaaatatgta aaatacaccc tgtgaatgat    960
ctctctcatc aatcacactt ctatataaac ccatgtttcc ccaccatttc ttttcacccct  1020
caaaactcca ttcatcacca tctttctatt cttcttcttc ttctaattcc ctgcttttgt   1080
aaccatggct actgctcagg taacattcta ttttgtaact aaacaattaa tgtgcatata   1140
cacaaaggaa atagttgcct tgaagtcttg aacatatttt cataattcat ttgaaagtga   1200
```

```
tcatttattc attttctgct tgttagctag ataagttgat tacacaagat tatctatata    1260
tatgatg                                                               1267
```

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 9

```
gcgattaagt tgggtaacgc cagggt                                          26
```

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 10

```
tccggctcgt atgttgtgtg gaattg                                          26
```

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 11

```
gctagatgtg tcactatccg aagc                                            24
```

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 12

```
gtctggctcc ctagctacaa agaa                                            24
```

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 13

```
atcgacgatc tcaagcgtcg gtgact                                          26
```

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide primer -continued

<400> SEQUENCE: 14
ggctccccaa gcaatagtag agta                                          24

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 15
ccacagcagt tggttgtaga ag                                            22

<210> SEQ ID NO 16
<211> LENGTH: 26
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 16
caaaagccga accagaacca gaagcc                                        26

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 17
tttggtttca acctcagctg caaggg                                        26

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 18
ccctgctttt gtaaccatgg ctactgctca                                    30

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 19
gcgtagtttt tggtgatggc gaagtc                                        26

<210> SEQ ID NO 20
<211> LENGTH: 595
<212> TYPE: PRT
<213> ORGANISM: Arabidopsis thaliana

<400> SEQUENCE: 20

Met Asp Ser Val Ser Ser Ser Ser Phe Leu Ser Ser Thr Phe Ser Leu
 1               5                   10                  15

```
His His Ser Leu Leu Arg Arg Arg Ser Ser Pro Thr Leu Leu Arg
             20                  25                  30

Ile Asn Ser Ala Val Val Glu Glu Arg Ser Pro Ile Thr Asn Pro Ser
         35                  40                  45

Asp Asn Asn Asp Arg Arg Asn Lys Pro Lys Thr Leu His Asn Arg Thr
     50                  55                  60

Asn His Thr Leu Val Ser Ser Pro Pro Lys Leu Arg Pro Glu Met Thr
 65                  70                  75                  80

Leu Ala Thr Ala Leu Phe Thr Thr Val Glu Asp Val Ile Asn Thr Phe
                 85                  90                  95

Ile Asp Pro Pro Ser Arg Pro Ser Val Asp Pro Lys His Val Leu Ser
             100                 105                 110

Asp Asn Phe Ala Pro Val Leu Asp Glu Leu Pro Pro Thr Asp Cys Glu
         115                 120                 125

Ile Ile His Gly Thr Leu Pro Leu Ser Leu Asn Gly Ala Tyr Ile Arg
     130                 135                 140

Asn Gly Pro Asn Pro Gln Phe Leu Pro Arg Gly Pro Tyr His Leu Phe
145                 150                 155                 160

Asp Gly Asp Gly Met Leu His Ala Ile Lys Ile His Asn Gly Lys Ala
                 165                 170                 175

Thr Leu Cys Ser Arg Tyr Val Lys Thr Tyr Lys Tyr Asn Val Glu Lys
             180                 185                 190

Gln Thr Gly Ala Pro Val Met Pro Asn Val Phe Ser Gly Phe Asn Gly
         195                 200                 205

Val Thr Ala Ser Val Ala Arg Gly Ala Leu Thr Ala Ala Arg Val Leu
     210                 215                 220

Thr Gly Gln Tyr Asn Pro Val Asn Gly Ile Gly Leu Ala Asn Thr Ser
225                 230                 235                 240

Leu Ala Phe Phe Ser Asn Arg Leu Phe Ala Leu Gly Glu Ser Asp Leu
                 245                 250                 255

Pro Tyr Ala Val Arg Leu Thr Glu Ser Gly Asp Ile Glu Thr Ile Gly
             260                 265                 270

Arg Tyr Asp Phe Asp Gly Lys Leu Ala Met Ser Met Thr Ala His Pro
         275                 280                 285

Lys Thr Asp Pro Ile Thr Gly Glu Thr Phe Ala Phe Arg Tyr Gly Pro
     290                 295                 300

Val Pro Pro Phe Leu Thr Tyr Phe Arg Phe Asp Ser Ala Gly Lys Lys
305                 310                 315                 320

Gln Arg Asp Val Pro Ile Phe Ser Met Thr Ser Pro Ser Phe Leu His
                 325                 330                 335

Asp Phe Ala Ile Thr Lys Arg His Ala Ile Phe Ala Glu Ile Gln Leu
             340                 345                 350

Gly Met Arg Met Asn Met Leu Asp Leu Val Leu Glu Gly Gly Ser Pro
         355                 360                 365

Val Gly Thr Asp Asn Gly Lys Thr Pro Arg Leu Gly Val Ile Pro Lys
     370                 375                 380

Tyr Ala Gly Asp Glu Ser Glu Met Lys Trp Phe Glu Val Pro Gly Phe
385                 390                 395                 400

Asn Ile Ile His Ala Ile Asn Ala Trp Asp Glu Asp Gly Asn Ser
                 405                 410                 415

Val Val Leu Ile Ala Pro Asn Ile Met Ser Ile Glu His Thr Leu Glu
             420                 425                 430
```

-continued

```
Arg Met Asp Leu Val His Ala Leu Val Glu Lys Val Lys Ile Asp Leu
        435                 440                 445

Val Thr Gly Ile Val Arg Arg His Pro Ile Ser Ala Arg Asn Leu Asp
        450                 455                 460

Phe Ala Val Ile Asn Pro Ala Phe Leu Gly Arg Cys Ser Arg Tyr Val
465                 470                 475                 480

Tyr Ala Ala Ile Gly Asp Pro Met Pro Lys Ile Ser Gly Val Val Lys
                485                 490                 495

Leu Asp Val Ser Lys Gly Asp Arg Asp Asp Cys Thr Val Ala Arg Arg
                500                 505                 510

Met Tyr Gly Ser Gly Cys Tyr Gly Gly Glu Pro Phe Phe Val Ala Arg
                515                 520                 525

Asp Pro Gly Asn Pro Glu Ala Glu Glu Asp Gly Tyr Val Val Thr
        530                 535                 540

Tyr Val His Asp Glu Val Thr Gly Glu Ser Lys Phe Leu Val Met Asp
545                 550                 555                 560

Ala Lys Ser Pro Glu Leu Glu Ile Val Ala Ala Val Arg Leu Pro Arg
                565                 570                 575

Arg Val Pro Tyr Gly Phe His Gly Leu Phe Val Lys Glu Ser Asp Leu
                580                 585                 590

Asn Lys Leu
        595

<210> SEQ ID NO 21
<211> LENGTH: 446
<212> TYPE: PRT
<213> ORGANISM: Malus domestica

<400> SEQUENCE: 21

Met Ala Pro Thr Arg Asn Thr Phe Arg Val Gly Pro Thr Thr Cys Ser
1               5                   10                  15

Thr Gly Thr Ala Cys Phe Thr Pro Leu Gly Ser Pro Glu Ala Ala Arg
                20                  25                  30

Cys Ser Ala Ala Asp Met Ser Arg Pro Thr Ser Thr Pro Leu Ser Val
            35                  40                  45

Thr Pro Ala Thr Leu Tyr Phe Pro Thr Ser Ser Leu Ala Ser Thr Ala
        50                  55                  60

Ser Pro Leu Pro Pro His Val Ala Leu Ser Ala Ala Arg Val Leu Thr
65                  70                  75                  80

Gly Gln Tyr Asn Pro Ala Asn Gly Ile Gly Leu Ala Asn Thr Ser Leu
                85                  90                  95

Ala Phe Phe Gly Asp Arg Leu Tyr Ala Leu Gly Glu Ser Asp Leu Pro
            100                 105                 110

Tyr Ser Leu Arg Leu Thr Ser Asn Gly Asp Ile Glu Thr Leu Gly Arg
        115                 120                 125

His Asp Phe Asp Gly Lys Leu Ser Met Asn Met Thr Ala His Pro Lys
    130                 135                 140

Ile Asp Pro Asp Thr Gly Glu Ala Phe Ala Phe Arg Tyr Gly Phe Ile
145                 150                 155                 160

Arg Pro Phe Leu Thr Tyr Phe Arg Phe Asp Ser Asn Gly Val Lys Gln
                165                 170                 175

Pro Asp Val Pro Ile Phe Ser Met Val Thr Pro Thr Phe Leu His Asp
            180                 185                 190

Phe Ala Ile Thr Lys Lys His Ala Ile Phe Ala Asp Ile Gln Ile Gly
        195                 200                 205
```

```
Leu Asn Leu Ile Asp Met Ile Thr Lys Arg Ala Thr Pro Phe Gly Leu
            210                 215                 220

Asp Pro Ser Lys Val Pro Arg Ile Gly Val Ile Pro Leu Tyr Ala Lys
225                 230                 235                 240

Asp Glu Ser Glu Met Arg Trp Phe Glu Val Pro Gly Phe Asn Gly Val
                245                 250                 255

His Ala Thr Asn Ala Trp Asp Glu Asp Ala Ile Val Met Val Ala
                260                 265                 270

Pro Asn Val Leu Ser Ala Glu His Val Leu Glu Arg Val Asp Leu Val
            275                 280                 285

His Cys Leu Val Glu Lys Val Arg Ile Asp Leu Lys Thr Gly Ile Val
            290                 295                 300

Thr Arg Gln Pro Ile Ser Thr Arg Asn Leu Asp Phe Ala Val Ile Asn
305                 310                 315                 320

Pro Ala Tyr Leu Gly Arg Lys Asn Lys Tyr Val Tyr Ala Ala Glu Gly
                325                 330                 335

Asp Pro Met Pro Lys Ile Ser Gly Val Val Lys Leu Asp Val Ser Asn
                340                 345                 350

Val Glu His Lys Glu Cys Ile Val Ala Ser Arg Met Phe Gly Pro Gly
                355                 360                 365

Cys Tyr Gly Gly Glu Pro Phe Phe Val Ala Arg Glu Pro Glu Asn Pro
    370                 375                 380

Glu Ala Asp Glu Asp Asn Gly Phe Leu Val Ser Tyr Val His Asp Glu
385                 390                 395                 400

Lys Ala Gly Glu Ser Arg Phe Leu Val Met Asp Ala Lys Ser Pro Gln
                405                 410                 415

Leu Asp Ile Val Ala Ala Val Arg Met Pro Arg Arg Val Pro Tyr Gly
                420                 425                 430

Phe His Gly Leu Phe Val Arg Glu Ser Asp Leu Asn Asn Leu
            435                 440                 445

<210> SEQ ID NO 22
<211> LENGTH: 605
<212> TYPE: PRT
<213> ORGANISM: Lycopersicon esculentum

<400> SEQUENCE: 22

Met Ala Thr Thr Thr Ser His Ala Thr Asn Thr Trp Ile Lys Thr Lys
1               5                   10                  15

Leu Ser Met Pro Ser Ser Lys Glu Phe Gly Phe Ala Ser Asn Ser Ile
                20                  25                  30

Ser Leu Leu Lys Asn Gln His Asn Arg Gln Ser Leu Asn Ile Asn Ser
            35                  40                  45

Ser Leu Gln Ala Pro Pro Ile Leu His Phe Pro Lys Gln Ser Ser Asn
        50                  55                  60

Tyr Gln Thr Pro Lys Asn Asn Thr Ile Ser His Pro Lys Gln Glu Asn
65                  70                  75                  80

Asn Asn Ser Ser Ser Ser Thr Ser Lys Trp Asn Leu Val Gln Lys
                85                  90                  95

Ala Ala Ala Met Ala Leu Asp Ala Val Glu Ser Ala Leu Thr Lys His
                100                 105                 110

Glu Leu Glu His Pro Leu Pro Lys Thr Ala Asp Pro Arg Val Gln Ile
            115                 120                 125

Ser Gly Asn Phe Ala Pro Val Pro Glu Asn Pro Val Cys Gln Ser Leu
```

-continued

```
            130                 135                 140
Pro Val Thr Gly Lys Ile Pro Lys Cys Val Gln Gly Val Tyr Val Arg
145                 150                 155                 160
Asn Gly Ala Asn Pro Leu Phe Glu Pro Thr Ala Gly His His Phe Phe
                165                 170                 175
Asp Gly Asp Gly Met Val His Ala Val Gln Phe Lys Asn Gly Ser Ala
                180                 185                 190
Ser Tyr Ala Cys Arg Phe Thr Glu Thr Glu Arg Leu Val Gln Glu Lys
                195                 200                 205
Ala Leu Gly Arg Pro Val Phe Pro Lys Ala Ile Gly Glu Leu His Gly
        210                 215                 220
His Ser Gly Ile Ala Arg Leu Met Leu Phe Tyr Ala Arg Gly Leu Phe
225                 230                 235                 240
Gly Leu Val Asp His Ser Lys Gly Thr Gly Val Ala Asn Ala Gly Leu
                245                 250                 255
Val Tyr Phe Asn Asn Arg Leu Leu Ala Met Ser Glu Asp Asp Leu Pro
                260                 265                 270
Tyr His Val Lys Val Thr Pro Thr Gly Asp Leu Lys Thr Glu Gly Arg
            275                 280                 285
Phe Asp Phe Asp Gly Gln Leu Lys Ser Thr Met Ile Ala His Pro Lys
290                 295                 300
Leu Asp Pro Val Ser Gly Glu Leu Phe Ala Leu Ser Tyr Asp Val Ile
305                 310                 315                 320
Gln Lys Pro Tyr Leu Lys Tyr Phe Arg Phe Ser Lys Asn Gly Glu Lys
                325                 330                 335
Ser Asn Asp Val Glu Ile Pro Val Glu Asp Pro Thr Met Met His Asp
            340                 345                 350
Phe Ala Ile Thr Glu Asn Phe Val Val Ile Pro Asp Gln Gln Val Val
            355                 360                 365
Phe Lys Met Ser Glu Met Ile Arg Gly Gly Ser Pro Val Val Tyr Asp
370                 375                 380
Lys Asn Lys Val Ser Arg Phe Gly Ile Leu Asp Lys Tyr Ala Lys Asp
385                 390                 395                 400
Gly Ser Asp Leu Lys Trp Val Glu Val Pro Asp Cys Phe Cys Phe His
                405                 410                 415
Leu Trp Asn Ala Trp Glu Glu Ala Thr Asp Glu Ile Val Val Ile
                420                 425                 430
Gly Ser Cys Met Thr Pro Pro Asp Ser Ile Phe Asn Glu Cys Asp Glu
            435                 440                 445
Gly Leu Lys Ser Val Leu Ser Glu Ile Arg Leu Asn Leu Lys Thr Gly
        450                 455                 460
Lys Ser Thr Arg Lys Ser Ile Ile Glu Asn Pro Asp Glu Gln Val Asn
465                 470                 475                 480
Leu Glu Ala Gly Met Val Asn Arg Asn Lys Leu Gly Arg Lys Thr Glu
                485                 490                 495
Tyr Ala Tyr Leu Ala Ile Ala Glu Pro Trp Pro Lys Val Ser Gly Phe
                500                 505                 510
Ala Lys Val Asn Leu Phe Thr Gly Glu Val Glu Lys Phe Ile Tyr Gly
            515                 520                 525
Asp Asn Lys Tyr Gly Gly Glu Pro Leu Phe Leu Pro Arg Asp Pro Asn
            530                 535                 540
Ser Lys Glu Glu Asp Asp Gly Tyr Ile Leu Ala Phe Val His Asp Glu
545                 550                 555                 560
```

Lys Glu Trp Lys Ser Glu Leu Gln Ile Val Asn Ala Met Ser Leu Lys
                565                 570                 575

Leu Glu Ala Thr Val Lys Leu Pro Ser Arg Val Pro Tyr Gly Phe His
            580                 585                 590

Gly Thr Phe Ile Asn Ala Asn Asp Leu Ala Asn Gln Ala
        595                 600                 605

<210> SEQ ID NO 23
<211> LENGTH: 604
<212> TYPE: PRT
<213> ORGANISM: Zea mays

<400> SEQUENCE: 23

Met Gln Gly Leu Ala Pro Pro Thr Ser Val Ser Ile His Arg His Leu
 1               5                  10                  15

Pro Ala Arg Ser Arg Ala Arg Ala Ser Asn Ser Val Arg Phe Ser Pro
            20                  25                  30

Arg Ala Val Ser Ser Val Pro Pro Ala Glu Cys Leu Gln Ala Pro Phe
        35                  40                  45

His Lys Pro Val Ala Asp Leu Pro Ala Pro Ser Arg Lys Pro Ala Ala
    50                  55                  60

Ile Ala Val Pro Gly His Ala Ala Pro Arg Lys Ala Glu Gly Gly
 65                  70                  75                  80

Lys Lys Gln Leu Asn Leu Phe Gln Arg Ala Ala Ala Ala Leu Asp
                85                  90                  95

Ala Phe Glu Glu Gly Phe Val Ala Asn Val Leu Glu Arg Pro His Gly
            100                 105                 110

Leu Pro Ser Thr Ala Asp Pro Ala Val Gln Ile Ala Gly Asn Phe Ala
        115                 120                 125

Pro Val Gly Glu Arg Pro Pro Val His Glu Leu Pro Val Ser Gly Arg
    130                 135                 140

Ile Pro Pro Phe Ile Asp Gly Val Tyr Ala Arg Asn Gly Ala Asn Pro
145                 150                 155                 160

Cys Phe Asp Pro Val Ala Gly His His Leu Phe Asp Gly Asp Gly Met
                165                 170                 175

Val His Ala Leu Arg Ile Arg Asn Gly Ala Ala Glu Ser Tyr Ala Cys
            180                 185                 190

Arg Phe Thr Glu Thr Ala Arg Leu Arg Gln Glu Arg Ala Ile Gly Arg
        195                 200                 205

Pro Val Phe Pro Lys Ala Ile Gly Glu Leu His Gly His Ser Gly Ile
    210                 215                 220

Ala Arg Leu Ala Leu Phe Tyr Ala Arg Ala Ala Cys Gly Leu Val Asp
225                 230                 235                 240

Pro Ser Ala Gly Thr Gly Val Ala Asn Ala Gly Leu Val Tyr Phe Asn
                245                 250                 255

Gly Arg Leu Leu Ala Met Ser Glu Asp Asp Leu Pro Tyr His Val Arg
            260                 265                 270

Val Ala Asp Asp Gly Asp Leu Glu Thr Val Gly Arg Tyr Asp Phe Asp
        275                 280                 285

Gly Gln Leu Gly Cys Ala Met Ile Ala His Pro Lys Leu Asp Pro Ala
    290                 295                 300

Thr Gly Glu Leu His Ala Leu Ser Tyr Asp Val Ile Lys Arg Pro Tyr
305                 310                 315                 320

Leu Lys Tyr Phe Tyr Phe Arg Pro Asp Gly Thr Lys Ser Asp Asp Val

```
                         325                 330                 335
Glu Ile Pro Leu Glu Gln Pro Thr Met Ile His Asp Phe Ala Ile Thr
                340                 345                 350
Glu Asn Phe Val Val Pro Asp His Gln Val Phe Lys Leu Gln
            355                 360                 365
Glu Met Leu Arg Gly Gly Ser Pro Val Val Leu Asp Lys Glu Lys Thr
        370                 375                 380
Ser Arg Phe Gly Val Leu Pro Lys His Ala Ala Asp Ala Ser Glu Met
385                 390                 395                 400
Ala Trp Val Asp Val Pro Asp Cys Phe Cys Phe His Leu Trp Asn Ala
                405                 410                 415
Trp Glu Asp Glu Ala Thr Gly Glu Val Val Ile Gly Ser Cys Met
            420                 425                 430
Thr Pro Ala Asp Ser Ile Phe Asn Glu Ser Asp Glu Arg Leu Glu Ser
            435                 440                 445
Val Leu Thr Glu Ile Arg Leu Asp Ala Arg Thr Gly Arg Ser Thr Arg
        450                 455                 460
Arg Ala Val Leu Pro Pro Ser Gln Gln Glu Asn Leu Glu Val Gly Met
465                 470                 475                 480
Val Asn Arg Asn Leu Leu Gly Arg Glu Ser Arg Tyr Ala Tyr Leu Ala
                485                 490                 495
Val Ala Glu Pro Trp Pro Lys Glu Ser Gly Phe Ala Lys Glu Asp Leu
                500                 505                 510
Ser Thr Gly Glu Leu Thr Lys Phe Glu Tyr Gly Gly Arg Phe Gly
            515                 520                 525
Gly Glu Pro Cys Phe Val Pro Met Asp Pro Ala Ala His Pro Arg
            530                 535                 540
Gly Glu Asp Asp Gly Tyr Val Leu Thr Phe His Asp Glu Arg Ala
545                 550                 555                 560
Gly Thr Ser Glu Leu Leu Val Val Asn Ala Ala Asp Ile Arg Leu Glu
                565                 570                 575
Ala Thr Val Gln Leu Pro Ser Arg Val Pro Phe Gly Phe His Gly Thr
                580                 585                 590
Phe Ile Thr Gly Gln Glu Leu Glu Ala Gln Ala Ala
            595                 600

<210> SEQ ID NO 24
<211> LENGTH: 449
<212> TYPE: PRT
<213> ORGANISM: Arabidopsis thaliana

<400> SEQUENCE: 24

Met Gly Asn Ser Glu Met Ser Ala Ser Glu Val Ala Ala Ala Lys Gln
1               5                   10                  15
Lys Asn Val Asp Asp Trp Leu Pro Ile Thr Ser Ser Arg Asn Ala Lys
                20                  25                  30
Trp Trp Tyr Ser Ala Phe His Asn Val Thr Ala Met Val Gly Ala Gly
            35                  40                  45
Val Leu Ser Leu Pro Tyr Ala Met Ser Asn Leu Gly Trp Gly Pro Gly
        50                  55                  60
Val Thr Ile Met Val Met Ser Trp Ile Ile Thr Leu Tyr Thr Leu Trp
65                  70                  75                  80
Gln Met Val Glu Met His Glu Ile Val Pro Gly Lys Arg Leu Asp Arg
                85                  90                  95
```

```
Tyr His Glu Leu Gly Gln His Ala Phe Gly Glu Lys Leu Gly Leu Trp
            100                 105                 110

Ile Val Val Pro Gln Gln Leu Ile Val Glu Val Gly Val Asp Ile Val
            115                 120                 125

Tyr Met Val Thr Gly Gly Ala Ser Leu Lys Lys Val His Gln Leu Val
            130                 135                 140

Cys Pro Asp Cys Lys Glu Ile Arg Thr Thr Phe Trp Ile Met Ile Phe
145                 150                 155                 160

Ala Ser Val His Phe Val Ile Ser His Leu Pro Asn Phe Asn Ser Ile
                165                 170                 175

Ser Ile Ile Ser Leu Ala Ala Ala Val Met Ser Leu Thr Tyr Ser Thr
                180                 185                 190

Ile Ala Trp Ala Ala Ser Val His Lys Gly Val His Pro Asp Val Asp
            195                 200                 205

Tyr Ser Pro Arg Ala Ser Thr Asp Val Gly Lys Val Phe Asn Phe Leu
            210                 215                 220

Asn Ala Leu Gly Asp Val Ala Phe Ala Tyr Ala Gly His Asn Val Val
225                 230                 235                 240

Leu Glu Ile Gln Ala Thr Ile Pro Ser Thr Pro Glu Met Pro Ser Lys
                245                 250                 255

Val Pro Met Trp Arg Gly Val Ile Val Ala Tyr Ile Val Val Ala Ile
            260                 265                 270

Cys Tyr Phe Pro Val Ala Phe Leu Gly Tyr Tyr Ile Phe Gly Asn Ser
            275                 280                 285

Val Asp Asp Asn Ile Leu Ile Thr Leu Glu Lys Pro Ile Trp Leu Ile
            290                 295                 300

Ala Met Ala Asn Met Phe Val Val Ile His Val Ile Gly Ser Tyr Gln
305                 310                 315                 320

Val Phe Phe His Ile Leu Ile Phe Ala Met Pro Val Phe Asp Met Leu
                325                 330                 335

Glu Thr Val Leu Val Lys Lys Met Asn Phe Asn Pro Ser Phe Lys Leu
            340                 345                 350

Arg Phe Ile Thr Arg Ser Leu Tyr Val Ala Phe Thr Met Ile Val Ala
            355                 360                 365

Ile Cys Val Pro Phe Phe Gly Gly Leu Leu Gly Phe Phe Gly Gly Phe
            370                 375                 380

Ala Phe Ala Pro Thr Thr Tyr Tyr Leu Pro Cys Ile Met Trp Leu Val
385                 390                 395                 400

Leu Lys Lys Pro Lys Arg Phe Gly Leu Ser Trp Thr Ala Asn Trp Val
                405                 410                 415

Cys Ser Leu Val Ile Asn Gly Val Leu Leu Thr Ile Leu Ala Pro Ile
                420                 425                 430

Gly Gly Leu Arg Thr Ile Ile Ile Asn Ala Lys Thr Tyr Lys Phe Phe
            435                 440                 445

Ser
```

```
<210> SEQ ID NO 25
<211> LENGTH: 418
<212> TYPE: PRT
<213> ORGANISM: Arabidopsis thaliana

<400> SEQUENCE: 25

Met Lys Thr Leu Arg Asp Leu Gln Asp Gln Ser Phe Glu Leu Glu Asp
 1               5                  10                  15
```

-continued

Trp Leu Pro Ile Thr Ala Ser Arg Asn Ala Asn Trp Tyr Tyr Ser Ala
            20                  25                  30

Phe His Asn Val Thr Ala Ile Val Gly Ala Gly Val Leu Gly Leu Pro
        35                  40                  45

Tyr Ala Met Ser Glu Leu Gly Trp Gly Pro Gly Val Val Leu Ile
    50                  55                  60

Leu Ser Trp Val Ile Thr Leu Tyr Thr Phe Trp Gln Met Ile Glu Met
65                  70                  75                  80

His Glu Met Phe Glu Gly Lys Arg Phe Asp Arg Tyr His Glu Leu Gly
                85                  90                  95

Gln Ala Ala Phe Gly Lys Lys Leu Gly Leu Tyr Ile Val Val Pro Leu
            100                 105                 110

Gln Leu Leu Val Glu Thr Ser Ala Cys Ile Val Tyr Met Val Thr Gly
        115                 120                 125

Gly Glu Ser Leu Lys Lys Ile His Gln Leu Ser Val Gly Asp Tyr Glu
    130                 135                 140

Cys Arg Lys Leu Lys Val Arg His Phe Ile Leu Ile Phe Ala Ser Ser
145                 150                 155                 160

Gln Phe Val Leu Ser Leu Leu Lys Asn Phe Asn Ser Ile Ser Gly Val
                165                 170                 175

Ser Leu Val Ala Ala Val Met Ser Met Ser Tyr Ser Thr Ile Ala Trp
            180                 185                 190

Val Ala Ser Leu Thr Lys Gly Val Ala Asn Asn Val Glu Tyr Gly Tyr
        195                 200                 205

Lys Arg Arg Asn Asn Thr Ser Val Pro Leu Ala Phe Leu Gly Ala Leu
    210                 215                 220

Gly Glu Met Ala Phe Ala Tyr Ala Gly His Asn Val Val Leu Glu Ile
225                 230                 235                 240

Gln Ala Thr Ile Pro Ser Thr Pro Glu Asn Pro Ser Lys Arg Pro Met
                245                 250                 255

Trp Lys Gly Ala Ile Val Ala Tyr Ile Ile Val Ala Phe Cys Tyr Phe
            260                 265                 270

Pro Val Ala Leu Val Gly Phe Trp Thr Phe Gly Asn Asn Val Glu Glu
        275                 280                 285

Asn Ile Leu Lys Thr Leu Arg Gly Pro Lys Gly Leu Ile Ile Val Ala
    290                 295                 300

Asn Ile Phe Val Ile Ile His Leu Met Gly Ser Tyr Gln Val Tyr Ala
305                 310                 315                 320

Met Pro Val Phe Asp Met Ile Glu Ser Val Met Ile Lys Lys Trp His
                325                 330                 335

Phe Ser Pro Thr Arg Val Leu Arg Phe Thr Ile Arg Trp Thr Phe Val
            340                 345                 350

Ala Ala Thr Met Gly Ile Ala Val Ala Leu Pro His Phe Ser Ala Leu
        355                 360                 365

Leu Ser Phe Phe Gly Gly Phe Ile Phe Ala Pro Thr Thr Tyr Phe Ile
    370                 375                 380

Pro Cys Ile Ile Trp Leu Ile Leu Lys Lys Pro Lys Arg Phe Ser Leu
385                 390                 395                 400

Ser Trp Cys Ile Asn Trp Ala Ser Gly Thr Pro Phe Gly Leu Phe
                405                 410                 415

Val Asn

<210> SEQ ID NO 26

-continued

```
<211> LENGTH: 446
<212> TYPE: PRT
<213> ORGANISM: Arabidopsis thaliana

<400> SEQUENCE: 26

Met Val Gln Ala Pro His Asp His Gln Asp Asp Glu Lys Leu
 1               5                  10                  15

Ala Ala Ala Arg Gln Lys Glu Ile Glu Asp Trp Leu Pro Ile Thr Ser
                20                  25                  30

Ser Arg Asn Ala Lys Trp Trp Tyr Ser Ala Phe His Asn Val Thr Ala
            35                  40                  45

Met Val Gly Ala Gly Val Leu Gly Leu Pro Tyr Ala Met Ser Gln Leu
    50                  55                  60

Gly Trp Gly Pro Gly Ile Ala Val Leu Val Leu Ser Trp Val Ile Thr
 65                  70                  75                  80

Leu Tyr Thr Leu Trp Gln Met Val Glu Met His Glu Met Val Pro Gly
                85                  90                  95

Lys Arg Phe Asp Arg Tyr His Glu Leu Gly Gln His Ala Phe Gly Glu
                100                 105                 110

Lys Leu Gly Leu Tyr Ile Val Val Pro Gln Gln Leu Ile Val Glu Ile
            115                 120                 125

Gly Val Cys Ile Val Tyr Met Val Thr Gly Gly Lys Ser Leu Lys Lys
        130                 135                 140

Phe His Glu Leu Val Cys Asp Asp Cys Lys Pro Ile Lys Leu Thr Tyr
145                 150                 155                 160

Phe Ile Met Ile Phe Ala Ser Val His Phe Val Leu Ser His Leu Pro
                165                 170                 175

Asn Phe Asn Ser Ile Ser Gly Ser Phe Ser Cys Cys Arg Tyr Val
                180                 185                 190

Ser Gln Leu Leu Asn Asn Arg Met Gly Ile Ile Ser Lys Gln Arg Cys
            195                 200                 205

Ser Arg Arg Arg Ser Ile Arg Leu Gln Ser Glu Asn Asn Ser Arg Tyr
        210                 215                 220

Val Phe Asn Phe Phe Ser Gly Leu Gly Asp Val Ala Phe Ala Tyr Ala
225                 230                 235                 240

Gly His Asn Val Val Leu Glu Ile Gln Ala Thr Ile Pro Ser Thr Pro
                245                 250                 255

Glu Lys Pro Ser Lys Gly Pro Met Trp Arg Gly Val Ile Val Ala Tyr
            260                 265                 270

Ile Val Val Ala Leu Cys Tyr Phe Pro Val Ala Leu Val Gly Tyr Tyr
        275                 280                 285

Ile Phe Gly Asn Gly Val Glu Asp Asn Ile Leu Met Ser Leu Lys Lys
    290                 295                 300

Pro Ala Trp Leu Ile Ala Thr Ala Asn Ile Phe Val Val Ile His Val
305                 310                 315                 320

Ile Gly Ser Tyr Gln Ile Tyr Ala Met Pro Val Phe Asp Met Met Glu
                325                 330                 335

Thr Leu Leu Val Lys Lys Leu Asn Phe Arg Pro Thr Thr Leu Arg
            340                 345                 350

Phe Phe Val Arg Asn Phe Tyr Val Ala Ala Thr Met Phe Val Gly Met
        355                 360                 365

Thr Phe Pro Phe Phe Gly Gly Leu Leu Ala Phe Phe Gly Gly Phe Ala
    370                 375                 380

Phe Ala Pro Thr Thr Tyr Phe Leu Pro Cys Val Ile Trp Leu Ala Ile
```

```
385             390             395             400
Tyr Lys Pro Lys Tyr Ser Leu Ser Trp Trp Ala Asn Trp Val Cys
            405             410             415

Ile Val Phe Gly Leu Phe Leu Met Val Leu Ser Pro Ile Gly Gly Leu
            420             425             430

Arg Thr Ile Val Ile Gln Ala Lys Gly Tyr Lys Phe Tyr Ser
            435             440             445
```

<210> SEQ ID NO 27
<211> LENGTH: 462
<212> TYPE: PRT
<213> ORGANISM: Nicotiana sylvestris

<400> SEQUENCE: 27

```
Met Val Ala Ser Pro Asp Asn Ala Ala Asp Gly Arg Thr Val Lys
 1               5              10              15

Asn Lys Arg Pro Ile Asp Glu Trp Leu Pro Ile Thr Ser Ser Arg Asn
            20              25              30

Gly Gln Asn Gly Gly Tyr Ser Ala Phe His Asn Val Thr Ala Met Val
            35              40              45

Gly Ala Gly Val Leu Gly Leu Pro Tyr Ala Met Ser Glu Leu Gly Trp
    50              55                  60

Gly Pro Gly Val Thr Val Met Val Val Ser Trp Val Ile Thr Leu Tyr
 65              70              75                      80

Thr Leu Trp Gln Met Val Glu Cys Lys Lys Cys Pro Gly Met Leu Ala
                85              90                  95

Gly Thr Cys Ile Asp Asp His Lys Leu Ala Val Ser Asn Val Phe Gly
            100             105             110

Asn Lys Leu Gly Leu Trp Ile Val Pro Gln Gln Leu Val Val Glu
            115             120             125

Val Gly Ile Asp Ile Val Tyr Met Val Thr Gly Gly Lys Ser Phe Gln
    130             135                 140

Lys Ser Ile Val Leu Val Cys Lys Asp Asn Cys Lys Asp Ile Lys Leu
145             150             155             160

Thr Tyr Tyr Ile Met Ile Phe Ala Ser Val His Phe Val Leu Ser His
                165             170             175

Leu Pro Asn Phe Asn Ala Ile Ser Gly Val Ser Leu Val Ala Ala Ile
            180             185             190

Met Ser Leu Ser Tyr Cys Thr Ile Ala Trp Gly Ala Ser Ile Val Leu
            195             200             205

Gly Val Gln Pro Asp Val Glu Tyr Glu Tyr Arg Ala Glu Asn Thr Gly
    210             215                 220

Glu Gly Ile Phe Asn Phe Phe Ser Gly Leu Gly Glu Val Ala Phe Ala
225             230             235             240

Tyr Ala Gly His Asn Val Val Leu Glu Ile Gln Ala Thr Ile Pro Ser
                245             250             255

Thr Pro Glu Lys Pro Ser Lys Gly Pro Met Trp Lys Gly Val Leu Val
            260             265             270

Ala Tyr Ile Ile Val Ala Leu Cys Tyr Phe Pro Val Ala Ile Ile Gly
            275             280             285

Tyr Trp Ile Phe Gly Asn Ser Val Ser Asn Asn Ile Leu Ile Ser Leu
    290             295                 300

Glu Lys Pro Thr Trp Leu Ile Val Leu Ala Asn Ala Phe Val Val Ile
305             310             315             320
```

-continued

Thr Leu Leu Gly Ala Tyr Gln Leu Tyr Ala Ile Pro Val Phe Asp Met
                325                 330                 335

Leu Glu Thr Tyr Leu Val Arg Lys Leu Lys Phe Lys Pro Thr Trp Tyr
            340                 345                 350

Leu Arg Phe Met Thr Arg Asn Leu Tyr Val Ala Phe Thr Met Phe Val
            355                 360                 365

Gly Ile Ile Phe Pro Phe Leu Trp Gly Leu Leu Gly Phe Leu Gly Gly
        370                 375                 380

Phe Ala Phe Ala Pro Thr Thr Tyr Phe Leu Pro Cys Ile Met Trp Leu
385                 390                 395                 400

Ser Ile Tyr Lys Pro Lys Arg Trp Gly Leu Ser Trp Thr Ser Asn Trp
                405                 410                 415

Ile Cys Ile Ile Val Gly Val Met Leu Thr Val Leu Ala Pro Ile Gly
            420                 425                 430

Gly Leu Arg Thr Ile Ile Gln Ala Lys Asp Tyr Asn Phe Phe Tyr
            435                 440                 445

Trp Asp Ser Leu Ser Gly Ser Leu Ala Phe Gly Lys Lys Gly
        450                 455                 460

<210> SEQ ID NO 28
<211> LENGTH: 1749
<212> TYPE: PRT
<213> ORGANISM: Synechocystis PCC6803

<400> SEQUENCE: 28

Met Val Glu Ile Leu Leu Ile Ser Pro Leu Ile Ala Val Leu Asn Pro
1               5                   10                  15

Ser Leu Arg Leu Phe Cys Leu Ala Leu Leu Ala Cys Ser Ser Ser Phe
            20                  25                  30

Ser Gly Asn Val Leu Ala Gln Asn Ile Thr Pro Ala Pro Asp Gly Thr
        35                  40                  45

Gly Thr Thr Val Asp Ala Gln Gly Asn Gln Phe Asn Ile Gly Gly Gly
    50                  55                  60

Ser Leu Ser Gly Asp Gly Gln Asn Leu Phe His Ser Leu Gln Gln Phe
65                  70                  75                  80

Gly Leu Asp Gln Gly Gln Ile Ala Asn Phe Leu Ser Asn Pro Asp Ile
                85                  90                  95

Arg Asn Ile Leu Thr Arg Ile Val Gly Gly Asp Ala Ser Ile Ile Asn
            100                 105                 110

Gly Leu Ile Gln Val Ser Gly Gly Asn Ala Asn Leu Phe Leu Met Asn
        115                 120                 125

Pro Ala Gly Met Ile Phe Gly Pro Asn Ala Ser Ile Asn Val Pro Gly
    130                 135                 140

Asp Phe Val Val Thr Thr Gly Ser Ala Ile Gly Phe Gly Asn Asp Gln
145                 150                 155                 160

Trp Phe Gln Val Phe Ser Asp Asn Asp Tyr Asn Ala Leu Ile Gly Asn
                165                 170                 175

Pro Ser Gln Phe Ala Phe Asp Leu Ala Asn Pro Gly Leu Ile Ile Asn
            180                 185                 190

Ala Gly Asp Leu Ser Val Thr Glu Gly Lys Asn Leu Thr Phe Leu Ala
        195                 200                 205

Gly Asn Ile Val Asn Thr Gly Ser Leu Ala Ala Pro Gly Gly Asn Ile
    210                 215                 220

Thr Val Ala Ala Val Pro Gly Gln Asn Arg Ile Arg Ile Ser Gln Ala
225                 230                 235                 240

-continued

```
Gly Ser Leu Leu Ser Leu Glu Val Glu Val Ser Pro Gln Met Asn Gln
            245                 250                 255
Gly Gly Ser Phe Ser Val Leu Asp Leu Pro Thr Leu Thr Gln Gly
            260                 265                 270
Ala Ser Asn Leu Asp Leu Gly Leu Ala Val Gln Pro Asn Gly Ser Val
            275                 280                 285
Thr Thr Asn Gly Thr Asn Ala Leu Val Ser Pro Leu Pro Gly Ser Val
            290                 295                 300
Thr Ile Ser Gly Asn Val Asp Ala Ser Gly Lys Ser Thr Asn Ile Ser
305                 310                 315                 320
Ser Gly Gly Gln Val Ala Ile Ala Gly Asp Gln Ile Ala Val Gln Gly
            325                 330                 335
Ala Thr Val Asp Val Ser Gly Asn Gly Gly Gly Thr Val Arg Ile
            340                 345                 350
Gly Gly Asp Phe Gln Gly Gln Leu Thr Leu Pro Asn Ala Ser Gln Thr
            355                 360                 365
Leu Ile Asp Ser Asn Ser Val Val Lys Ala Asp Ala Leu Leu Thr Gly
            370                 375                 380
Asn Gly Gly Thr Val Ile Val Trp Ala Asp Asp Ser Thr Arg Phe Ser
385                 390                 395                 400
Gly Asn Ile Ser Ala Gln Gly Gly Thr Met Gly Gly Asn Gly Gly Phe
            405                 410                 415
Val Glu Thr Ser Gly Ala Lys Ser Leu Met Val Asp Asp Thr Ala Arg
            420                 425                 430
Val Asn Thr Phe Ala Thr Met Gly Glu Leu Gly Thr Trp Leu Leu Asp
            435                 440                 445
Pro Leu Glu Ile Ile Val Gly Thr Thr Asp Asp Leu Leu Ala Asp Pro
            450                 455                 460
Lys Leu Val Ser Val Leu Thr Ile Thr Thr Ser Leu Asp Asn Gly Asn
465                 470                 475                 480
Val Ile Leu Gln Ala Asp Gln Ser Ile Ala Val Gln Ala Asn Phe Ser
            485                 490                 495
Ala Asp Pro Ser Ala Pro Gly Asn Leu Thr Phe Asp Ser Pro Thr Ile
            500                 505                 510
Thr Ile Asp Ala Leu Phe Ser Leu Gly Thr Gly Ser Ile Ile Phe Ala
            515                 520                 525
Asn Thr Gly Pro Ile Asn Thr Gly Asn Thr Leu Val Thr Ser Pro Phe
            530                 535                 540
Thr Asn Leu Asp Phe Asp Asn Lys Ile Gln Leu Asn Ala Asn Thr Thr
545                 550                 555                 560
Phe Thr Ala Pro Gly Tyr Asp Ile Tyr Phe Arg Lys Ser Val Asn Gly
            565                 570                 575
Gly Phe Asp Leu Leu Gly Asn Ala Asn Phe Val Tyr Phe Asp Asp Gly
            580                 585                 590
Ala Gly Ile Thr Thr Pro Leu Lys Ser Phe Gly Val Thr Ala Thr Glu
            595                 600                 605
Ile Tyr Val Gly Asn Asp Ile Val Thr Gln Gly Asn Gln Ile Phe Asp
            610                 615                 620
Gly Val Phe Tyr Gly Leu Gln Pro Val Asn Leu Thr Ser Ser Ala Gly
625                 630                 635                 640
Ser Val Ile Phe Thr Asn Asn Ile Leu Leu Asn Gly Ser Leu Gln Val
            645                 650                 655
```

```
Gln Thr Ala Gln Asn Ile Val Ser Gln Pro Ser Ser Leu Ser Ala
            660                 665                 670

Val Glu Ile Ala Ser Asp Val Leu Leu Asn Ala Gly Gln Asn Val Ser
            675                 680                 685

Phe Gly Asn Ile Asn Thr Arg Gly Gly Asn Val Asp Ile Gln Ala Leu
    690                 695                 700

Gly Asn Ile Ser Thr Gly Ser Ile Val Thr Ser Pro Phe Gly Gly Asn
705                 710                 715                 720

Ala Gly Asn Val Ile Leu Asn Ala Gly Gly Thr Leu Thr Thr Gly Tyr
                725                 730                 735

Ile Glu Thr Ser Gly Thr Asn Gly Gly Asp Val Thr Thr Ser Ser Gly
            740                 745                 750

Ser Asn Thr Ser Thr Ala Tyr Ile Asp Thr Arg Gly Phe Gly Asp Gly
            755                 760                 765

Leu Glu Ile Asp Ser Leu Gly Gly Ala Val Ser Ile Glu Ser Lys Gly
    770                 775                 780

Asp Ile Thr Thr Ala Phe Ile Asp Thr Gly Ala Tyr Ser Ile Glu Ser
785                 790                 795                 800

Phe Asn Glu Gly Thr Gly Gly Asn Val Phe Leu Thr Ala Asp Gly Ser
                805                 810                 815

Ile Thr Thr Asn Tyr Ile Phe Thr Ala Gly Lys Asn Gly Gly Asp Ile
            820                 825                 830

Phe Phe Gln Ala Gly Glu Ser Ile Glu Ile Ile Asp Tyr Leu Asn Thr
            835                 840                 845

Tyr Gly Ser Gln Thr Ser Gly Asp Val Tyr Val Glu Ala Pro Leu Asp
    850                 855                 860

Ile Ser Ile Gly Ser Tyr Ile Tyr Thr Gly Gly Gly Glu Pro Gly
865                 870                 875                 880

Asn Val Phe Leu Gln Ala Gly Gly Asp Ile Thr Thr Ser Tyr Ile Asp
                885                 890                 895

Thr Ser Ala Ala Asn Gly Gly Asp Ile Phe Ile Gln Ser Gly Gly Asp
            900                 905                 910

Thr Glu Val Gly Tyr Leu Phe Thr Lys Gly Tyr Glu Gly Arg Gly Gly
            915                 920                 925

Asp Val Tyr Val Glu Thr Gly Arg Tyr Phe Arg Ala Ile Asp Gly Phe
    930                 935                 940

Leu Leu Gly Glu Glu Gly Pro Phe Ser Val Tyr Thr Ala Gly Leu Thr
945                 950                 955                 960

Val Gly Gly Ser Val Tyr Ile Gln Phe Gly Gly Ser Glu Pro Phe Ile
                965                 970                 975

Ile Gly Asn Pro Ile Thr Asn Gly Thr Ile Gly Ala Ile Ser Ser Gly
            980                 985                 990

Asp Asp Asn Thr Val Pro Ile Gly Thr Pro Pro Ile Phe Asp Thr Phe
            995                 1000                1005

Thr Leu Asp Asn Ile Thr Ile Thr Thr Glu Pro Glu Pro Glu Pro Glu
    1010                1015                1020

Pro Glu Pro Glu Pro Glu Pro Glu Pro Glu Pro Glu Pro Glu Pro Glu
1025                1030                1035                1040

Pro Glu Pro Glu Pro Glu Pro Glu Pro Glu Pro Glu Pro Glu Pro Glu
                1045                1050                1055

Pro Glu Pro Glu Pro Glu Pro Glu Pro Glu Pro Glu Pro Glu Pro Glu
            1060                1065                1070

Pro Glu Pro Glu Pro Glu Pro Glu Pro Glu Pro Glu Pro Glu Pro Glu
```

```
                    1075             1080             1085
Pro Glu Pro Glu Pro Glu Pro Glu Pro Glu Pro Glu Pro Glu
    1090             1095             1100
Pro Glu Pro Glu Pro Glu Pro Glu Pro Glu Pro Glu Pro Glu
1105             1110             1115             1120
Pro Glu Pro Glu Pro Glu Pro Glu Pro Glu Pro Glu Pro Glu
        1125             1130             1135
Pro Glu Pro Glu Pro Glu Pro Glu Pro Glu Pro Glu Pro Glu
            1140             1145             1150
Pro Glu Pro Glu Pro Glu Pro Glu Pro Glu Pro Glu Pro Glu
        1155             1160             1165
Pro Glu Pro Glu Pro Glu Pro Glu Pro Glu Pro Glu Pro Glu
    1170             1175             1180
Pro Glu Pro Glu Pro Glu Pro Glu Pro Glu Pro Glu Pro Glu
1185             1190             1195             1200
Pro Glu Pro Glu Pro Glu Pro Glu Pro Glu Pro Glu Pro Glu
            1205             1210             1215
Pro Glu Pro Glu Pro Glu Pro Glu Leu Pro Thr Pro Ser Ile
        1220             1225             1230
Pro Val Glu Pro Pro Thr Ser Pro Asp Val Glu Glu Ile Asp Glu
    1235             1240             1245
Arg Gln Ile Ser Phe Asp Ile Glu Arg Ser Thr Val Thr Asn Thr Pro
    1250             1255             1260
Ser Leu Glu Ile Gln Ser Gln Asp Thr Val Pro Gly Ile Asn Thr Phe
1265             1270             1275             1280
Ser Ala Asn Val Gly Val Asn Ile Pro Thr Asn Gln Val Val Leu Gln
        1285             1290             1295
Gln Gln Leu Asn Glu Asn Val Glu Glu Ser Ile Ser Ala Gln Phe Thr
        1300             1305             1310
Ser His Leu Asn Leu Asn Ile Asp Ile Glu Leu Val Asn Pro Val Asp
    1315             1320             1325
Val Leu Gln Glu Leu Asn Leu Asn Thr Gly Val Asn Ser Ala Leu Val
    1330             1335             1340
Tyr Ile Tyr Phe Tyr Pro Pro Gly Thr Ala Gly Glu Asn Leu Pro Glu
1345             1350             1355             1360
Trp Gln Leu Ser Ser Asp Ser Glu Pro Ala Ile Pro Pro Val Gly Ser
            1365             1370             1375
Tyr Ala Lys Val Ser His Trp Gln Met Ala Ser Thr Glu Gln Leu Ile
        1380             1385             1390
Ile Pro Pro Asn Asn Asp Pro Arg Pro Asp Asp Gln Leu Val Ile Val
        1395             1400             1405
Val Val Thr Ala Asp Gly Ile Ala Ser Pro Ile Pro Leu Asn Val Ser
    1410             1415             1420
Arg Arg Glu Val Ile Arg Gln Val Glu Met Leu Asn Arg Asn Leu Thr
1425             1430             1435             1440
Ala Ala Asn Arg Gly Asp Asn Tyr Gln Gly Gln Ala Ser Gln Leu Tyr
            1445             1450             1455
Asp Trp Phe Ile Lys Pro Ile Lys Leu Ile Leu Glu Asn Lys Lys Ile
            1460             1465             1470
Glu Asn Ile Ser Phe Ile Leu Asp Arg Gly Leu Arg Ser Leu Pro Met
        1475             1480             1485
Ala Thr Met Tyr Asp Arg Gln Ser Gly Gln Tyr Leu Ile Glu Asp Tyr
    1490             1495             1500
```

```
Ser Val Gly Leu Met Pro Ser Leu Ser Leu Thr Asn Arg Asp Tyr Ala
1505                1510                1515                1520

Pro Leu Thr Gly Ala Gln Ile Leu Ala Met Gly Ala Glu Glu Phe Ala
                1525                1530                1535

Asn Gln Asn Pro Leu Pro Ala Ala Val Glu Val Asp Thr Ile Thr
            1540                1545                1550

Asn Gln Leu Trp Arg Gly Ser Ala Phe Leu Asn Asp Arg Phe Thr Val
        1555                1560                1565

Asp Asn Phe Val Gln Ser Leu Ala Thr Lys Glu Tyr Arg Leu Val His
    1570                1575                1580

Leu Ala Thr His Gly Glu Phe Leu Pro Gly Asn Arg Asn Asn Ser Phe
1585                1590                1595                1600

Val Val Phe Ser Asp Arg Ser Leu Asp Leu Asp Glu Phe Ala Asn Val
                1605                1610                1615

Gly Leu Asp Lys Pro Ile Asp Leu Met Val Leu Ser Ala Cys Arg Thr
                1620                1625                1630

Ala Val Gly Asp Phe Asp Ala Glu Leu Gly Phe Ala Gly Leu Ala Val
            1635                1640                1645

Lys Thr Gly Val Lys Thr Ala Ile Gly Ser Leu Trp Tyr Val Ser Asp
    1650                1655                1660

Glu Ala Thr Phe Ala Leu Met Thr Ser Phe Tyr Asp Arg Leu Gln Pro
1665                1670                1675                1680

Ala Pro Ile Lys Ala Lys Ala Leu Gln Gln Ala Gln Leu Ser Leu Leu
                1685                1690                1695

Arg Gly Glu Ile Arg Val Val Asp Gly Asn Leu Val Leu Gly Asp Gly
            1700                1705                1710

Thr Asn Ile Ser Leu Ala Asp Leu Pro Ala Asp Ile Arg Gln Arg Leu
        1715                1720                1725

Ala Thr Gln Asp Leu Ser His Pro Tyr Phe Trp Ser Gly Phe Thr Leu
    1730                1735                1740

Val Gly Ser Pro Trp
1745
```